US008802647B2

(12) United States Patent
Mohapatra et al.

(10) Patent No.: US 8,802,647 B2
(45) Date of Patent: *Aug. 12, 2014

(54) MATERIALS AND METHODS FOR PREVENTION AND TREATMENT OF RNA VIRAL DISEASES

(71) Applicant: University of South Florida, Tampa, FL (US)

(72) Inventors: Shyam S. Mohapatra, Lutz, FL (US); Aruna K. Behera, Watertown, MA (US)

(73) Assignee: University of South Florida, Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,470

(22) Filed: Sep. 17, 2012

(65) Prior Publication Data

US 2013/0129702 A1 May 23, 2013

Related U.S. Application Data

(60) Continuation of application No. 12/638,800, filed on Dec. 15, 2009, now Pat. No. 8,293,717, which is a continuation of application No. 12/016,041, filed on Jan. 17, 2008, now abandoned, which is a division of application No. 10/426,436, filed on Apr. 30, 2003, now Pat. No. 7,354,908.

(60) Provisional application No. 60/319,313, filed on Jun. 12, 2002, provisional application No. 60/319,216, filed on Apr. 30, 2002.

(51) Int. Cl.
*A01N 43/04* (2006.01)
*C12N 15/63* (2006.01)
*C12P 19/34* (2006.01)
*C07H 21/02* (2006.01)
*C07H 21/04* (2006.01)

(52) U.S. Cl.
USPC ............... 514/44; 435/6; 435/91.1; 435/455; 536/23.1; 536/23.2

(58) Field of Classification Search
USPC ................. 435/6, 91.1, 455; 514/44, 1, 2; 536/23.1, 23.5, 23.2
See application file for complete search history.

(56) References Cited

U.S. PATENT DOCUMENTS

| | | |
|---|---|---|
| 4,414,150 A | 11/1983 | Goeddel |
| 4,456,748 A | 6/1984 | Goeddel |
| 4,678,751 A | 7/1987 | Goeddel |
| 4,695,623 A | 9/1987 | Stabinsky |
| 4,897,471 A | 1/1990 | Stabinsky |
| 5,571,515 A | 11/1996 | Scott et al. |
| 5,731,490 A | 3/1998 | Mak et al. |
| 5,744,166 A | 4/1998 | Illum |
| 5,766,864 A | 6/1998 | Uno et al. |
| 5,770,191 A | 6/1998 | Johnson et al. |
| 5,831,062 A | 11/1998 | Taylor et al. |
| 5,853,755 A | 12/1998 | Foldvari |
| 5,861,300 A | 1/1999 | Silverman et al. |
| 5,866,787 A | 2/1999 | Silverman et al. |
| 6,120,762 A | 9/2000 | Johnson et al. |
| 6,121,247 A | 9/2000 | Huang et al. |
| 6,168,923 B1 | 1/2001 | Scott et al. |
| 6,210,663 B1 | 4/2001 | Ertl |
| 6,218,180 B1 | 4/2001 | Kurtzman et al. |
| 6,379,897 B1 | 4/2002 | Weidenhammer et al. |
| 6,399,322 B1 | 6/2002 | Glimcher et al. |
| 6,429,025 B1 | 8/2002 | Parce et al. |
| 6,475,995 B1 | 11/2002 | Roy et al. |
| 6,489,306 B2 | 12/2002 | Mohapatra et al. |
| 6,653,124 B1 | 11/2003 | Freeman |
| 6,693,086 B1 | 2/2004 | Dow et al. |
| 6,710,035 B2 | 3/2004 | Felgner et al. |
| 6,803,238 B1 | 10/2004 | Eggers |
| 6,811,788 B2 | 11/2004 | Yu |
| 7,029,838 B2 | 4/2006 | Williams et al. |
| 7,041,246 B2 | 5/2006 | Fillmore et al. |

(Continued)

FOREIGN PATENT DOCUMENTS

| | | |
|---|---|---|
| EP | 343388 A2 | 11/1989 |
| WO | WO 90/09780 A1 | 9/1990 |

(Continued)

OTHER PUBLICATIONS

An, Z. et al. "Interferon Gamma is Highly Effective Against Orthotopically-Implanted Human Pleural Adenocarcinoma in Nude Mice" *Anticancer Research*, 1996, 16:2546-2552.

(Continued)

*Primary Examiner* — Jane Zara
(74) *Attorney, Agent, or Firm* — Saliwanchik, Lloyd & Eisenschenk

(57) ABSTRACT

The subject invention concerns a method of inhibiting an RNA virus infection within a patient by increasing the amount of 2-5 oligoadenylate synthetase (2-5 AS) activity within the patient. Preferably, the preventative and therapeutic methods of the present invention involve administering a nucleotide encoding 2-5 AS, or at least one catalytically active fragment thereof, such as the p40, p69, p100 subunits, to a patient in need thereof. The present inventors have determined that overexpression of 2-5AS causes a reduction in epithelial cell damage, reduction in infiltration of mononuclear cells in the peribronchiolar and perivascular regions, and reduction in thickening of the septa in the lungs. Levels of chemokines, such as MIP1-α, are also reduced upon overexpression of 2-5AS. The subject invention also pertains to pharmaceutical compositions containing a nucleotide sequence encoding 2-5 AS and a pharmaceutically acceptable carrier, as well as vectors for delivery of the 2-5 AS nucleotide sequence.

8 Claims, 14 Drawing Sheets

(56) References Cited

U.S. PATENT DOCUMENTS

| | | | |
|---|---|---|---|
| 7,052,685 | B1 | 5/2006 | Rook |
| 7,052,829 | B2 | 5/2006 | Williams et al. |
| 7,081,954 | B2 | 7/2006 | Sandstrom |
| 7,267,958 | B2 | 9/2007 | Dordick et al. |
| 7,354,908 | B2* | 4/2008 | Mohapatra et al. ......... 514/44 R |
| 7,595,303 | B1 | 9/2009 | Mohapatra et al. |
| 8,293,717 | B2* | 10/2012 | Mohapatra et al. ......... 514/44 R |
| 2001/0006951 | A1 | 7/2001 | Mohapatra et al. |
| 2002/0044919 | A1 | 4/2002 | Yu |
| 2003/0068333 | A1 | 4/2003 | Mohapatra et al. |
| 2003/0134810 | A1 | 7/2003 | Springate et al. |
| 2003/0138404 | A1 | 7/2003 | Maroun |
| 2003/0198624 | A1 | 10/2003 | Mohapatra et al. |
| 2004/0009152 | A1 | 1/2004 | Mohapatra et al. |
| 2004/0248323 | A1 | 12/2004 | Zhou et al. |
| 2005/0025742 | A1 | 2/2005 | Engler et al. |
| 2005/0054052 | A1 | 3/2005 | Carr et al. |
| 2005/0054053 | A1 | 3/2005 | Aguinaldo et al. |
| 2005/0084478 | A1 | 4/2005 | Liu et al. |
| 2005/0266093 | A1 | 12/2005 | Mohapatra |
| 2005/0272650 | A1 | 12/2005 | Mohapatra |
| 2005/0287118 | A1 | 12/2005 | Tian et al. |
| 2006/0276382 | A1 | 12/2006 | Mohapatra |
| 2007/0116767 | A1 | 5/2007 | Mohapatra |
| 2009/0280143 | A1 | 11/2009 | Mohapatra et al. |

FOREIGN PATENT DOCUMENTS

| | | |
|---|---|---|
| WO | WO 96/39806 A1 | 12/1996 |
| WO | WO 98/02457 A1 | 1/1998 |
| WO | WO 99/19496 A1 | 4/1999 |
| WO | WO 01/22970 A1 | 4/2001 |
| WO | WO 02/06343 A2 | 1/2002 |
| WO | WO 02/081638 A2 | 10/2002 |
| WO | WO 03/028759 A1 | 4/2003 |
| WO | WO 03/072035 * | 9/2003 |
| WO | WO 03/074561 A1 | 9/2003 |
| WO | WO 03/089003 A1 | 10/2003 |
| WO | WO 03/092618 A2 | 11/2003 |
| WO | WO 2004/022003 A3 | 3/2004 |
| WO | WO 2004/074314 A2 | 8/2004 |
| WO | WO 2005/094420 A3 | 10/2005 |
| WO | WO 2005/105136 A1 | 11/2005 |

OTHER PUBLICATIONS

Iqbal, M. et al. "Nasal delivery of chitosan-DNA plasmid expressing epitopes of respiratory syncytial virus (RSV) induces protective CTL responses in BALB/c mice" *Vaccine*, 2003, 21:1478-1485.

Nanni, P. et al. "Therapy of murine mammary carcinoma metastasis with interferon γ and MHC gene-transduced tumour cells" *British Journal of Cancer*, 1996, 74:1564-1569.

Smyth, M. et al. "Tumor Necrosis Factor-related Apoptosis-inducing Ligand (TRIAL) contributes to Interferon γ-dependent Natural Killer Cell Protection from Tumor Metastasis" *J. Exp. Med.*, 2001, 193:661-670.

Office Action mailed Sep. 26, 2011 in U.S. Appl. No. 11/117,169, filed Apr. 27, 2005.

Boccaccio, G.L. et al. "Non-coding plasmid DNA induces IFN-γ in vivo and suppresses autoimmune encephalomyelitis" International Immunology, Feb. 1999, 11(2):289-296.

Boguniewicz, M. et al. "The effects of nebulized recombinant interferon-γ in asthmatic airways" *J Allergy Clin Immunol*, Jan. 1995, 95(1):133-135.

Boguniewicz, M. et al. "Atopy, airway responsiveness, and genes" Thorax, 1996, 51(Supplement 2):S55-S59.

Cohn, L. et al. "T Helper 1 Cells and Interferon γ Regulate Allergic Airway Inflammation and Mucus Production" Journal of Experimental Medicine, Nov. 1999, 190(9):1309-1317.

Nowak, J.M. et al. "The influence of cotinine on the non-small-cell lung cancer line A549" *Postepy Hig Med Dosw.* (online), Jan. 29, 2009, 63:1-7.

Agnihotri, S.A. et al. "Recent advances on chitosan-based micro- and nanoparticles in drug delivery" *Journal of Controlled Release*, Nov. 2004, 100(1):5-28.

Agrawal, S. et al. "Antisense therapeutics: is it as simple as complementary base recognition?" *Molecular Medicine Today*, Feb. 2000, 6(2):72-81.

Altman, C.A. et al. "Respiratory Syncytial Virus in Patients with Congenital Heart Disease: A Contemporary Look at Epidemiology and Success of Preoperative Screening" *Pediatric Cardiology*, Sep. 2000, 21(5):433-438.

Antoniou, K.M. et al. "Interferons and Their Application in the Diseases of the Lung" *Chest*, Jan. 2003, 123(1):209-216.

Aral, C. at al. "Preparation and in vitro transfection efficiency of chitosan microspheres containing plasmid DNA:poly(L-lysine) complexes" *J Pharm Pharmaceut Sci*, Sep.-Dec. 2003, 6(3):321-326.

Baglioni, C. et al. "Cleavage of Nascent Reovirus mRNA by Localized Activation of the 2'-5'-Oligoadenylate-Dependent Endoribonuclease" *Journal of Virology*, Dec. 1984, 52(3):865-871.

Banerjee, R. et al. "Selective inhibition of hepatitis B virus and human immunodeficiency virus sequence-promoted gene expression by cotransfected poly(I):poly(C)" *Virology*, Nov. 1990, 179(1):410-415.

Barnett, B.G. et al. "Targeted adenoviral vectors" *Biochimica et Biophysica Acta*, 2002, 1575:1-14.

Behera, A.K. et al. "Adenovirus-Mediated Interferon γ Gene Therapy for Allergic Asthma: Involvement of Interleukin 12 and STAT4 Signaling" *Human Gene Therapy*, Sep. 2002, 13:1697-1709.

Behera, A.K. et al. "2'-5' Oligoadenylate Synthetase Plays a Critical Role in Interferon-γ Inhibition of Respiratory Syncytial Virus Infection of Human Epithelial Cells" *The Journal of Biological Chemistry*, Jul. 2002, 277(28):25601-25608.

Benavente, J. et al. "Indiscriminate degradation of RNAs in interferon-treated, vaccinia virus-infected mouse L cells" *Journal of Virology*, Sep. 1984, 51:866-871.

Benech, P. et al. "Structure of two forms of the interferon-induced (2'-5') oligo A synthetase of human cells based on cDNAs and gene sequences" *The EMBO Journal*, 1985, 4(9):2249-2256.

Bisbal, C. et al. "Cloning and Characterization of a RNase L Inhibitor: A New Component of the Interferon-Regulated 2-5A Pathway" *The Journal of Biological Chemistry*, Jun. 1995, 270(22):13308-13317.

Blanck, G. "Components of the IFN-γ Signaling Pathway in Tumorigenesis" *Archivum Immunologiae et Therapiae Experimentalis*, 2002, 50:151-158.

Branch, A.D. "A good antisense molecule is hard to find" *TIBS*, Feb. 1998, 23:45-50.

Cevc, G. et al. "Ultraflexible vesicles, Transfersomes, have an extremely low pore penetration and transport therapeutic amounts of insulin across the intact mammalian skin" *Biochimica et Biophysica Acta*, 1998, 1368:201-215.

Chebath, J. et al. "Four Different Forms of Interferon-induced 2',5'-Oligo(A) Synthetase Identified by Immunoblotting in Human Cells" *The Journal of Biological Chemistry*, Mar. 1987, 262(8):3852-3857.

Chen, J.H. "Application of cationic polymer vector for gene delivery systems" Yao Xue Xue Bao, Apr. 2003, 38(4):316-20, abstract.

Chen, W.R. et al. "Enhancement of Laser Cancer Treatment by a Chitosan-derived Immunoadjuvant" *Photochemistry and Photobiology*, 2005, 81:190-195.

Chirila, T.V. et al. "The use of synthetic polymers for delivery of therapeutic antisense oligodeoxynucleotides" *Biomaterials*, 2002, 23:321-342.

Coccia, E.M. et al. "Cells Resistant to Interferon-β Respond to Interferon-γ via the Stat1-IRF-1 Pathway" *Virology*, 1995, 211:113-122.

Cohen, B. et al. "Enhancer-like interferon responsive sequences of the human and murine (2'-5') oligoadenylate synthetase gene promoters" *The EMBO Journal*, 1988, 7(5):1411-1419.

Cohen, A.D. et al. "Modulating the immune response to genetic immunization" *FASEB J*, 1998, 12:1611-1626.

Collins, P.L. et al. "Production of infectious human respiratory syncytial virus from cloned cDNA confirms an essential role for the transcription elongation factor from the 5' proximal open reading

(56) References Cited

OTHER PUBLICATIONS frame of the M2 mRNA in gene expression and provides a capability for vaccine development" *Proc Natl Acad Sci USA*, Dec. 1995, 92:11563-11567.

Connors, M. et al. "Respiratory Syncytial Virus (RSV) F, G, M2 (22K), and N Proteins Each Induce Resistance to RSV Challenge, but Resistance Induced by M2 and N Proteins Is Relatively Short-Lived" *Journal of Virology*, Mar. 1991, 65(3):1634-1637.

Corrias, M.V. et al. "Induction of 2,5 OAS Gene Expression and Activity Is Not Sufficient for IFN-γ-Induced Neuroblastoma Cell Differentiation" *Int J Cancer*, 1995, 62:223-229.

Crooke, S.T. "Basic principles of antisense therapeutics" in Antisense Research and Application, Ed. By Crooke, S.T., 1998, Chapter 1, pp. 1-50.

David, S. et al. "2'-5'-Oligoadenylate Synthetase Gene Expression in Normal and Murine Sarcoma Virus-Transformed NIH 3T3 Cells" *Journal of Virology*, Mar. 1989, 63(3):1116-1122.

Derossi, D. et al. "The Third Helix of the Antennapedia Homeodomain Translocates through Biological Membranes" *The Journal of Biological Chemistry*, Apr. 8, 1994, 269(14):10444-10450.

Dobson, J. "Gene therapy progress and prospects: magnetic nanoparticle-based gene delivery" *Gene Therapy*, 2006, 13:283-287.

Domachowske, J.B. et al. "Respiratory Syncytial Virus Infection: Immune Response, Immunopathogenesis, and Treatment" *Clinical Microbiology Reviews*, Apr. 1999, 12(2):298-309.

Donnerstein, R.L. et al. "Complex atrial tachycardias and respiratory syncytial virus infections in infants" *J Pediatr*, 1994, 125:23-28.

Dow, S. et al. "Systemic and local interferon γ gene delivery to the lungs for treatment of allergen-induced airway hyperresponsivenese in mice" Human Gene Therapy, Aug. 1999, 10: 1905-1914.

Elliott, G. et al. "Intercellular Trafficking and Protein Delivery by a Herpesvirus Structural Protein" *Cell*, Jan. 24, 1997, 88:223-233.

Englebienne, P. et al. "Rnase L in Health and Disease: What Did We Learn Recently" *Journal of Chronic Fatigue Syndrome*, 2003, 11(2):97-109.

Esteban, M. et al. "Identification by Electron Microscopy of the Maturation Steps in Vaccinia Virus Morphogenesis Inhibited by the Interferon-Induced Enzymes, Protein Kinase (PKR), 2-5A Synthetase, and Nitric Oxide Synthase (iNOS)" *Journal of Interferon and Cytokine Research*, 2000, 20:867-877.

Falsey, A.R. et al. "Respiratory Syncytial Virus and Influenza A Infections in the Hospitalized Elderly" *The Journal of Infectious Diseases*, 1995, 172:389-394.

Fixler, D.E. "Respiratory Syncytial Virus Infection in Children with Congenital Heart Disease: A Review" *Pediatr Cardiol*, 1996, 17:163-168.

Flotte, T.R. and Laube, B.L. "Gene therapy in cystic fibrosis" *CHEST*, 2001, 120:124S-131S.

Foldvari, M. and Moreland, A. "Clinical observations with topical liposome-encapsulated interferon alpha for the treatment of genital papillomavirus infections" *J. Liposome Res.*, 1997, 7:115-126.

Foldvari, M. et al. "Liposome encapsulated prostaglandin E1 in erectile dysfunction: Correlation between in vitro delivery through foreskin and efficacy in patients" *Urology*, 1998, 52(5):838-843.

Glezen, W.P. et al. "Risk of Primary Infection and Reinfection With Respiratory Syncytial Virus" *AJDC*, 1986, 140:543-546.

Goeddel, D.V. et al. "The structure of eight distinct cloned human leukocyte interferon cDNAs" *Nature*, Mar. 1981, 290:20-26.

Goswami, B.B. et al. "Degradation of rRNA in Interferon-treated Vaccinia Virus-infected Cells" *The Journal of Biological Chemistry*, Feb. 10, 1984, 259(3):1371-1374.

Grander, D. et al. "In Vivo Induction of the Interferon-Stimulated Protein 2'5'-Oligoadenylate Synthetase in Tumor and Peripheral Blood Cells During IFN-α Treatment of Metastatic Melanoma" *Journal of Interferon and Cytokine Research*, 1998, 18:691-695.

Gray, P.W. et al. "Cloning and expression of murine immune interferon cDNA" *Proc Natl Acad Sci USA*, Oct. 1983, 80:5842-5846.

Groothius, J.R. et al. "Respiratory Syncytial Virus Infection in Children With Bronchopulmonary Dysplasia" *Pediatrics*, 1988, 82:199-203.

Guang Liu, W. et al. "Chitosan and its derivatives—a promising non-viral vector for gene transfection" *Journal of Controlled Release*, 2002, 83:1-11.

Gutterman, J.U. "Cytokine therapeutics: Lessons from interferon α" *Proc. Natl. Acad. Sci. USA*, 1994, 91:1198-1205.

Hall, C.B. et al. "Respiratory Syncytial Virus—From Chimps With Colds to Conundrums and Cures" *The New England Journal of Medicine*, Jul. 4, 1991, 325(1):57-58.

Hall, C.B. et al. "Respiratory Syncytial Virus Infections in Previously Healthy Working Adults" *Clinical Infectious Disease*, Sep. 15, 2001, 33:792-796.

Hartmann, R. et al. "Activation of 2'-5' Oligoadenylate Synthetase by Single-stranded and Double-stranded RNA Aptamers" *The Journal of Biological Chemistry*, Feb. 1998, 273(6):3236-3246.

Hassel, B.A. et al. "A dominant negative mutant of 2-5A-dependent RNase suppresses antiproliferative and antiviral effects of interferon" *The EMBO Journal*, 1993, 12(8):3297-3304.

Hellerman, G.R. et al. "Genetic therapy: on the brink of a new future" *Genetic Vaccines and Therapy*, 2003, 1(1):1-2.

Henco, K. et al. "Structural Relationship of Human Interferon Alpha Genes and Pseudogenes" *J Mol Biol*, 1985, 185:227-260.

Hsu, S.C. et al. "Synergistic effect of immunization with a peptide cocktail inducing antibody, helper and cytotoxic T-cell responses on protection against respiratory syncytial virus" *Journal of General Virology*, 1999, 80:1401-1405.

Jameton, R. et al. "IL-12 Possibilities" *Science*, Sep. 15, 1995, 269(5230):1498-1499.

Jeong, H.J. et al. "Nitric oxide production by high molecular weight water-soluble chitosan via nuclear factor-κB activation" *International Journal of Immunophamacology*, 2000, 22:923-933.

Kaiser, J. "Death Prompts a Review of Gene Therapy Vector" *Science*, Aug. 3, 2007, 317:580.

Kim, T.H. et al. "Efficient gene delivery by urocanic acid-modified chitosan" *Journal of Controlled Release*, 2003, 93:389-402.

Kim, T.H. et al. "Galactosylated chitosan/DNA nanoparticles prepared using water-soluble chitosan as a gene carrier" *Biomaterials*, 2004, 25:3783-3792.

Kinsey, B. et al. "Non-viral gene delivery to the lungs" *Current Gene Therapy*, 2005, 5:181-194.

Köping-Höggård, M. et al. "Improved chitosan-mediated gene delivery based on easily dissociated chitosan polyplexes of highly defined chitosan oligomers" *Gene Therapy*, 2004, 11:1441-1452.

Kumar, R. et al. "Studies on the Role of the 2'-5'-Oligoadenylate Synthetase-RNase L Pathway in Beta Interferon-Mediated Inhibition of Encephalomyocarditis Virus Replication" *Journal of Virology*, Sep. 1988, 62(9):3175-3181.

Kumar, M. et al. "Intranasal IFN-γ gene transfer protects BALB/c mice against respiratory syncytial virus infection" *Vaccine*, 2000; 18:558-567.

Kumar, M. et al. "Role of mucosal IFN-γ gene transfer on allergic sensitization and RSV infection" *J. Allergy Clin. Immunol.*, 2002, 109:S4, abstract No. 78.

Kumar, M. et al. "Intranasal Gene Transfer by Chitosan-DNA Nanospheres Protects BALB/c Mice Against Acute Respiratory Syncytial Virus Infection" *Human Gene Therapy*, Aug. 2002, 13(12):1415-1425.

Kumar, M. et al. "Chitosan IFN-γ-pDNA Nanoparticle (CIN) Therapy for Allergic Asthma" *Genetic Vaccines and Therapy*, 2003, 1(3):1-10.

Kumar, M.N.V.R. et al. "Nanoparticle-mediated gene delivery: state of the art" *Expert Opin. Biol. Ther.*, 2004, 4(8):1213-1224.

Lengyel, P. et al. "Tumor-supressor genes: News about the interferon connection" *Proc Natl Acad Sci USA*, Jul. 1993, 90:5893-5895.

Leong, K.W. et al. "DNA-polycation nanospheres as non-viral gene delivery vehicles" *J. Controlled Release*, 1998, 53:183-193.

Li, X-M. et al. "Mucosal IFN-γ gene transfer inhibits pulmonary allergic responses in mice" *J. Immunol.*, 1996, 157:3216-3219.

Li, X. et al. "Protection against Respiratory Syncytial Virus Infection by DNA Immunization" *J Exp Med*, Aug. 17, 1998, 188(4):681-688.

(56) References Cited

OTHER PUBLICATIONS

Li, X.L. et al. "RNase L Mediates the Antiviral Effect of Interferon through a Selective Reduction in Viral RNA during Encephalomyocarditis Virus Infection" *Journal of Virology*, Apr. 1998, 72(4):2752-2759.

Li, X. et al. "Plasmid DNA Encoding the Respiratory Syncytial Virus G Protein Is a Promising Vaccine Candidate" *Virology*, 2000, 269:54-65.

Lotem, J. et al. "Interferon-gamma inhibits apoptosis induced by wild-type p53, cytotoxic anti-cancer agents and viability factor deprivation in myeloid cells" *Leukemia*, 1995, 9:685-692.

Maitra, R.K. et al. "Regulation of Human Immunodeficiency Virus Replication by 2',5'-Oligoadenylate-Dependent RNase L" *Journal of Virology*, Feb. 1998, 72(2):1146-1152.

Mansouri, S. et al. "Chitosan-DNA nanoparticles as non-viral vectors in gene therapy: strategies to improve transfection efficacy" *European Journal of Pharmaceutics and Biopharmaceutics*, 2004, 57:1-8.

Mao, H-Q. et al. "Chitosan-DNA nanoparticles as gene carriers: synthesis, characterization and transfection efficiency" *J. Controlled Release*, 2001, 70(3):399-421.

Matsuse, H. et al. "Recurrent Respiratory Syncytial Virus Infections in Allergen-Sensitized Mice Lead to Persistent Airway Inflammation and Hyperresponsiveness" *The Journal of Immunology*, 2000, 164:6583-6592.

Matsuse, H. et al. "Differential cytokine mRNA expression in *Dermatophagoides farinae* allergen-sensitized and respiratory syncytial virus-infected mice" *Microbes and Infection*, 2000, 2:753-759.

Millar, B.C. et al. "2',5'-Oligoadenylate synthetase levels in patients with multiple myeloma receiving maintenance therapy with interferon α2b do not correlate with clinical response" *British Journal of Cancer*, 1995, 72:1525-1530.

Mohapatra, S. "Mucosal gene expression vaccine: a novel vaccine strategy for respiratory syncytial virus" *The Pediatric Infectious Disease Journal*, Feb. 2003, 22(2):S100-S104.

Mohapatra, S. Poster materials presented at International RSV Conference on Jun. 22, 2002, Washington, D.C. (9 pages, including abstract and Figures 1-4 with captions).

Monahan, P.E. et al. "Adeno-associated virus vectors for gene therapy: more pros than cons?" *Molecular Medicine Today*, Nov. 2000, 6:433-440.

Montgomery, D. et al. "DNA vaccines" *Pharmacol. Ther.*, 1997, 74:195-205.

Murray, H.W. "Current and future clinical applications of interferon-gamma in host antimicrobial defense" *Intensive Care Med*, 1996, 22(Suppl 4):S456-S461.

Nilsen, T.W. et al. "Double-stranded RNA Causes Synthesis of 2',5'-Oligo(A) and Degradation of Messenger RNA in Interferon-treated Cells" *The Journal of Biological Chemistry*, Aug. 1981, 256(15):7806-7811.

Nilsen, T.W. et al. "Synthesis of (2'-5')Oligoadenylate and Activation of an Endoribonuclease in Interferon-Treated HeLa Cells Infected with Reovirus" *Journal of Virology*, Jun. 1982, 42(3):1039-1045.

Office Action mailed Sep. 19, 2007 in U.S. Appl. No. 11/117,169, filed Apr. 27, 2005.

Okubo, T. et al. "Administration of an IL-12-Encoding DNA Plasmid Prevents the Development of Chronic Graft-Versus-Host Disease (GVHD)" *The Journal of Immunology*, 1999, 162:4013-4017.

Opalinska, J.B. et al. "Nucleic-Acid Therapeutics: Basic Principles and Recent Applications" *Nature Reviews: Drug Discovery*, Jul. 2002, 1:503-514.

Opdenakker, G. et al. "Interaction of interferon with other cytokines" *Experientia*, 1989, 45:513-520.

Park, S-Y. et al. "IFN-γ enhances TRAIL-induced apoptosis through IRF-1" *Eur. J. Biochem.*, 2004, 271(21):4222-4228.

Payne, L.G. et al. "Particle-mediated DNA vaccination of mice, monkeys and men: Looking beyond the dogma" *Current Opinion in Molecular Therapeutics*, 2002, 4:459-466.

Peng, J. et al. "Influence of anions on the formation and properties of chitosan-DNA nanoparticles" *J Nanosci Nanotechnol.*, May 2005, 5(5):713-717, abstract.

Peracchi, A. et al. "Prospects for antiviral ribozymes and deoxyribozymes" *Rev in Medical Virology*, 2004, 14:47-64.

Pizzoferrato, E. et al. "Ectopic Expression of Interferon Regulatory Factor-1 Promotes Human Breast Cancer Cell Death and Results in Reduced Expression of Survivin" *Cancer Research*, Nov. 2004, 64:8381-8388.

Pooga, M. et al. "Cell penetration by transportan" *The FASEB Journal*, Jan. 1998, 12:67-77.

Pouton, C. and Seymour, L. "Key issues in non-viral gene delivery" *Adv. Drug Deliv. Rev.*, 2001, 46:187-203.

Read, M. et al. "Barriers to gene delivery using synthetic vectors" *Advances in Genetics*, 2005, 53:19-46.

Rebouillat, D. et al. "Characterization of the Gene Encoding the 100-kDA Form of Human 2',5'Oligoadenylate Synthetase" *Genomics*, 2000, 70:232-240.

Reis, L.F.L. et al. "Critical role of a common transcription factor, IRF-1, in the regulation of IFN-β and IFN-inducible genes" *The EMBO Journal*, 1992, 11(1):185-193.

Rener, X. et al. "Construction and identification of a recombinant adenovirus which expresses human interferon-γ" *Chinese J. Biotech.*, 1997, 13:1-8.

Robinson, M. et al. "Predictive assessment of respiratory sensitizing potential of proteins in mice" in *Toxicology of Chemical Respiratory Hypersensitivity*, Dearman and Kimber, Eds., 1997, pp. 135-150.

Rosenblum, M.G. et al. "Differential Activity of the 30-kD and the 100-kD Forms of 2'-5' $A_n$ Synthetase Induced by Recombinant Human interferon-α and Interferon-γ" *Journal of Interferon Research*, 1988, 8:275-282.

Roy, K. et al. "Oral gene delivery with chitosan? DNA nanoparticles generates immunologic protection in a murine model of peanut allergy" *Nature Medicine*, 1999, 5(4):387-391.

Sangfelt, O. et al. "Wild-Type p53-Induced Apoptosis in a Burkitt Lymphoma Cell Line is Inhibited by Interferon Gamma" *International Journal of Cancer*, 1996, 67:106-112.

Sarkar, S.N. et al. "The Nature of the Catalytic Domain of 2'-5' -Oligoadenylate Synthetases" *The Journal of Biological Chemistry*, Sep. 1999, 274(35):25535-25542.

Sarkar, S.N. et al. "Natural Mutations in a 2'-5' Oligoadenylate Synthetase Transgene Revealed Residues Essential for Enzyme Activity" *Biochemistry*, 2005, 44:6837-6843.

Sarkar, S.N. et al. "Assays for the Interferon-Induced Enzyme 2',5' Oligoadenylate Synthetases" *Methods in Molecular Medicine*, 2005, 116:81-101.

Senior, K. "Adeno-associated virus vectors under scrutiny" *The Lancet*, Apr. 6, 2002, 359:1216.

Sethi, S.K. et al. "Interferon-gamma (IFN-γ) down-regulates the rhinovirus-induced expression of intercellular adhesion molecule-1 (ICAM-1) on human airway epithelial cells" *Clin. Exp. Immunol.*, 1997, 110:362-369.

Shay, D.K. et al. "Bronchiolitis-Associated Hospitalizations Among US Children, 1980-1996" *JAMA*, 1999, 282:1440-1446.

Shay, D.K. et al. "Bronchiolitis-Associated Mortality and Estiamtes of Respiratory Syncytial Virus-Associated Deaths among US Children, 1979-1997" *The Journal of Infectious Diseases*, 2001, 183:16-22.

Shibata, Y. et al. "Alveolar Macrophage Priming by Intravenous Administration of Chitin Particles, Polymers of N-Acetyl-D-Glucosamine, in Mice" *Infection and Immunity*, May 1997, 65(5):1734-1741.

Short, S.M. et al. "Percutaneous absorption of biologically-active interferon-gamma in a human skin graft-nude mouse model" *Pharm. Res.*, 1996, 13:1020-1027.

Silverman, R.H. "Implications for Rnase L in Prostate Cancer Biology" *Biochemistry*, Feb. 25, 2003, 42(7):1805-1812.

Simmons, C.P. et al. "Mucosal delivery of a respiratory syncytial virus CTL peptide with enterotoxin-based adjuvants elicits protective, immunopathogenic, and immunoregulatory antiviral CD8+ T cell responses" *J. Immun.*, 2001, 166:1106-1113.

Simoes, E.A.F. "Respiratory syncytial virus infection" *The Lancet*, Sep. 4, 1999, 354:847-852.

(56) References Cited

OTHER PUBLICATIONS

Streuli, M. et al. "At Least Three Human Type α Interferons: Structure of α2" *Science*, Sep. 19, 1980, 209:1343-1347.

Tang, Y.W. et al. "Determinants and kinetics of cytokine expression patterns in lungs of vaccinated mice challenged with respiratory syncytial virus" *Vaccine*, 1997, 15(6/7):597-602.

Troxler, M. et al. "Intracellular Localization of Polivirus RNA by in Situ Hybridization at the Ultrastructural Level Using Single-Stranded Riboprobes" *Virology*, 1992, 191:687-697.

Vorburger, S.A. et al. "Adenoviral Gene Therapy" *The Oncologist*, 2002, 7:46-59.

Wan, L.Q. et al. "Study of the uptake of chitosan oligosaccharide nanoparticles by A549 cells" *Yao Xue Xue Bao*, Mar. 2004, 39(3):277-231, abstract.

Witt, P.L. et al. "Isoforms p69 and p100 of 2',5'-Oligoadenylate Synthetase Induced Differentially by Interferons in Vivo and in Vitro" *Journal of Interferon Research*, 1993, 13:17-23.

Wright, P. et al. "Evaluation of a live, cold-passaged, temperature-sensitive, respiratory syncytial virus vaccine candidate in infancy" *J. Infect. Dis.*, 2000, 182:1331-1342.

Wyatt, L.S. et al. "Priming and boosting immunity to respiratory syncytial virus by recombinant replication-defective vaccinia virus MVA" *Vaccine*, 2000, 18:392-397.

Xiu, Q. et al. "Effect of intratracheally administered IL-12 recombinant adenovirus on ovalbumin induced bronchial hyresponsiveness in mouse model" *Chin J Tuberc Respir Dis*, 2001, 24:298-301, abstract.

Yoo, H.S. et al. "Self-assembled nanoparticles containing hydrophobically modified glycol chitosan for gene delivery" *Journal of Controlled Release*, 2005, 103:235-243.

Yoshida, M. et al. "Effect of interferon-γ on allergic airway responses in interferon-γ-deficient mice" *Am J Respir Crit Care Med*, 2002, 166:451-456.

Yu, F. et al. "Protein Kinase C Is Required for Induction of 2',5'-Oligoadenylate Synthetases" *Experimental Cell Research*, 1997, 234:240-248.

Zabner, J. et al. "Repeat Administration of an Adenovirus Vector Encoding Cystic Fibrosis Transmembrane Conductance Regulator to the Nasal Epithelium of Patients with Cystic Fibrosis" *J Clin Invest*, 1996, 97:1504-1511.

Zhu, Z. et al. "Acidic mammalian chitinase in asthmatic Th2 inflammation and IL-13 pathway activation" *Science*, 2004, 304:1678-1682.

Zoon, K.C. "Human interferons: Structure and function" *Interferon*, 1987, 9:1-12.

ATCC No. CCL-185, Designation: A549, deposited by Lieber, M., American Type Culture Collection (ATCC) Product Description from www.atcc.org accessed on Sep. 16, 2009, pp. 1-3.

Cincinnati Children's Hospital, "2006 Pediatric Health News Releases" http://www.cincinnatichildrens.org/about/news/release/2006/3-gene-therapy.htm, Mar. 31, 2006, 2 pages.

"Gene" from The American Heritage Dictionary of the English Language, 4th Ed. (online), 2000 (retrieved on Jun. 15, 2006). Retrieved from the Internet: <URL: http://dictionary.reference.com/browse/gene>, pp. 1-3.

"Gene Therapy" Wikipedia, http://en.wikipedia.org/wiki/Gene_therapy; accessed Nov. 16, 2007, pp. 1-12.

American Society of Gene Therapy, "Gene Therapy Defined" http://www.asgt.org/about_gene_therapy/defined.php, accessed Nov. 8, 2007, 1 page.

"Immunocytokines—Local Stimulation of the Immune System", 2002, www.merck.at/produkte/immunozytokine.pdf, pp. 1-2.

"Respiratory tract" from Wikipedia (online), 2006 (retrieved on Jun. 15, 2006). Retrieved from the Internet: <URL: http://en.wikipedia.org/wiki/Respiratory_tract>, pp. 1-2.

"Timolol Maleate" from RxList The Internet Drug Index (online), 2006 (retrieved on Jun. 15, 2006). Retrieved from the Internet: <URL: http://www.rxlist.com/cgi/generic3/timololgfs_wcp.htm>, pp. 1-4.

Adachi, Y. et al. "Amplitude and Frequency Modulation of Metabolic Signals in Leukocytes: Synergistic Role of IFN-γ in IL-6- and IL-2-Mediated Cell Activation" *The Journal of Immunology*, 1999, 163:4367-4374.

Addison, C.L. et al. "The CXC Chemokine, Monokine Induced by Interferon-γ, Inhibits Non-Small Cell Lung Carcinoma Tumor Growth and Metastasis" *Human Gene Therapy*, Jan. 20, 2000, 11:247-261.

Albelda, S.M. et al. "Gene Therapy for Lung Disease: Hype or Hope?" *Ann Intern Med*, 2000, 132:649-660.

Alroy, J. "Basophilic Leukemia in a Dog" *Vet Pathol*, 1972, 9:90-95.

Arenberg, D.A. et al. "Improved survival in tumor-bearing SCID mice treated with interferon-γ-inducible protein 10 (IP-10/CXCL10)" *Cancer Immunology, Immunotherapy*, 2001, 50:533-538.

Azimzadeh, Z. et al. "Xenograft rejection: molecular mechanisms and therapeutic prospects" *Hematology and Cell Therapy*, 1996, 38(4):331-343, 18 pages.

Barnes, P.J. et al. "Cytokine-directed therapies for asthma" *J Allergy Clin Immunol*, 2001, 108(2):S72-S76.

Behera, A.K. et al. "Mucosal 2'-5' Oligoadenylate Synthetase (2-5 AS) Gene Transfer Attenuates Respiratory Syncytial Virus Infection in a Murine Model" *J Allergy Clin Immunol*, Jan. 2002, 109(1):S43, abstract 79.

Bellon, G. et al. "Aerosol Administration of a Recombinant Adneovirus Expression CFTR to Cystic Fibrosis Patients: A Phase I Clinical Trial" *Human Gene Therapy*, Jan. 1, 1997, 8:15-25.

Bivas-Benita, M. et al. "Pulmonary delivery of chitosan-DNA nanoparticles enhances the immunogenicity of a DNA vaccine encoding HLA-A *0201-restricted T-cell epitopes of *Mycobacterium tuberculosis*" *Vaccine*, 2004, 22:1609-1615.

Boraschi, D. et al. "Interferons inhibit LTC4 production in murine macrophages" *The Journal of Immunology*, Jun. 15, 1987, 138:4341-4346.

Bradley, L.M. et al. "A Direct Role for IFN-gamma in Regulation of Th1 Cell Development" *The Journal of Immunology*, 1996, 157:1350-1580.

Byrnes, A.A. et al. "Type I interferons and IL-12: convergence and cross-regulation among mediators of cellular immunity" *Eur. J. Immunol.*, 2001, 31:2026-2034.

Carroll, M.W. et al. "Construction and Characterization of a Triple-Recombinant Vaccinia Virus Encoding B7-1, Interleukin 12, and a Model Tumor Antigen" *J Natl Cancer Inst*, 1998, 90:1881-1887.

Chada, S. et al. "Cytokine- and chemokine-based gene therapy for cancer" *Curr Opin Mol Ther.*, Oct. 2003, 5(5):463-474, abstract.

Chen, X.Q. et al. "Microsatellite alterations in plasma DNA of small cell lung cancer patients" *Nature Medicine*, Sep. 1996, 2(9):1033-1035.

Chen, Q. et al. "Development of Th-1-type immune responses requires the type I cytokine receptor TCCR" *Nature*, 2000, 407:916-920.

Chen, J.S. et al. "Cancer-specific activation of the survivin promoter and its potential use in gene therapy" *Cancer Gene Therapy*, 2004, 11:740-747.

Choudhary, S. et al. "Interferon Action against Human Parainfluenza Virus Type 3: Involvement of a Novel Antiviral Pathway in the Inhibition of Transcription" *Journal of Virology*, May 2001, 75(10):4823-4831.

Chung, F. "Anti-inflammatory cytokines in asthma and allergy: interleukin-10, interleukin-12, interferon-γ" Mediators of Inflammation, 2001, 10:51-59.

Chung, K.F. et al. "Cytokines in asthma" Thorax, Sep. 1999, 54:825-857.

Cohen, J. "IL-12 deaths: explanation and a puzzle" *Science*, 1995, 270:908.

Daines, M.O. and Hershey, G. "A novel mechanism by which interferon-γ can regulate interleukin (IL-13) responses" *J. Biol. Chem.*, 2002, 277(12):10387-10393.

Danielsen, S. et al. "Glycosaminoglycan destabilization of DNA-chitosan polyplexes for gene delivery depends on chitosan chain length and GAG properties" *Biochimica et Biophysica Acta*, 2005, 1721:44-54.

(56) References Cited

OTHER PUBLICATIONS

D'Cunha, J. et al. "In Vitro and in Vivo Secretion of Human ISG15, an IFN-Induced Immunomodulatory Cytokine" *The Journal of Immunology*, Nov. 1996, 157:4100-4108.

D'Cunha, J. et al. "Immunoregulatory properties of ISG15, an interferon-induced cytokine" *Proc. Natl. Acad. Sci. USA*, Jan. 1996, 93:211-215.

De Jong, R. et al. "IL-2 and IL-12 Act in Synergy to Overcome Antigen-Specific T Cell Unresponsiveness in Mycobacterial Disease" *The Journal of Immunology*, 1997, 159:786-793.

Demoly, P. et al. "Gene therapy strategies for asthma" *Gene Therapy*, 1997, 4:507-516.

Deng, J.C. et al. "Transient transgenic expression of gamma interferon promotes *Legionella pneumophila* clearance in immunocompetent hosts" *Infection and Immunity*, 2001, 69(10):6382-6390.

Dorsey, R. et al. "Immunotherapy with Interleukin-10 Depends on the CXC Chemokines Inducible Protein-10 and Monokine Induced by IFN-gamma" *Cancer Research*, May 2002, 62:2606-2610.

Elez, R. et al. "Tumor regression by combination antisense therapy against Plk1 and Bcl-2" *Oncogene*, 2003, 22:69-80.

Engelhardt, O.G. et al. "Interferon-Induced Antiviral Mx1 GTPase Is Associated with Components of the SUMO-1 System and Promyelocytic Leukemia Protein Nuclear Bodies" *Experimental Cell Research*, 2001, 271:286-295.

Eskildsen, S. et al. "Characterization of the 2'-5'-oligoadenylate synthetase ubiquitin-like family" *Nucleic Acids Research*, 2003, 31(12):3166-3173.

Fonseca, C. et al. "Paclitaxel-loaded PLGA nanoparticles: preparation, physicochemical characterization and in vitro anti-tumoral activity" *Journal of Controlled Release*, 2002, 83:273-286.

Ford, J.G. et al. "IL-13 and IFN-γ: interactions in lung inflammation" *J. Immunol.*, 2001, 167:1769-1777.

Gautam, A. et al. "Delivery systems for Pulmonary Gene Therapy" *Am J Respir Med*, 2002, 1(1):35-46.

Gavett, S.H. et al. "Interleukin 12 inhibits antigen-induced airway hyperresponsiveness, inflammation, and Th2 cytokine expression in mice" *J. Exp. Med.*, 1995, 182:1527-1536.

Genbank Accession No. AF101062 (Mar. 3, 1999), pp. 1-2.
Genbank Accession No. B38957 (Dec. 1, 2000), pp. 1-2.
Genbank Accession No. V00543 (Nov. 15, 1994) pp. 1-2.
Genbank Accession No. X13274 (Nov. 15, 1994), p. 1.

Ghosh, A. et al. "Enzymatic Activity of 2'-5'-Oligoadenylate Synthetase Is Impaired by Specific Mutations that Affect Oligomerization of the Protein" *The Journal of Biological Chemistry*, Dec. 26, 1997, 272(52):33220-33226.

Ghosh, A. et al. "Cell Growth Regulatory and Antiviral Effects of the P69 Isozyme of 2-5 (A) Synthetase" *Virology*, 2000, 266:319-328.

Gill, D.R. et al. "The development of gene therapy for diseases of the lung" *Cell. Mol. Life Sci.* 2004, 61(3):355-368.

Gould, D.S. et al. "Direct and indirect recognition: the role of MHC antigens in graft rejection" *Immunology Today*, Feb. 1999, 20(2):77-82.

Grohmann, U. et al. "Positive Regulatory Role of IL-12 in Macrophages and Modulation by IFN-γ" *The Journal of Immunology*, 2001, 167:221-227.

Guille, M.J. et al. "Functional differences in the promoters of the interferon-inducible (2'-5')A oligoadenylate synthetase and 6-16 genes in interferon-resistant Daudi Cells" *European Journal of Biochemistry*, Jan. 1994, 219:547-553.

Guo, W. et al. "siRNA-mediated MDM2 Inhibition sensitizes human lung cancer A549 cells to radiation" *International Journal of Oncology*, 2007, 30:1447-1452.

Gurujeyalakshmi, G. and Giri, S.N. "Molecular mechanisms of antifibrotic effect of interferon gamma in bleomycin-mouse model of lung fibrosis: downregulation of TGF-β and procollagen I and III gene expression" *Exp. Lung Res.*, 1995, 21:791-808.

Hansen, G. et al. "Allergen-specific Th1 cells fail to counterbalance Th2 cell-induced airway hyperreactivity but cause severe airway inflammation" *J. Clin. Invest.*, 1999, 103:175-183.

Hansen, G. et al. "CD4+T helper cells engineered to produce latent TGF-β1 reverse allergen-induced airway hyperreactivity and inflammation" *J. Clin. Invest.*, 2000, 105:61-70.

Hasbold, J. et al. "Integrating signals from IFN-γ and IL-4 by B cells: positive and negative effects on CD40 ligand-induced proliferation, survival, and division-linked isotype switching to IgG1, IgE, and IgG2a" *J. Immunol.*, 1999, 163:4175-4181.

Hasko, G. and Szabo, C. "IL-12 as a therapeutic target for pharmacological modulation in immune-mediated and inflammatory diseases: regulation of T helper 1/T helper 2 responses" *Brit. J. Pharm.*, 1999, 127:1295-1304.

He, T-C. et al. "A simplified system for generating recombinant adenoviruses" *Proc. Natl. Acad. Sci. USA*, 1998, 95:2509-2514.

Hertel, L. et al. "The retinoblastoma protein is an essential mediator that links the interferon-inducible 204 gene to cell-cycle regulation" *Oncogene*, Jul. 2000, 19(32):3598-3608.

Higgins, B. et al. "Antitumor activity of erlotinib (OSI-774, Tarceva) alone or in combination in human non-small cell lung cancer tumor xenograft models" *Anti-Cancer Drugs*, 2004, 15:503-512.

Hillinger, S. et al. "EBV-Induced Molecule 1 Ligand Chemokine (ELC/CCL19) Promotes IFN-gamma-Dependent Antitumor Responses in a Lung Cancer Model" *The Journal of Immunology*, 2003, 171:6457-6465.

Hirschowitz, E. et al. "Induction of cyclo-oxygenase-2 in non-small cell lung cancer cells by infection with ΔE1, ΔE3 recombinant adenovirus vectors" *Gene Therapy*, 2002, 9:81-84.

Hofstra, C. et al. "Differential effects of endogenous and exogenous interferon-γ on immunoglobulin E, cellular infiltration, and airway responsiveness in a murine model of allergic asthma" *Am. J. Respir. Cell Mol. Biol.*, 1998, 19:826-835.

Hogan, S.P. et al. "Mucosal IL-12 gene delivery inhibits allergic airways disease and restores local antiviral immunity" *European Journal of Immunology*, 1998, 28:413-423.

Huang, T.J. et al. "Inhibitory effects of endogenous and exogenous interferon-γ on bronchial hyperresponsiveness, allergic inflammation and T-helper 2 cytokines in Brown-Norway rats" *Immunology*, Oct. 1999, 98:280-288.

Huang, T-J. et al. "Allergen-specific Th1 cells counteract efferent Th2 cell-dependent bronchial hyperresponsiveness and eosinophilic inflammation partly via IFN-γ" *J. Immunol.*, 2001, 166:207-217.

Huang, H. et al. "Synergistic Effect of Lymphotactin and Interferon gamma-Inducible Protein-10 Transgene Expression in T-Cell Localization and Adoptive T-Cell Therapy of Tumors" *Int. J. Cancer*, 2004, 109:817-825.

Jakschies, D. et al. "Correlation of the Antiproliferative Effect and the Mx-Homologous Protein Induction by IFN in Patients with Malignant Melanoma" *J Invest Dermatol*, 1990, 95:238S-241S.

Jakschies, D. et al. "Emergence and decay of the human Mx homolog in cancer patients during and after interferon-alpha therapy" *J Biol Response Mod.*, Jun. 1990, 9(3):305-312, abstract.

Jooss, K. and Chirmule, N. "Immunity to adenovirus and adeno-associated viral vectors: implications for gene therapy" *Gene Therapy*, 2003, 10:955:963.

Jungwirth, C. et al. "Chicken interferon consensus sequence-binding protein (ICSBP) and interferon regulatory factor (IRF) 1 genes reveal evolutionary conservation in the IRF gene family" *Proc. Natl. Acad. Sci. USA*, Apr. 1995, 92:3105-3109.

Justesen, J. et al. "Gene structure and function of the 2'-5'-oligoadenylate synthetase family" *CMLS, Cellular and Molecular Life Sciences*, 2000, 57:1593-1612.

Justesen, J. et al. "Spectrophotometric Pyrophosphate Assay of 2',5'-Oligoadenylate Synthetase" *Analytical Biochemistry*, 1992, 207:90-93.

Kai, E. et al. "A Method for Oral DNA Delivery with N-Acetylated Chitosan" *Pharmaceutical Research*, May 2004, 21(5):838-843.

Kaplan, M.H. et al. "Impaired IL-12 responses and enhanced development of Th2 cells in Stat4-deficient mice" *Nature*, 1996, 382:174-177.

Kaplan, M.H. et al. "A signal transducer and activator of transcription (Stat)4-independent pathway for the development of T helper type 1 cells" *J. Exp. Med.*, 1998, 188(6):1191-1196.

(56) References Cited

OTHER PUBLICATIONS

Katakura, Y. et al. "Decreased Tumorigenicity in Vivo When Transforming Growth Factor β Treatment Causes Cancer Cell Senescence" Biosci Biotechnol Biochem, 2003, 67(4):815-821.

Kay, M.A. et al. "Viral vectors for gene therapy: the art of turning infectious agents into vehicles of therapeutics" Nature Med., 2001, 7:33-40.

Keyser, J. et al. "IP-10-encoding plasmid DNA therapy exhibits anti-tumor and anti-metastatic efficiency" Experimental Dermatology, 2004, 13:380-390.

Kim, J.S. et al. "Inhibition of Angiogenesis and Angiogenesis-dependent Tumor Growth by the Cryptic Kringle Fragments of Human Apolipoprotein(a)" The Journal of Biological Chemistry, Aug. 1, 2003, 278(31):29000-29008.

Kim, P.K.M. et al, "IRF-1 expression induces apoptosis and inhibits tumor growth in mouse mammary cancer cells in vitro and in vivo" Oncogene, 2004, 23:1125-1135.

Kirkwood, J.M. et al. "Interferon alfa-2b adjuvant therapy of high-risk resected cutaneous melanoma: The Eastern Cooperative Oncology Group trial EST 1684" J. Clin. Oncology, 1996, 14(1):7-17.

Kitagawa, M. et al. "Interferon-γ enhances interleukin 12 production in rheumatoid synovial cells via CD40-CD154 dependent and independent pathways" J. Rheumatology, 2001, 28:1764-1771.

Kraus-Berthier, L. et al. "Histology and Sensitivity to Anticancer Drugs of Two Human Non-Small Cell Lung Carcinomas Implanted in the Pleural Cavity of Nude Mice" Clinical Cancer Research, Jan. 2000, 6:297-304.

Kreiss, P. et al. "Plasmid DNA size does not affect the physicochemical properties of lipoplexes but modulates gene transfer efficiency" Nucleic Acids Research, 1999, 27(19):3792-3798.

Kumar, R. et al. "Growth inhibition of human acute promyelocytic leukemia NB-4 cells by interferons and all-trans retinoic acid: transmodulation of inducible gene expression pathways" Anticancer Research, Mar.-Apr. 1995, 15(2):353-360, abstract.

Kumar, M. et al. "IFN-γ and IL-12 plasmid DNAs as vaccine adjuvant in a murine model of grass allergy" J. Allergy Clin Immunol., Sep. 2001, 108:402-408.

Lack, G. et al. "Nebulized but not parenteral IFN-γ decreases IgE production and normalizes airways function in a murine model of allergen sensitization" J. Immunol., 1994, 152:2546-2554.

Liberati, A.M. et al. "Interferon-alpha-Induced Biologic Modifications in Patients with Chronic Myelogenous Leukemia" Journal of Interferon Research, Dec. 1994, 14:349-355.

Lighvani, A.A. et al. "T-bet is rapidly induced by interferon-γ in lymphoid and myeloid cells" PNAS, 2001, 98(26):15137-15142.

Lim, B.O. et al. "Dietary Fibers Modulate Indices of Intestinal Immune Functions in rats" J. Nutr., 1997, 127:663-667.

Luster, A.D. et al. "IP-10, a -C-X-C- Chemokine, Elicits a Potent Thymus-dependent Antitumor Response in Vivo" The Journal of Experimental Medicine, Sep. 1993, 178(3):1057-1065.

Maeda, Y. et al. "Antitumor Effects of Various Low-Molecular-Weight Chitosans Are Due to Increased Natural Killer Ability of Intestinal Intraepithelial Lymphocytes in Sarcoma 180-Bearing Mice" The Journal of Nutrition, 2004, 134:945-950.

Marshall, E. "Gene Therapy's Growing Pains" Science, 1995, 269:1050-1055.

Melaine, N. et al. "Production of the antiviral proteins 2'5'oligoadenylate synthetase, PKR and Mx in interstitial cells and spermatogonia" Journal of Reproductive Immunology, 2003, 59:53-60.

Minshall, E.M. et al. "Eosinophil-associated TGF-β1 mRNA expression and airways fibrosis in bronchial asthma" Am. J. Respir. Cell Mol. Biol., 1997, 17:326-333.

Miyamoto, M. et al. "Regulated Expression of a Gene Encoding a Nuclear Factor, IRF-1, That Specifically Binds to IFN-β Gene Regulatory Elements" Cell, Sep. 9, 1988, 54:903-913.

Mohapatra, S.M. et al., Poster materials presented at the American Academy of Allergy Asthma in Mar. 2002 and presented at the Immunology and American Thoracic Society in May 2002.

Morgan, R.A. et al. "Cancer Regression in Patients After Transfer of Genetically Engineered Lymphocytes" Science, Oct. 6, 2006, 314(5796):126-129.

Morrison, D.F. and Murtaugh, M.P. "Adenovirus-mediated expression of interleukin-1 receptor antagonist in swine cells in vitro and in vivo" Veterinary Immunol. and Immunopathology, 2001, 78:71-81.

Mosmann, T.R. and Coffman, R.L. "TH1 and TH2 cells: different patterns of lymphokine secretion lead to different functional properties" Ann. Rev. Immunol., 1989, 7:145-173.

Mullen, A.C. et al. "Role of T-bet in commitment of $T_H1$ cells before IL-12-dependent selection" Science, 2001, 292:1907-1909.

Nakahira, M. et al. "Synergy of IL-12 and IL-18 for IFN-γ Gene Expression: IL-12-Induced STAT4 Contributes to IFN-γ Promoter Activation by Up-Regulating the Binding Activity of IL-18-Induced Activator Protein 1" The Journal of Immunology, 2002, 168:1146-1153.

Naschberger, E. et al. "Human guanylate binding protein-1 (hGBP-1) characterizes and establishes a non-angiogenic endothelial cell activation phenotype in inflammatory diseases" Advances in Enzyme Regulation, 2005, 45:215-227.

University of South Florida, "Novel Gene Therapy Effectively Reduces Asthma Symptoms in Mice" released Oct. 31, 2003, 7:00 a.m., http://www.newswise.com/articles/view/501702/, pp. 1-2.

Nishiyama, Y. et al. "Regioselective Conjugation of Chitosan with a Laminin-related Peptide, Tyr-Ile-Gly-Ser-Arg, and Evaluation of Its Inhibitory Effect on Experimental Cancer Metastasis" Chem. Pharm. Bull., 1999, 47(3):451-453.

Nonaka, M. et al. "Induction of eotaxin production by interleukin-4, interleukin-13 and lipopolysaccharide by nasal fibroblasts" Clin. Exp. Allergy, 2004, 34:804-811.

O'Donnell, M.A. et al. "Role of IL-12 in the Induction and Potentiation of IFN-γ in Response to Bacillus Calmette-Guerin" The Journal of Immunology, 1999, 163:4246-4252.

O'Garra, A. and Arai, N. "The molecular basis of T helper 1 and T helper 2 cell differentiation" Cell Biol., 2000, 10:542-550.

Onari, Y. et al. "IL-12p40 is essential for the down-regulation of airway hyperresponsiveness in a mouse model of bronchial asthma with prolonged antigen exposure" Clinical and Experimental Allergy, 2009, 39:290-298.

Oppmann, B. et al. "Novel p19 protein engages IL-12p40 to form a cytokine, IL-23, with biological activities similar as well as distinct from IL-12" Immunity, 2000, 13:715-725.

Orkin, Report and recommendations of the panel to assess the NIH investment in research on gene therapy 1998, pp. 1-41.

Park, D.S. et al. "Induction of ICAM-DR Molecules by IFN-Gamma and Oncogene Expression in Human Bladder Cancer Cell Lines" Urologia Internationalis, 1997, 59(2):72-80, abstract, 2 pages.

Park, J.W. et al. "Primary Hepatocytes from Mice Treated with IL-2/IL-12 Produce T Cell Chemoattractant Activity that Is Dependent on Monokine Induced by IFN-gamma (Mig) and Chemokine Responsive to gamma-2 (Crg-2)" The Journal of Immunology, 2001, 166(6):3763-3770.

Park, K.H. et al. "Antiallergic Activity of a Disaccharide Isolated from Sanguisorba officinalis" Phytotherapy Research, 2004, 18:658-662.

Parmley, J.L. et al. "How do synonymous mutations affect fitness" BioEssays, 2007, 29:515-519.

Perricone, M.A. et al. "Aerosol and Lobar Administration of a Recombinant Adenovirus to Individuals with Cystic Fibrosis. II. Transfection Efficiency in Airway Epithelium" Human Gene Therapy, 2001, 12:1383-1394.

Pierkes, M. et al. "Decreases release of histamine and sulfidoleukotrienes by human peripheral blood leukocytes after wasp venom immunotherapy is partially due to induction of IL-10 and IFN-γ production of T cells" J. Allergy Clin. Immunol., 1999, 103:326-332.

Press Release "Introgen's Nanoparticle Cancer Therapy INGN 401 Demonstrates Promise in the Treatment of Lung Cancer" Orlando, FL, May 17, 2005, PRNewswire—FirstCall, http://www.prnewswire.com/cgi-bin/stories.pl?ACCT=104&STORY=/www/story/05-17-2005/0003633079&EDATE=.

(56) References Cited

OTHER PUBLICATIONS

Proesmans, M. et al. "What's new in cystic fibrosis? From treating symptoms to correction of the basic defect" *Eur J Pediatr*, 2008, 167:839-849.
Quintana, F.J. et al. "Vaccination with Empty Plasmid DNA or CpG Oligonucleotide Inhibits Diabetes in Nonobese Diabetic Mice: Modulation of Spontaneous 60-kDa Heat Shock Protein Autoimmunity" *The Journal of Immunology*, Dec. 2000, 165:6148-6155.
Ralph, S.J. et al. "Resistance of Melanoma Cell Lines to Interferons Correlates with Reduction of IFN-Induced Tyrosine Phosphorylation" *The Journal of Immunology*, 1995, 154:2248-2256.
Randolph, D.A. et al. "Modulation of airway inflammation by passive transfer of allergen-specific Th1 and Th2 cells in a mouse model of asthma" *J. Immunol.*, 1999, 162:2375-2383.
Robinson, D.S. et al. "Predominant $T_{H2}$-like bronchoalveolar T-lymphocyte population in atopic asthma" *N. Engl. J. Med.*, 1992, 326:298-304.
Rudick, R.A. et al. "Management of multiple sclerosis" *J. Engl. J. Med.*, 1997, 337(22):1604-1611.
Ruehlmann, J.M. et al. "*MIG* (CXCL9) Chemokine Gene Therapy Combines with Antibody-Cytokine Fusion Protein to Suppress Growth and Disseminiation of Murine Colon Carcinoma" *Cancer Research*, Dec. 2001, 61:8498-8503.
Sarkar, S.N. et al. "Identificationof the Substrate-binding Sites of 2'-5' Oligoadenylate Synthetase" *Journal of Biological Chemistry*, Jul. 5, 2002, 277(27):24321-24330.
Sarkar, S.N. et al. "Crisscross Enzymatic Reaction between the Two Molecules in the Active Dimeric P69 Form of the 2'-5' Oligodenylate Synthetase" *The Journal of Biological Chemistry*, Nov. 22, 2002, 277(47):44760-44754.
Saunders, N.A. et al. "Differential responsiveness of human bronchial epitlelial cells, lung carcinoma cells, and bronchial fibroblasts to interferon-gamma in vitro" *Am J Respir Cell Mol Biol.*, Aug. 1994, 11(2):147-152.
Scheerlinck, J-P. "Genetic adjuvants for DNA vaccines" *Vaccine*, 2001, 19:2647-2656.
Schroder, H.C. et al. "Protection of HeLa-T4+ cells against human immunodeficiency virus (HIV) infection after stable transfection with HIV LTR-2',5'-oligoadenylate synthetase hybrid gene" *FASEB Journal*, Oct. 1990, 4:3124-3130.
Schwarze, J. et al. "Local treatment with IL-12 is an effective inhibitor of airway hyperresponsiveness and lung eosinophilia after airway challenge in sensitized mice" *J. Allergy Clin. Immunol.*, 1998, 102:86-93.
Schwarze, J. et al. "Respiratory Syncytial Virus Infection Results in Airway Hyperresponsiveness and Enhanced Airway Sensitization to Allergen" *J Clin Invest*, 1997, 99:226-233.
Seo, W.G. et al. "Synergistic cooperation between water-soluble chitosan oligomers and interferon-gamma for induction of nitric oxide synthesis and tumoricidal activity in murine peritoneal macrophages" *Cancer Letters*, 2000, 159:189-195.
Sgadari, C. et al. "Interferon-inducible protein-10 identified as a mediator of tumor necrosis in vivo" *Proc. Natl. Acad. Sci. USA*, Nov. 1996, 93(24):13791-13796.
Sgadari, C. et al. "Mig, the Monokine Induced by Interferon-gamma, Promotes Tumor Necrosis in Vivo" *Blood*, Apr. 15, 1997, 89(8):2635-2643.
Sharma, S. et al. "SLC/CCL21-mediated anti-tumor responses require IFNgamma, MIG/CXCL9 and IP-10/CXCL10" *Molecular Cancer*, 2003, 2:22, pp. 1-6.
She, Y. et al. "The Epidermal Growth Factor Receptor Tyrosine Kinase Inhibitor ZD1839 Selectively Potentiates Radiation Response of Human Tumors in Nude Mice, with a Marked Improvement in Therapeutic Index" *Clinical Cancer Research*, Sep. 1, 2003, 9:3773-3778.
Shen, H. et al. "Paclitaxel-octreotide conjugates in tumor growth inhibition of A549 human non-small cell lung cancer xenografted into nude mice" *European Journal of Pharmacology*, 2008, 601:23-29.

Shindo-Okada, N. et al. "Establishment of Cell Lines with High and Low Metatstatic Potential from A549 Human Lung Adenocarcinoma" *Jpn J Cancer Res*, Jan. 2002, 93:50-60.
Smith, J.K. et al. "Oral Use of Interferon-alpha Stimulates ISG-15 Transcription and Production by Human Buccal Epithelial Cells" *Journal of Interferon and Cytokine Research*, 1999, 19:923-928.
Somia, N. and Verma, I.M. "Gene therapy: Trials and tribulations" *Nature Rev.*, 2000, 1:91-99.
Song, J.S. et al. "Enhanced Expression of Apoptin by the Myc-Max Binding Motif and SV40 Enhancer for SCLC Gene Therapy" *Biosci. Biotechnol. Biochem.*, 2005, 69(1):51-55.
Stabile, L.P. et al. "Inhibition of human non-small cell lung tumors by a c-Met antisense/U6 expression plasmid strategy" *Gene Therapy*, 2004, 11:325-335.
Stallmach, A. et al. "An Interleukin 12 p40-IgG2b Fusion Protein Abrogates T Cell Mediated Inflammation: Anti-Inflammatory Activity in Crohn's Disease and Experimental Colitis in Vivo", *Gut*, 2004, pp. 339-345, vol. 53.
Stampfli, M.R. et al. "GM-CSF transgene expression in the airway allows aerosolized ovalbumin to induce allergic sensitization in mice" *J. Clin. Invest.*, 1998, 102:1704-1714.
Stirling, R.G. and Chung, K.F. "New immunological approaches and cytokine targets in asthma and allergy" *Eur. Respir. J.*, 2000, 16:1158-1174.
Strieter, R.M. et al. "Interferon Gamma-Inducible Protein 10 (IP-10), a Member of the C-X-C Chemokine Family, Is an Inhibitor of Angiogenesis" *Biochemical and Biophysical Research Communications* May 1995, 210(1):51-57.
Sun, H. et al. "Interleukin-10 Gene Transfer Activates Interferon-gamma and the Interferon-gamma-Inducible Genes *Gbp-1/Mag-1* and *Mig-1* in Mammary Tumors" *International Journal of Cancer*, 1999, 80:624-629.
Sun, H. et al. "Expression of the Chemokines IP-10 and Mig in IL-10 Transduced Tumors" *Journal of Immunology*, Mar. 2001, 24(2):138-143.
Sur, S. et al. "Mucosal IL-12 inhibits airway reactivity to methacholine and respiratory failure in murine asthma" *Exp. Lung Res.*, 2000, 26:477-489.
Suzuki, M. et al. "Gene Therapy for Lung Diseases: Development in the Vector Biology and Novel Concepts for Gene Therapy Applications" Current Molecular Medicine, 2001, 1:67-79.
Swisher, S. et al. "p53 Gene Therapy for Lung Cancer" *Current Oncology Reports*, 2002, 4:334-340.
Tajima, K. et al. "Interferon-gamma Differentially Regulates Susceptibility of Lung Cancer Cells to Telomerase-Specific Cytotoxic T Lymphocytes" *Int J. Cancer*, 2004, 110:403-412.
Talpaz, M. et al. "Interferon-stimulated Genes in Interferon-sensitive and -resistant Chronic Myelogenous Leukemia Patients" *Cancer Research*, Mar. 1992, 52:1087-1090.
Tanaka, Y. et al. "Effects of chitin and chitosan particles on BALB/c mice by oral and parenteral administration" *Biomaterials*, 1997, 18:591-595.
Tang, C. et al. "Th type 1-stimulating activity of lung macrophages inhibits Th2-mediated allergic airway inflammation by an IFN-γ-dependent mechanism" *J. Immunol.*, 2001, 166:1471-1481.
Tannenbaum, C.S. et al. "The CXC Chemokines IP-10 and Mig Are Necessary for IL-12-Mediated Regression of the Mouse RENCA Tumor" *The Journal of Immunology*, 1998, 161:927-932.
Thierfelder, W.E. et al. "Requirement for Stat4 in interleukin-12-mediated responses of natural killer and T cells" *Nature*, 1996, 382:171-174.
Thivierge, M. et al. "IL-13 and IL-4 up-regulated cysteinyl leukotriene 1 receptor expression in human monocytes and macrophages" *J. Immunol.*, 2001, 167:2855-2860.
Trinchieri, G. "Interleukin-12: a cytokine produced by antigen-presenting cells with immunoregulatory functions in the generation of T-helper cells type 1 and cytotoxic lymphocytes" *Blood*, 1994, 84(12):4008-4027.
Ulitzur, N. et al. "Mapmodulin: A possible modulator of the interaction of microtubule-associated proteins with microtubules" *Proc. Natl. Acad. Sci. USA*, May 1997, 94:5084-5089.
Umetsu, D.T. and Dekruyff, R.H. "TH1 and TH2 CD4+ cells in human allergic diseases" *J. Allergy Clin. Immunol.*, 1997, 100(1):1-6.

(56) References Cited

OTHER PUBLICATIONS

Upton, C. et al. "Encoding of a homolog of the IFN-γ receptor by myxoma virus" *Science*, 1992, 258:1369-1372.

Van Den Hurk, S.V.D.L. et al. "Strategies for improved formulation and delivery of DNA vaccines to veterinary target species" *Immunological Reviews*, 2004, 199:113-125.

Vandenbroeck, K. et al. "The conserved helix C region in the superfamily of interferon-γ/interleukin-10-related cytokines corresponds to a high-affinity binding site for the HSP70 chaperone DnaK" *J. Biol. Chem.*, 2002, 277:25668-25676.

Verma, I.M. et al. "Gene Therapy—promises, problems and prospects" *Nature*, 1997, 389:239-242.

Villagomez, M.T. et al. "Tumour necrosis factor-alpha but not interferon-gamma is the main inducer of inducible protein-10 in skin fibroblasts frompatients with atopic dermatitis" *British Journal of Dermatology*, 2004, 150:910-916.

Wahren, B. et al. "DNA Vaccines: An Overview" in *DNA Pharmaceuticals: Formulation and Delivery in Gene Therapy, DNA Vaccination and Immunotherapy*, 2005, Wiley-VHC Verlag GmbH & Co, pp. 1-6.

Walter, D.M. et al. "IL-18 gene transfer by adenovirus prevents the development of and reverses established allergen-induced airway hyperreactivity" *J. Immunol.*, 2001, 166:6392-6398.

Wang, I-M. et al. "An IFN-γ-inducible transcription factor, IFN consensus sequence binding protein (ICSBP), stimulates IL-12 p40 expression in macrophages" *J. Immunol.*, 2000, 165:271-279.

Wang, Y.Q. "Expression of the Mig (CXCL9) gene in murine lung carcinoma cells generated angiogenesis-independent antitumor effects" *Oncology Reports*, Jul.-Aug. 2003, 10(4):909-913, abstract.

Wenner, C.A. et al. "Roles of IFN-gamma and IFN-alpha in IL-12-Induced T Helper Cell-1 Development" *The Journal of Immunology*, 1996, 156:1442-1447.

West, J. et al. "Gene Therapy for Pulmonary Diseases" Chest, Feb. 2001, 119:613-617.

Whitehead, C.M. et al. "Exisulind-induced Apoptosis in a Non-Small Cell Lung Cancer Orthotopic Lung Tumor Model Augments Docetaxel Treatment and Contributes to Increased Survival" Molecular Cancer Therapeutics, May 2003, 2:479-488.

Witzenrath, M. et al. "Detection of allergen-induced airway hyperresponsiveness in isolated mouse lungs" Am J Physiol Lung Cell Mol Physiol, 2006, 291:L466-L472.

Woolhiser, M.R. et al. "Immunological Responses of Mice following Administration of Natural Rubber Latex Proteins by Different Routes of Exposure" Toxicological Sciences, 2000, 55:343-351.

Yang, X. "Imaging of Vascular Gene Therapy" *RSNA*, 2003, 228(1):36-49.

Ye, J. et al. "Role of Reactive Oxygen Species and p53 in Chromium (VI)-induced Apoptosis" *The Journal of Biological Chemistry*, Dec. 3, 1999, 274(49):34974-34980.

Yu, L.G. et al. "Protein Phosphatase 2A, a Negative Regulator of the ERK Signaling Pathway, Is Activated by Tyrosine Phosphorylation of Putative HLA Class II-associated Protein I (PHAPI).pp32 in Response to the Antiproliferative Lectin, Jacalin" *The Journal of Biological Chemistry*, Oct. 2004, 279(40):41377-41383.

Yu-Lee, L.Y. et al. "Interferon-Regulatory Factor 1 Is an Immediate-Early Gene under Transcriptional Regulation by Prolactin in Nb2 T Cells" *Molecular and Cellular Biology*, Jun. 1990, 10(6):3087-3094.

Zhang, P. et al. "Gleevec (STI-571) inhibits lung cancer cell growth (A549) and potentiates the cisplatin effect in vitro" Molecular Cancer, Jan. 2003, 2:1-9.

Zhang, Y.A. et al. "Generation of a Ribozyme-Adenoviral Vector Against K-*ras* Mutant Human Lung Cancer Cells" *Molecular Biotechnology*, 2000, 15:39-49.

Alton, E. et al. "Gene therapy for asthma: inspired research or unnecessary effort?" Gene Therapy, 1999, 6:155-156.

Traversari C et al., "IFN-γ gene transfer restores HLA-class I expression and MAGE-3 antigen presentation to CTL in HLA-deficient small cell lung cancer" Gene Therapy, 1997, 4:1029-1035.

\* cited by examiner

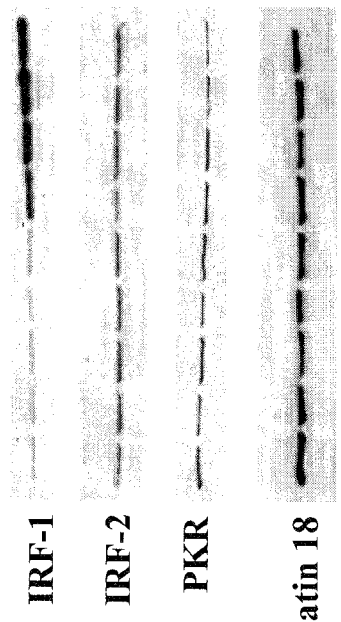
FIG. 5B
FIG. 5C
FIG. 5A

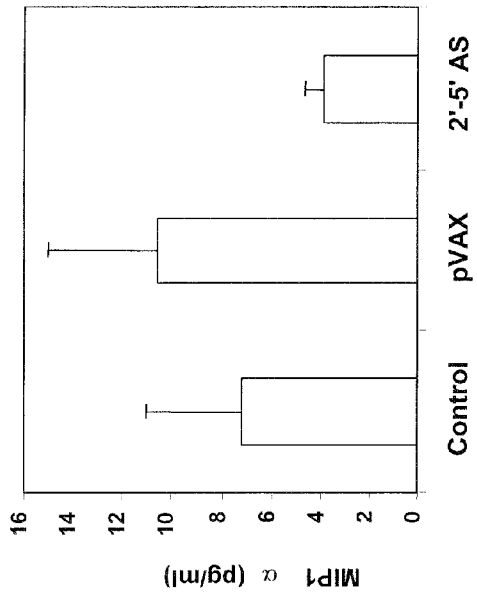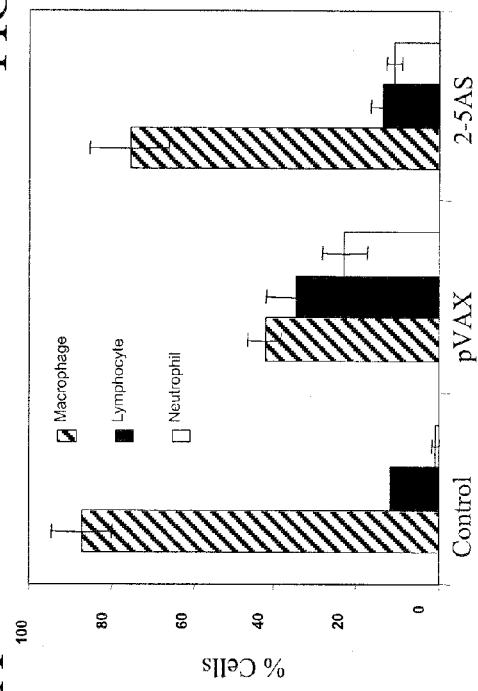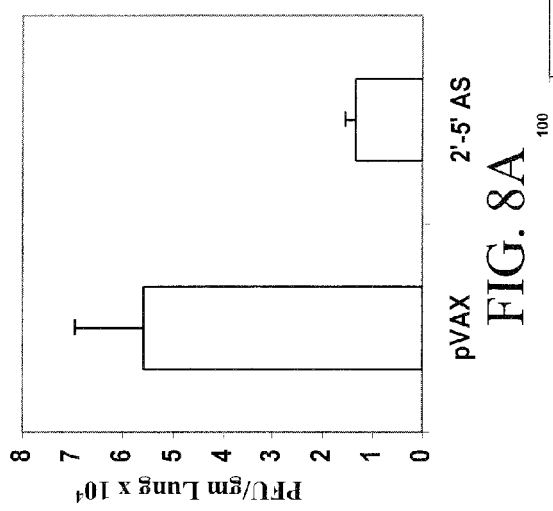
FIG. 8A
FIG. 8B
FIG. 8C

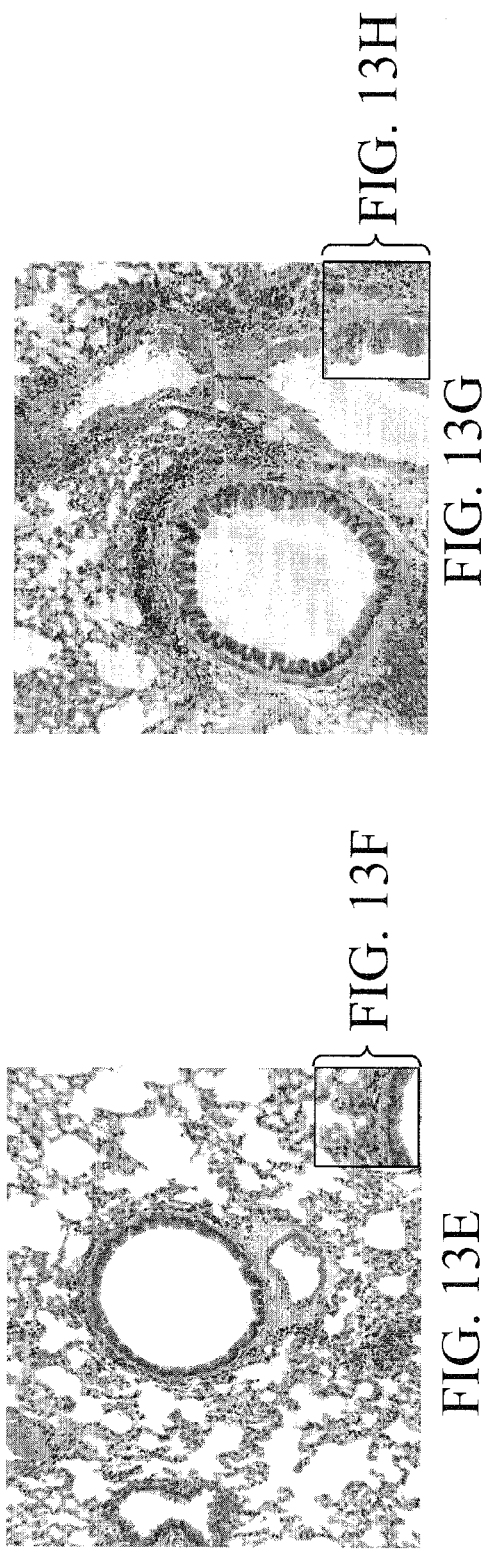

MATERIALS AND METHODS FOR PREVENTION AND TREATMENT OF RNA VIRAL DISEASES

CROSS-REFERENCE TO RELATED APPLICATIONS

The present application is a continuation of U.S. application Ser. No. 12/638,800, filed Dec. 15, 2009, which is a continuation of U.S. application Ser. No. 12/016,041, filed Jan. 17, 2008, which is a divisional of U.S. application Ser. No. 10/426,436, filed Apr. 30, 2003, now U.S. Pat. No. 7,354,908, which claims the benefit of provisional patent application Ser. No. 60/319,313, filed Jun. 12, 2002, and provisional patent application Ser. No. 60/319,216, filed Apr. 30, 2002, all of which are hereby incorporated by reference in their entirety, including all nucleic acid sequences, amino acid sequences, figures, tables, and drawings.

BACKGROUND OF INVENTION

Respiratory syncytial virus (RSV) is a major respiratory pathogen in infants, young children, and the elderly, causing severe bronchiolitis, pneumonia, and exacerbation of asthma. In the United States alone, RSV causes approximately 4 million cases of respiratory tract infection annually, which results in 149,000 hospitalizations and 11,000 deaths. It has been established that interferon-gamma (IFN-γ) gene therapy is effective against RSV infection in BALB/c mice (Kumar et al., Vaccine 18, 558-567, 1999).

Intranasal administration of a plasmid expressing IFN-γ cDNA proved to be an effective prophylaxis in mice. Furthermore, IFN-γ expressed by a recombinant respiratory syncytial virus attenuates virus replication in mice without compromising immunogenicity. IFN-γ, a type II interferon, is a pleotropic cytokine which plays an important role in modulating nearly all phases of immune and inflammatory responses. IFNs bind to specific receptors on cells and activate the JAK-STAT signaling cascade, which culminates in the transcriptional induction of IFN-stimulated genes (ISGs). The Jak1 and Jak2 phosphorylate STAT-1 following the binding of IFN-γ to its receptor. Once phosphorylated, STAT molecules dimerize and translocate to the nucleus and bind to gamma activated sequence (GAS) elements present in the regulatory regions of various ISGs. The antiviral mechanism of IFN-γ may involve one or more of a number of ISG-encoded products, including interferon regulatory factor-1 (IRF-1) double stranded RNA-dependent protein kinase (PKR), the Mx family of proteins, a family of 2'-5'-oligoadenylate synthetases (2-5 AS), and RNase L.

RNase L is constitutively expressed in most mammalian cells and is found in an inactive form bound to RNase L inhibitor (RLI), a 68 kDa protein not regulated by IFN-γ. The 2-5 AS produces a series of 5' phosphorylated, 2', and 5'-linked oligoadenylates (2-5 A) from ATP, when activated by double-stranded ribonucleic acid (dsRNA). Upon binding of 2-5 AS with RNase L, RLI is released and consequently, RNase L is dimerized and activated, mediating the cleavage of single-stranded RNA. However, the mechanism of the induction and activation of each of these genes is different in different cells and for the types of viruses. The mechanism of the IFN-γ-mediated anti-viral activity remains to be elucidated for many clinically important viruses.

BRIEF SUMMARY OF THE INVENTION

The present invention provides materials and methods useful for inhibiting viral infections caused by ribonucleic acid (RNA) viruses that transiently produce double-stranded RNA during replication. The subject invention concerns therapeutic methods for preventing or decreasing the severity of symptoms associated with an RNA viral infection by increasing endogenous levels of 2'-5' oligoadenylate synthetase (2-5 AS) activity within the patient. Preferably, the endogenous levels of the 2-5 AS p40 subunit (e.g., the 40 kDa, 42 kDa, 46 kDa, or other splice variants), p69 subunit, (e.g., the 69 kDa, 71 kDa, or other splice variants), p100 subunit, or combinations thereof, are increased within the patient.

The materials and methods of present invention are effective for treating or preventing human or animal infections from RNA viruses such as, members of the family paramyxoviridae, respiratory syncytial virus (RSV), Rhinovirus, Vaccinia, Reovirus, human immunodeficiency virus (HIV), encephalomyocarditis virus (EMCV), Hepatitis B, Hepatitis C, as well as bovine respiratory syncytial virus (BRSV), which infect cattle, sheep, and goats; Measles virus; Sendai virus; Parainfluenza 1, 2, and 3; Mumps virus, Simian virus; and Newcastle virus.

In one aspect, the method of the present invention involves the administration of a nucleotide sequence encoding 2-5 AS, or at least one catalytically active fragment of 2-5 AS, such as the p40, p69, or p100 subunits of 2-5 AS, to a patient in need thereof. The nucleotide sequence encoding 2-5 AS or at least one catalytically active fragment thereof can be administered to the patient, for example, in a viral vector or non-viral vector, such as plasmid deoxyribonucleic acid (DNA). In cases wherein the RNA virus is one which infects the patient's respiratory system, the nucleotide sequence encoding 2-5 AS, or at least one catalytically active fragment thereof, is preferably administered orally or intranasally to the epithelial mucosa of the respiratory system.

The present invention also pertains to pharmaceutical compositions comprising a nucleotide sequence encoding 2-5 AS, or at least one catalytically active fragment thereof, such as the p40, p69, or p100 subunits of 2-5 AS, and a pharmaceutically acceptable carrier. The pharmaceutical compositions of the present invention are useful for preventing or decreasing the severity of symptoms associated with RNA viral infections. In another embodiment, the pharmaceutical compositions of the present invention comprise the 2-5 AS polypeptide, or at least one catalytically active fragment of the 2-5 AS polypeptide, and a pharmaceutically acceptable carrier. The pharmaceutical compositions of the present invention can include various agents that protect the nucleic acid or amino acid contents from protein degradation.

In another aspect, the present invention concerns vectors containing a nucleotide sequence encoding 2-5 AS, or at least one catalytically active fragment thereof, such as the p40, p69, or p100 subunits of 2-5 AS. Optionally, the vector can further include a promoter sequence operatively linked to the nucleotide encoding 2-5 AS or at least one catalytically active fragment thereof, permitting expression of the nucleotide sequence within a host cell. In another aspect, the present invention includes host cells that have been genetically modified with a nucleotide sequence encoding 2-5 AS, or at least one catalytically active fragment thereof, such as the p40, p69, or p100 subunits of 2-5 AS.

BRIEF DESCRIPTION OF DRAWINGS

FIG. 3 show results of northern analysis performed using gene specific probes for IRF-1 and the p40 and p69 isoforms of 2-5 AS.

FIGS. 5A-D show the results of northern analyses of (i) RNAs from RNAse L inhibitor (RLI) and HEp-2 using a gene specific probe for RLI and (ii) the level of mRNA expression of IRF-1, p40, and p69 isoforms of 2-5 AS.

FIGS. 8A-8C show lung titers of RSV in infected mice following 2-5 AS cDNA vaccination. BALB/c mice (n=4) were intranasally administered with p2'-5' AS (25 mg of DNA each time complexed with lipofectamine) or an equal amount of empty pVAX (CLONTECH, Palo Alto, Calif., USA) vector DNA (as a transfection control) 3 times in 2 day intervals. As shown in FIG. 8A, 2-5 AS cDNA vaccination significantly attenuated lung titers of RSV. FIG. 8B shows that vaccination with 2-5 AS cDNA decreases production of the chemokine macrophage inflammatory protein-1 alpha (MIP-1 α). The results of bronchoalveolar lavage (BAL) cell differential (FIG. 8C) show that 2-5 AS does not significantly alter the cellular composition of the lung, although the percent of neutrophils is increased in the lungs of mice treated with 2-5 AS cDNA.

FIG. 9A is an untreated control. FIGS. 9B and 9C show histological sections of RSV infected lungs following treatment with the empty pVAX vector and p2'-5' AS, respectively.

FIGS. 13A-13H show that Ad-p40 overexpression normalizes macrophage and lymphocyte numbers in the lung in RSV infected mice. BAL cell differential was performed and percentages of macrophage, lymphocytes and neutrophils was determined. Both Ad-IFNg and Ad-p40 treatment reduced the lymphocyte population to normal, compared to RSV-infected mice. Histological sections from lungs were stained with hematoxylin and eosin and representative photomicrographs are shown. Sections shown are as follows: Naive mice (FIG. 13A; with magnified inset FIG. 13B); RSV infected mice (FIG. 13C; with magnified inset, FIG. 13D); Ad-p40 treated mice (FIG. 13E; with magnified inset, FIG. 13F); and Ad-lacZ treated mice (FIG. 13G; with magnified inset, FIG. 13H).

BRIEF DESCRIPTION OF SEQUENCES

Figure 1B:
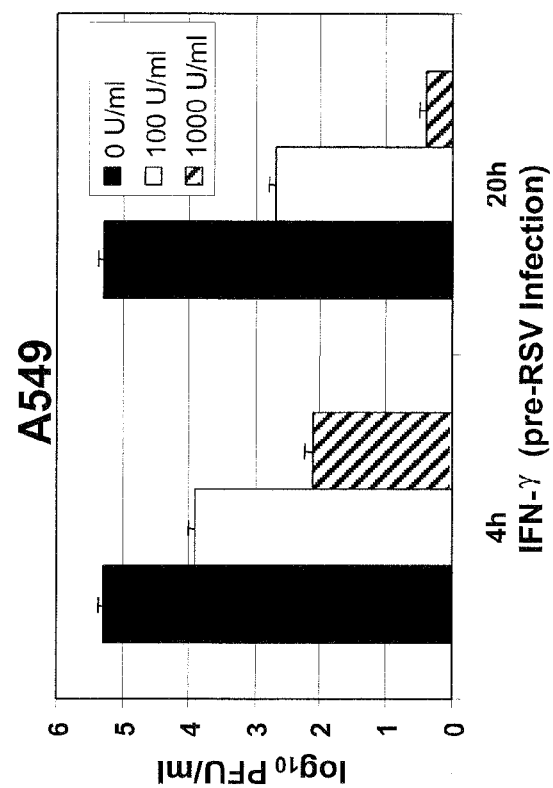
FIGS. 1A-D show the results of pre-incubation of HEp-2 cells for 4-20 hours with different concentrations of IFN-γ and subsequent infection with RSV.

SEQ ID NO: 1 is a nucleotide coding sequence (CDS) for the human 40 kDa splice variant of the 40/46 kDa subunit ("p40 subunit") of 2'-5' oligoadenylate synthetase (National Center for Biotechnology Information (NCBI) Accession Number NM_016816).

SEQ ID NO: 2 is an amino acid sequence of the human 40 kDa splice variant of the 40/46 kDa subunit ("p40 subunit") of 2'-5' oligoadenylate synthetase (NCBI Accession Number NM_016816).

SEQ ID NO: 3 is a nucleotide coding sequence (CDS) for the human 46 kDA splice variant of the 40/46 kDa subunit ("p40 subunit") of 2'-5' oligoadenylate synthetase (National Center for Biotechnology Information (NCBI) Accession Number NM_016816).

SEQ ID NO: 4 is an amino acid sequence of the human 46 kDA splice variant of the 40/46 kDa subunit ("p40 subunit") of 2'-5' oligoadenylate synthetase (NCBI Accession Number NM_016816).

SEQ ID NO: 5 is a nucleotide coding sequence (CDS) for the human 69 kDA splice variant of the 69/71 kDa subunit ("p69 subunit") of 2'-5' oligoadenylate synthetase (NCBI Accession Number NM_002535).

SEQ ID NO: 6 is an amino acid sequence of the human 69 kDa splice variant of the 69/71 kDa subunit ("p69 subunit") of 2'-5' oligoadenylate synthetase (NCBI Accession Number NM_002535).

SEQ ID NO: 7 is a nucleotide coding sequence (CDS) for the human 71 kDA splice variant of the 69/71 kDa subunit ("p69 subunit") of 2'-5' oligoadenylate synthetase (NCBI Accession Number NM_002535).

SEQ ID NO: 8 is an amino acid sequence of the human 71 kDa splice variant of the 69/71 kDa subunit ("p69 subunit") of 2'-5' oligoadenylate synthetase (NCBI Accession Number NM_002535).

SEQ ID NO: 9 is a nucleotide coding sequence (CDS) for the human 100 kDa subunit ("p100 subunit") of 2'-5' oligoadenylate synthetase (NCBI Accession Number AF063613).

SEQ ID NO: 10 is an amino acid sequence of the human 100 kDa subunit ("p100 subunit") of 2'-5' oligoadenylate synthetase (NCBI Accession Number AF063613).

SEQ ID NO: 11 is a nucleotide coding sequence (CDS) for the mouse homolog of the 2'-5' oligoadenylate synthetase 40 kDa splice variant (p40 subunit) (NCBI Accession Number M33863).

SEQ ID NO: 12 is the amino acid sequence for the mouse homolog of the 2'-5' oligoadenylate synthetase 40 kDa splice variant (p40 subunit) (NCBI Accession Number M33863).

SEQ ID NO: 13 is the human 2'-5' oligoadenylate synthetase 40/46 kDa (p40 subunit) gene (NCBI Accession Number NM_016816).

SEQ ID NO: 14 is the human 2'-5' oligoadenylate synthetase 69/71 kDa (p69 subunit) gene (NCBI Accession Number NM_002535).

SEQ ID NO: 15 is the human 2'-5' oligoadenylate synthetase 100 kDa (p100 subunit) gene (NCBI Accession Number AF063613).

SEQ ID NO: 16 is the mouse homolog of the 2'-5' oligoadenylate synthetase 40 kDa (p40 subunit) gene (NCBI Accession Number M33863).

SEQ ID NO: 17 is a phosphorothioate antisense oligonucleotide (ODN) designed against the p40 subunit of 2'-5' oligoadenylate synthetase.

SEQ ID NO: 18 is an ODN designed against the p69 subunit of 2'-5' oligoadenylate synthetase.

SEQ ID NO: 19 is a scramble of the antisense sequence to p40, i.e., identical in base composition.

SEQ ID NO: 20 is a scramble of the antisense sequence to p69.

DETAILED DISCLOSURE OF THE INVENTION

The subject invention concerns a method of inhibiting an RNA virus infection within a patient by increasing the endogenous levels of 2-5 oligoadenylate synthetase (2-5 AS) activity within the patient. Preferably, the endogenous levels of the 2-5 AS p40 subunit (e.g., 40 kDa, 42 kDA, 46 kDa, or other splice variant), p69 subunit (e.g., 69 kDa, 71 kDa, or other splice variant), p100 subunit, or combinations thereof, are increased within the patient.

The present inventors have determined that overexpression of the 2-5 AS, or catalytically active fragments thereof, causes a reduction in epithelial cell damage, reduction in infiltration of mononuclear cells in the peribronchiolar and perivascular regions, and reduction in the thickening of the septa in the lungs of patients suffering from respiratory RNA viruses, such as respiratory syncytial virus (RSV). Levels of chemokines, such as MIP1-α, are also reduced upon overexpression of 2-5 AS.

Infections from members of the family paramyxoviridae that produce double-stranded RNA as a requirement of replication can be prevented or treated using the present invention. Thus, infections by members of the genera paramyxovirus, morbillivirus, rubulavirus, pnuemovirus, and others can be inhibited in humans and animals. Examples of RNA viruses that produce double-stranded RNA during intermediate replication and which infect humans include, but are not limited to, respiratory syncytial virus (RSV), Rhinovirus, Vaccinia, Reovirus, HIV, EMCV, Hepatitis B, and Hepatitis C. Examples of RNA viruses that infect animals and produce double-stranded RNA during intermediate replication include, but are not limited to, bovine respiratory syncytial virus (BRSV), which infect cattle, sheep, and goats; Measles virus; Sendai virus; Parainfluenza 1, 2, and 3; Mumps virus; Simian virus; and Newcastle virus. Infections caused by coronavirus (such as that responsible for severe acute respiratory syndrome (SARS)), rotavirus, parainfluenza virus, West Nile virus, as well as other viruses in which interferon actively inhibits viral replication can be inhibited using the methods and compositions of the present invention.

In one aspect, the subject invention concerns a method of treating or preventing an RNA virus infection within a patient by increasing the in vivo concentration of 2-5 AS or a catalytically active fragment thereof within the patient, thereby inhibiting the RNA virus infection. Preferably, the methods of the present invention do not involve administration of interferon or a polynucleotide encoding interferon, such as interferon-alpha (IFN-α), interferon-beta (IFN-β), or interferon-gamma (IFN-γ), or the administration of such IFN polypeptides. Thus, the methods and compositions of the present invention are directed to increasing the in vivo concentration of 2-5 AS or a catalytically active fragment thereof, which is an IFN-γ-induced downstream molecule. Advantageously, the methods and compositions of the present invention exhibit an antiviral effect without the adverse effects associated with IFN-γ.

The in vivo concentration of the 2-5 AS, or a catalytically active fragment thereof, can be increased, for example, by exogenous administration of the 2-5 AS polypeptide, or a catalytically active fragment of the polypeptide. Preferably, the in vivo concentration of the 2-5 AS polypeptide or catalytically active fragment is increased by increasing or up-regulating the functional expression of the nucleotide sequence encoding 2-5 AS or at least one catalytically active fragment thereof, such as the p40, p69, or p100 subunits, as gene therapy. More preferably, a nucleotide sequence encoding 2-5 AS or at least one catalytically active fragment thereof can be administered to a patient and expressed in order to increase the endogenous level of 2-5 AS enzymatic activity within the patient. For example, at least one nucleotide sequence selected from the group consisting of SEQ ID NOs: 1, 3, 5, 7, 9, 11, 13, 14, 15, 16, and 17, or a catalytically active fragment thereof, can be administered to the patient. The nucleotide sequence can be administered to a patient's cells in vivo or in vitro (including ex vivo, genetically modifying the patient's own cells ex vivo and subsequently administering the modified cells back into the patient).

In another aspect of the invention, 2-5 AS polypeptide, or at least one catalytically active fragment thereof, is administered to a patient in order to increase the antiviral function of 2-5 AS within the patient. Preferably, the polypeptides utilized are those disclosed herein. The polypeptides can comprise catalytically active fragments of the full-length 2-5 AS amino acid sequence, such as the p40, p69, or p100 subunits, including splice variants of these subunits, or mammalian homologs of these subunits (e.g., the p46 isoform of OAS-1; accession number NP_058132.1), such as murine homologs. For example, the polypeptides can comprise one or more amino acid sequences set forth herein as SEQ ID NOs: 2, 4, 6, 8, 10, 12, 13, 14, 15 or 16, or catalytically active fragments of these amino acid sequences.

Various means for delivering polypeptides to a cell can be utilized to carry out the methods of the subject invention. For example, protein transduction domains (PTDs) can be fused to the polypeptide, producing a fusion polypeptide, in which the PTDs are capable of transducing the polypeptide cargo across the plasma membrane (Wadia, J. S, and Dowdy, S. F., *Curr. Opin. Biotechnol.*, 2002, 13 (1)52-56). Examples of PTDs include the *Drosophila* homeotic transcription protein antennapedia (Antp), the herpes simplex virus structural protein VP22, and the human immuno-deficiency virus 1 (HIV-1) transcriptional activator Tat protein.

According to the method of RNA virus inhibition of the subject invention, recombinant cells can be administered to a patient, wherein the recombinant cells have been genetically modified to express the gene encoding 2-5 AS or at least one catalytically active fragment thereof, such as the p40, p69, or p100 subunits of 2-5 AS. If the cells to be genetically modified already express a gene encoding 2-5 AS, the genetic modification can serve to enhance or increase expression of the gene encoding 2-5 AS or a catalytically active fragment of 2-5 AS beyond the normal or constitutive amount (e.g., "overexpression").

The method of RNA virus inhibition of the subject invention can be used to treat a patient suffering from an RNA virus infection, or as a preventative of RNA virus infection (i.e., prophylactic treatment). According to the methods of the subject invention, various other compounds, such as antiviral compounds, can be administered in conjunction with (before, during, or after) increasing the in vivo concentrations of 2-5 AS or at least one catalytically active fragment within the patient. Various compositions and methods for preventing or treating RNA virus infection can be used in conjunction with the compositions and methods of the subject invention, such as those described in U.S. Pat. No. 6,489,306, filed Feb. 23, 1999, and U.S. published patent application Serial No. 2003/00068333, filed Feb. 12, 2002, which are incorporated herein by reference in their entirety. For example, nucleotide sequences encoding 2-5 AS or at least one catalytically active fragment thereof can be conjugated with chitosan, a biodegradable, human-friendly cationic polymer that increases mucosal absorption of the gene expression vaccine without any adverse effects, as described in U.S. published patent application Serial No. 2003/00068333.

The nucleotide sequence can be formulated in the form of nanospheres with chitosan. Chitosan allows increased bioavailability of the DNA because of protection from degradation by serum nucleases in the matrix and thus has great potential as a mucosal gene delivery system, for example. Chitosan exhibits various beneficial effects, such as anticoagulant activity, wound-healing properties, and immunostimulatory activity, and is capable of modulating immunity of the mucosa and bronchus-associated lymphoid tissue.

Nucleotide, polynucleotide, or nucleic acid sequences(s) are understood to mean, according to the present invention, either a double-stranded DNA, a single-stranded DNA, products of transcription of the said DNAs (e.g., RNA molecules), or corresponding RNA molecules that are not products of transcription. It should also be understood that the present invention does not relate to the genomic nucleotide sequences encoding 2-5 AS or catalytically active fragments thereof in their natural/native environment or natural/native state. The nucleic acid, polynucleotide, or nucleotide sequences of the invention have been isolated, purified (or partially purified), by separation methods including, but not limited to, ion-exchange chromatography, molecular size exclusion chromatography, affinity chromatography, or by genetic engineering methods such as amplification, cloning or subcloning.

Optionally, the polynucleotide sequence encoding 2-5 AS or catalytically active fragment thereof can also contain one or more polynucleotides encoding heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental Biology* 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A*. 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol*. 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B. V.; Smith [1998] "Cookbook for Eukaryotic Protein Expression: Yeast, Insect, and Plant Expression Systems," The Scientist 12 (22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11 (17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or INVITROGEN (San Diego, Calif.).

Other aspects of the invention provide vectors containing one or more of the polynucleotides of the invention, such as vectors containing nucleotides encoding 2-5 AS or catalytically active fragments of 2-5 AS, such as the p40 and/or p69 subunits. The vectors can be vaccine, replication, or amplification vectors. In some embodiments of this aspect of the invention, the polynucleotides are operably associated with regulatory elements capable of causing the expression of the polynucleotide sequences. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, lentiviruses, fowl pox viruses, pseudorabies viruses and retroviruses, and vectors derived from combinations of the aforementioned vector sources, such as those derived from plasmid and bacteriophage genetic elements (e.g., cosmids and phagemids). Preferably, the vector is an adenoviral vector or adeno-associated virus vector.

As indicated above, vectors of this invention can also comprise elements necessary to provide for the expression and/or the secretion of 2-5 AS, or a catalytically active fragment thereof, encoded by the nucleotide sequences of the invention in a given host cell. The vector can contain one or more elements selected from the group consisting of a promoter sequence, signals for initiation of translation, signals for termination of translation, and appropriate regions for regulation of transcription. In certain embodiments, the vectors can be stably maintained in the host cell and can, optionally, contain signal sequences directing the secretion of translated protein. Other embodiments provide vectors that are not stable in transformed host cells. Vectors can integrate into the host genome or be autonomously-replicating vectors.

In a specific embodiment, a vector comprises a promoter operably linked to a 2-5 AS-encoding nucleic acid sequence (or a catalytically active fragment thereof), one or more origins of replication, and, optionally, one or more selectable markers (e.g., an antibiotic resistance gene). Non-limiting exemplary vectors for the expression of the polypeptides of the invention include pBr-type vectors, pET-type plasmid vectors (PROMEGA), pBAD plasmid vectors (INVITROGEN), and pVAX plasmid vectors (INVITROGEN), or others provided in the examples below. Furthermore, vectors according to the invention are useful for transforming host cells for the cloning or expression of the nucleotide sequences of the invention.

Promoters which may be used to control expression include, but are not limited to, the CMV promoter, the SV40 early promoter region (Bernoist and Chambon [1981] *Nature* 290:304-310), the promoter contained in the 3' long terminal repeat of Rous sarcoma virus (Yamamoto, et al. [1980] *Cell*

22:787-797), the herpes thymidine kinase promoter (Wagner et al. [1981] *Proc. Natl. Acad. Sci. USA* 78:1441-1445), the regulatory sequences of the metallothionein gene (Brinster et al. [1982] *Nature* 296:39-42); prokaryotic vectors containing promoters such as the β-lactamase promoter (Villa-Kamaroff, et al. [1978] *Proc. Natl. Acad. Sci. USA* 75:3727-3731), or the tac promoter (DeBoer, et al. [1983] *Proc. Natl. Acad. Sci. USA* 80:21-25); the lung specific promoters such as surfactant protein B promoter (Venkatesh et al., *Am. J. Physiol.* 268 (*Lung Cell Mol. Physiol.* 12):L674-L682, 1995); see also, "Useful Proteins from Recombinant Bacteria" in *Scientific American*, 1980, 242:74-94; plant expression vectors comprising the nopaline synthetase promoter region (Herrera-Estrella et al. [1983] *Nature* 303:209-213) or the cauliflower mosaic virus 35S RNA promoter (Gardner, et al. [1981] *Nucl. Acids Res.* 9:2871), and the promoter of the photosynthetic enzyme ribulose biphosphate carboxylase (Herrera-Estrella et al. [1984] *Nature* 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The subject invention also provides for "homologous" or "modified" nucleotide sequences. Modified nucleic acid sequences will be understood to mean any nucleotide sequence obtained by mutagenesis according to techniques well known to persons skilled in the art, and exhibiting modifications in relation to the normal sequences. For example, mutations in the regulatory and/or promoter sequences for the expression of a polypeptide that result in a modification of the level of expression of a polypeptide according to the invention provide for a "modified nucleotide sequence". Likewise, substitutions, deletions, or additions of nucleic acid to the polynucleotides of the invention provide for "homologous" or "modified" nucleotide sequences. In various embodiments, "homologous" or "modified" nucleic acid sequences have substantially the same biological activity as the native (naturally occurring) 2-5 AS or subunit thereof. A "homologous" or "modified" nucleotide sequence will also be understood to mean a subunit or a splice variant of the polynucleotides of the instant invention or any nucleotide sequence encoding a "modified polypeptide" as defined below.

A homologous nucleotide sequence, for the purposes of the present invention, encompasses a nucleotide sequence having a percentage identity with the bases of the nucleotide sequences of between at least (or at least about) 20.00% to 99.99% (inclusive), and which encodes a catalytically active polypeptide. The aforementioned range of percent identity is to be taken as including, and providing written description and support for, any fractional percentage, in intervals of 0.01%, between 20.00% and 99.99%. These percentages are purely statistical and differences between two nucleic acid sequences can be distributed randomly and over the entire sequence length.

In various embodiments, homologous sequences exhibiting a percentage identity with the bases of the nucleotide sequences of the present invention can have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polynucleotide sequences of the instant invention.

Both protein and nucleic acid sequence homologies may be evaluated using any of the variety of sequence comparison algorithms and programs known in the art. Such algorithms and programs include, but are by no means limited to, TBLASTN, BLASTP, FASTA, TFASTA, and CLUSTALW (Pearson and Lipman [1988] *Proc. Natl. Acad. Sci. USA* 85 (8):2444-2448; Altschul et al. [1990] *J. Mol. Biol.* 215 (3): 403-410; Thompson et al. [1994] *Nucleic Acids Res.* 22 (2): 4673-4680; Higgins et al. [1996] *Methods Enzymol.* 266:383-402; Altschul et al. [1990] *J. Mol. Biol.* 215 (3):403-410; Altschul et al. [1993] *Nature Genetics* 3:266-272).

Nucleotide sequences encoding polypeptides with enhanced 2-5 AS catalytic activity can be obtained by "gene shuffling" (also referred to as "directed evolution", and "directed mutagenesis"), and used in the compositions and methods of the present invention. Gene shuffling is a process of randomly recombining different sequences of functional genes (recombining favorable mutations in a random fashion) (U.S. Pat. Nos. 5,605,793; 5,811,238; 5,830,721; and 5,837, 458). Thus, protein engineering can be accomplished by gene shuffling, random complex permutation sampling, or by rational design based on three-dimensional structure and classical protein chemistry (Cramer et al., *Nature*, 391:288-291, 1998; and Wulff et al., *The Plant Cell*, 13:255-272, 2001).

The subject invention also provides nucleotide sequences complementary to any of the polynucleotide sequences disclosed herein. Thus, the invention is understood to include any DNA whose nucleotides are complementary to those of 2-5 AS polynucleotide sequence of the invention, or catalytically active fragments thereof, and whose orientation is reversed (e.g., an antisense sequence).

The present invention further provides catalytically active fragments of the 2-5 AS polynucleotide sequences, including catalytically active fragments of the 2-5 AS subunit nucleotide sequences, provided herein. Representative fragments of the polynucleotide sequences according to the invention will be understood to mean any nucleotide fragment having at least 8 or 9 successive nucleotides, preferably at least 12 successive nucleotides, and still more preferably at least 15 or at least 20 successive nucleotides of the sequence from which it is derived. The upper limit for such fragments is the total number of polynucleotides found in the full-length sequence (or, in certain embodiments, of the full length open reading frame (ORF) identified herein). It is understood that, optionally, such fragments refer only to portions of the disclosed polynucleotide sequences that are not listed in a publicly available database or prior art references. However, it should be understood that with respect to the method for inhibiting RSV of the subject invention, disclosed nucleotides (and polypeptides encoded by such nucleotides) that are listed in a publicly available database or prior art reference can also be utilized. For example, nucleotide sequences that are 2-5 AS p40 or p69 subunit homologs, or fragments thereof, which have been previously identified, can be utilized to carry out the method for inhibiting RNA virus infection of the subject invention.

In other embodiments, fragments contain from one nucleotide less than the full length 2-5 AS enzyme, or from one nucleotide less than a catalytically active subunit thereof, such as p40 or p69 subunit polynucleotide CDS sequences (e.g., 1,203 and 1,207 nucleotides for the 40 kDa splice variant and 46 kDa splice variant, respectively; and 2063 and 2,168 nucleotides for the 69 kDa splice variant and 71 kDa splice variant, respectively) to fragments containing the smallest number of nucleotides encoding a polypeptide that retains at least some 2-5 AS enzymatic activity.

Among these representative fragments, those capable of hybridizing under stringent conditions with a nucleotide sequence encoding 2-5 AS or subunits thereof are preferred. Conditions of high or intermediate stringency are provided infra and are chosen to allow for hybridization between two complementary DNA fragments. Hybridization conditions for a polynucleotide of about 1,000 to 3,000 bases in size will be adapted by persons skilled in the art for larger- or smaller-sized oligonucleotides, according to methods well known in the art (see, for example, Sambrook et al. [1989] *Molecular Cloning, A Laboratory Manual, Second Edition*, Cold Spring Harbor Press, N.Y., pp. 9.47-9.57).

The subject invention also provides detection probes (e.g., fragments of the disclosed polynucleotide sequences) for hybridization with a target sequence or an amplicon generated from the target sequence. Such a detection probe will advantageously have as sequence a sequence of at least 9, 12, 15, 20, 25, 30, 35, 40, 45, 50, 55, 60, 65, 70, 75, 80, 85, 90, 95, or 100 nucleotides. Alternatively, detection probes can comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127 and up to, for example, 1,203 consecutive nucleotides, 1,207 consecutive nucleotides, 2,064 consecutive nucleotides, 2,186 consecutive nucleotides, 3,264 consecutive nucleotides, and 1,104 consecutive nucleotides of those disclosed herein, which correspond, respectively, to the human 40 kDa splice variant of the 2-5 AS p40 subunit (SEQ ID NO:1), human 46 kDa splice variant 2-5 AS p40 subunit (SEQ ID NO:3), human 69 kDa splice variant of the 2-5 AS p69 subunit (SEQ ID NO:5), human 71 kDa splice variant of the 2-5 AS p69 subunit (SEQ ID NO:7), human p100 subunit (SEQ ID NO:9), and the mouse homolog of the 2-5 AS p40 subunit (SEQ ID NO: 11). The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

The nucleotide sequences according to the invention may also be used in analytical systems, such as DNA chips. DNA chips and their uses are well known in the art and (see for example, U.S. Pat. Nos. 5,561,071; 5,753,439; 6,214,545; Schena et al. [1996] *BioEssays* 18:427-431; Bianchi et al. [1997] *Clin. Diagn. Virol.* 8:199-208; each of which is hereby incorporated by reference in their entireties) and/or are provided by commercial vendors such as AFFYMETRIX, Inc. (Santa Clara, Calif.).

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] *DNA Probes*, Stockton Press, New York, N.Y., pp. 169-170.

By way of example, hybridization of immobilized DNA on Southern blots with $^{32}P$-labeled gene-specific probes can be performed by standard methods (Maniatis et al. [1982] *Molecular Cloning: A Laboratory Manual*, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. [1983] *Methods of Enzymology*, R. Wu, L. Grossman and K. Moldave [eds.] Academic Press, New York 100:266-285).

$$T_m = 81.5° C. + 16.6 \text{ Log } [Na+] + 0.41(\% G+C) - 0.61(\% \text{ formamide}) - 600/\text{length of duplex in base pairs}.$$

Washes are typically carried out as follows:
(1) twice at room temperature for 15 minutes in 1×SSPE, 0.1% SDS (low stringency wash);
(2) once at $T_m$-20EC for 15 minutes in 0.2×SSPE, 0.1% SDS (moderate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$$T_m(° C.) = 2(\text{number } T/A \text{ base pairs}) + 4(\text{number } G/C \text{ base pairs}) \text{ (Suggs et al. [1981] } ICN\text{-}UCLA \text{ Symp. Dev. Biol. Using Purified Genes}, \text{D. D. Brown [ed.], Academic Press, New York, 23:683-693).}$$

Washes can be carried out as follows:
(1) twice at room temperature for 15 minutes 1×SSPE, 0.1% SDS (low stringency wash;
2) once at the hybridization temperature for 15 minutes in 1×SSPE, 0.1% SDS (moderate stringency wash).

In general, salt and/or temperature can be altered to change stringency. With a labeled DNA fragment>70 or so bases in length, the following conditions can be used:
Low: 1 or 2×SSPE, room temperature
Low: 1 or 2×SSPE, 42° C.
Moderate: 0.2× or 1×SSPE, 65° C.
High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C., the preferred hybridization temperature, in pre-hybridization mixture containing 100 g/ml denatured salmon sperm DNA and 5-20×10$^6$ cpm of $^{32}P$-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art (see, for example, Sambrook et al. [1989] *Molecular Cloning, A Laboratory Manual, Second Edition*, Cold Spring Harbor Press, N.Y., pp. 9.47-9.57; and Ausubel et al. [1989] *Current Pro-* tocols in Molecular Biology, Green Publishing Associates and Wiley Interscience, N.Y., each incorporated herein in its entirety).

A further non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filter washes are performed in a solution containing 2×SSC at 50° C. and the hybridized probes are detectable by autoradiography. Other conditions of intermediate stringency which may be used are well known in the art (see, for example, Sambrook et al. [1989] Molecular Cloning, A Laboratory Manual, Second Edition, Cold Spring Harbor Press, N.Y., pp. 9.47-9.57; and Ausubel et al. [1989] Current Protocols in Molecular Biology, Green Publishing Associates and Wiley Interscience, N.Y., each of which is incorporated herein in its entirety).

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] Molecular Cloning: A Laboratory Manual, Cold Spring Harbor Laboratory, New York; Wei et al. [1983] J. Biol. Chem. 258:13006-13512. The nucleic acid sequences of the subject invention can also be used as molecular weight markers in nucleic acid analysis procedures.

The invention also provides host cells transformed by a polynucleotide according to the invention and the production of 2-5 AS or a catalytically active fragment thereof, by the transformed host cells. In some embodiments, transformed cells comprise an expression vector containing 2-5 AS nucleotide sequences or a catalytically active fragment thereof. Other embodiments provide for host cells transformed with nucleic acids. Yet other embodiments provide transformed cells comprising an expression vector containing fragments of 2-5 AS p40 and/or p69 subunit nucleotide sequences. Transformed host cells according to the invention are cultured under conditions allowing the replication and/or the expression of the 2-5 AS nucleotide sequence or a catalytically active fragment thereof, such as the p40 and/or p69 subunits. Expressed polypeptides are recovered from culture media and purified, for further use, according to methods known in the art.

The host cell may be chosen from eukaryotic or prokaryotic systems, for example bacterial cells (Gram negative or Gram positive), yeast cells, animal cells, human cells, plant cells, and/or insect cells using baculovirus vectors. In some embodiments, the host cell for expression of the polypeptides include, and are not limited to, those taught in U.S. Pat. Nos. 6,319,691; 6,277,375; 5,643,570; 5,565,335; Unger [1997] The Scientist 11 (17):20; or Smith [1998] The Scientist 12(22):20, each of which is incorporated by reference in its entirety, including all references cited within each respective patent or reference. Other exemplary, and non-limiting, host cells include Staphylococcus spp., Enterococcus spp., E. coli, and Bacillus subtilis; fungal cells, such as Streptomyces spp., Aspergillus spp., S. cerevisiae, Schizosaccharomyces pombe, Pichia pastoris, Hansela polymorpha, Kluveromyces lactis, and Yarrowia lipolytica; insect cells such as Drosophila S2 and Spodoptera Sf9 cells; animal cells such as CHO, COS, HeLa, C127, 3T3, BHK, 293 and Bowes melanoma cells; and plant cells. A great variety of expression systems can be used to produce the 2-5 AS polypeptides or catalytically active fragments thereof and encoding polynucleotides can be modified according to methods known in the art to provide optimal codon usage for expression in a particular expression system.

Furthermore, a host cell strain may be chosen that modulates the expression of the inserted sequences, modifies the gene product, and/or processes the gene product in the specific fashion. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product whereas expression in yeast will produce a glycosylated product. Expression in mammalian cells can be used to provide "native" glycosylation of a heterologous protein. Furthermore, different vector/host expression systems may effect processing reactions to different extents.

Nucleic acids and/or vectors encoding 2-5 AS, or catalytically active fragments thereof, such as the p40 and/or p69 subunits, can be introduced into host cells by well-known methods, such as, calcium phosphate transfection, DEAE-dextran mediated transfection, transfection, microinjection, cationic lipid-mediated transfection, electroporation, transduction, scrape loading, ballistic introduction and infection (see, for example, Sambrook et al. [1989] Molecular Cloning: A Laboratory Manual, 2$^{nd}$ Ed., Cold Spring Harbor Laboratory Press, Cold Spring Harbor, N.Y.).

The subject invention also provides for the expression of the 2-5 AS p40 or p69 subunit, derivative, or an analogue (e.g., a splice variant) encoded by a polynucleotide sequence disclosed herein. Alternatively, the invention provides for the expression of a polynucleotide encoding a fragment of a 2-5 AS p40 or p69 subunit. In either embodiment, the disclosed sequences can be regulated by a second nucleic acid sequence so that the polypeptide or fragment is expressed in a host transformed with a recombinant DNA molecule according to the subject invention. For example, expression of a protein or peptide may be controlled by any promoter/enhancer element known in the art.

In the context of the instant invention, the terms polypeptide, peptide and protein are used interchangeably. Likewise, the terms analogue and homologous are also used interchangeably. It should be understood that the invention does not relate to the polypeptides in natural form or native environment. Peptides and polypeptides according to the invention have been isolated or obtained by purification from natural sources (or their native environment), chemically synthesized, or obtained from host cells prepared by genetic manipulation (e.g., the polypeptides, or fragments thereof, are recombinantly produced by host cells). Polypeptides according to the instant invention may also contain non-natural amino acids, as will be described below.

"Analogues" or "homologous" polypeptides will be understood to designate the polypeptides containing, in relation to the native polypeptide, modifications such as deletion, addition, or substitution of at least one amino acid, truncation, extension, or the addition of chimeric heterologous polypeptides. Optionally, "analogues" or "homologous" polypeptides can contain a mutation or post-translational modifications. Among the "analogues" or "homologous" polypeptides, those whose amino acid sequence exhibits 20.00% to 99.99% (inclusive) identity to the native polypeptide sequence are preferred. The aforementioned range of percent identity is to be taken as including, and providing written description and support for, any fractional percentage, in intervals of 0.01%, between 50.00% and, up to, including 99.99%. These percentages are purely statistical and differences between two polypeptide sequences can be distributed randomly and over the entire sequence length.

"Analogues" or "homologous" polypeptide sequences exhibiting a percentage identity with the human 2-5 AS polypeptides, or subunits thereof, can alternatively have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides and as provided below.

By way of example, amino acid substitutions can be carried out without resulting in a substantial modification of the biological activity of the corresponding modified polypeptides; for example, the replacement of leucine with valine or isoleucine; aspartic acid with glutamic acid; glutamine with asparagine; arginine with lysine; and the reverse substitutions can be performed without substantial modification of the biological activity of the polypeptides.

The subject invention also provides catalytically active fragments of the 2-5 AS polypeptide, and catalytically active fragments of the 2-5 AS subunits, according to the invention, which are capable of eliciting an immune response against RSV. The immune response can provide components (either antibodies or components of the cellular immune response (e.g., B-cells, helper, cytotoxic, and/or suppressor T-cells) reactive with the catalytically active fragment of the polypeptide, the intact, full length, unmodified polypeptide, or both the catalytically active fragment of the polypeptide and the intact, full length, unmodified polypeptides.

Catalytically active fragments according to the invention can comprise from five (5) amino acids to one amino acid less than the full length of any polypeptide sequence provided herein. For example, fragments comprising 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, and up to one amino acid less than the full length amino acid sequence of SEQ ID NO:2, SEQ ID NO:4, SEQ ID NO:6, SEQ ID NO:8, SEQ ID NO:10, and SEQ ID NO:12, are provided herein.

Fragments, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Such polypeptide fragments may be equally well prepared by chemical synthesis or using hosts transformed with an expression vector containing nucleic acids encoding polypeptide fragments according to the invention. The transformed host cells contain a nucleic acid and are cultured according to well-known methods; thus, the invention allows for the expression of these fragments, under the control of appropriate elements for regulation and/or expression of the polypeptide fragments.

Modified polypeptides according to the invention are understood to designate a polypeptide obtained by variation in the splicing of transcriptional products of the 2-5 AS gene, genetic recombination, or by chemical synthesis as described below. Modified polypeptides contain at least one modification in relation to the normal polypeptide sequence. These modifications can include the addition, substitution, or deletion of amino acids contained within the polypeptides of the invention.

Conservative substitutions whereby an amino acid of one class is replaced with another amino acid of the same type fall within the scope of the subject invention so long as the substitution does not materially alter the biological activity of the polypeptide. For example, the class of nonpolar amino acids include Ala, Val, Leu, Ile, Pro, Met, Phe, and Trp; the class of uncharged polar amino acids includes Gly, Ser, Thr, Cys, Tyr, Asn, and Gln; the class of acidic amino acids includes Asp and Glu; and the class of basic amino acids includes Lys, Arg, and His. In some instances, non-conservative substitutions can be made where these substitutions do not significantly detract from the biological activity of the polypeptide.

In order to extend the life of the polypeptides of the invention, it may be advantageous to use non-natural amino acids, for example in the D form, or alternatively amino acid analogs, such as sulfur-containing forms of amino acids. Alternative means for increasing the life of polypeptides can also be used in the practice of the instant invention. For example, polypeptides of the invention, and fragments thereof, can be recombinantly modified to include elements that increase the plasma, or serum half-life of the polypeptides of the invention. These elements include, and are not limited to, antibody constant regions (see for example, U.S. Pat. No. 5,565,335, hereby incorporated by reference in its entirety, including all references cited therein), or other elements such as those disclosed in U.S. Pat. No. 6,319,691; 6,277,375; or 5,643,570, each of which is incorporated by reference in its entirety, including all references cited within each respective patent. Alternatively, the 2-5 AS polynucleotides, or catalytically active fragments thereof, used in the instant invention can be recombinantly fused to elements that are useful in the preparation of immunogenic constructs for the purposes of vaccine formulation or elements useful for the isolation of the polypeptides of the invention.

The polypeptides, fragments, and immunogenic fragments of the invention may further contain linkers that facilitate the attachment of the fragments to a carrier molecule for delivery or diagnostic purposes. The linkers can also be used to attach fragments according to the invention to solid support matrices for use in affinity purification protocols. In this aspect of the invention, the linkers specifically exclude, and are not to be considered anticipated, where the fragment is a subsequence of another peptide, polypeptide, or protein as identified in a search of protein sequence databases as indicated in the preceding paragraph. In other words, the non-identical portions of the other peptide, polypeptide, or protein is not considered to be a "linker" in this aspect of the invention. Non-limiting examples of "linkers" suitable for the practice of the invention include chemical linkers (such as those sold by Pierce, Rockford, Ill.), peptides that allow for the connection of the immunogenic fragment to a carrier molecule (see, for example, linkers disclosed in U.S. Pat. Nos. 6,121,424; 5,843,464; 5,750,352; and 5,990,275, hereby incorporated by reference in their entirety). In various embodiments, the linkers can be up to 50 amino acids in length, up to 40 amino acids in length, up to 30 amino acids in length, up to 20 amino acids in length, up to 10 amino acids in length, or up to 5 amino acids in length.

In other specific embodiments, the 2-5 AS polypeptide or 2-5 AS subunit polypeptide, peptides, derivatives, or analogs thereof may be expressed as a fusion, or chimeric protein product (comprising the protein, fragment, analog, or derivative joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia Coli*," *J. of Experimental Biology* 203:19-28, The Co. of Biologists, Ltd., G. B.; Baneyx [1999] "Recombinant Protein Expression in *Escherichia coli*," *Biotechnology* 10:411-21, Elsevier Science Ltd.; Eihauer et al. [2001] "The FLAG Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995]"Current Trends in Molecular Recognition and Bioseparation," *J. Chromatography A.* 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990]"Engineering Proteins for Purification," *TibTech* 8:88-93; Sheibani [1999] "Prokaryotic Gene Fusion Expression Systems and Their Use in Structural and Functional Studies of Proteins," *Prep. Biochem. & Biotechnol.* 29 (1):77-90, Marcel Dekker, Inc.; Skerra et al. [1999]"Applications of a Peptide Ligand for Streptavidin: The Strep-tag", *Biomolecular Engineering* 16:79-86, Elsevier Science, B. V.; Smith [1998] "Cookbook for Eukaryotic Protein Expression Yeast, Insect, and Plant Expression Systems," *The Scientist* 12(22):20; Smyth et al. [2000] "Eukaryotic Expression and Purification of Recombinant Extracellular Matrix Proteins Carrying the Strep II Tag", *Methods in Molecular Biology,* 139:49-57; Unger [1997] "Show Me the Money: Prokaryotic Expression Vectors and Purification Systems," *The Scientist* 11 (17):20, each of which is hereby incorporated by reference in their entireties). Alternatively, such a chimeric product may be made by protein synthetic techniques, e.g., by use of a peptide synthesizer. Fusion peptides can comprise polypeptides of the subject invention and one or more protein transduction domains, as described above. Such fusion peptides are particularly useful for delivering the cargo polypeptide through the cell membrane.

Increasing the amount of 2-5 AS enzymatic activity (e.g., p40, p69, and/or p100 subunit activity) within a tissue is useful in preventing an RNA virus infection, or in treating an existing RNA virus infection. Thus, according to the methods of the subject invention, the amount of 2-5 AS activity can be increased within a tissue by directly administering the 2-5 AS polypeptide or a catalytically active fragment thereof to a patient suffering from or susceptible to an RNA virus infection (such as exogenous delivery of the 2-5 AS p40, p69, and/or p100 subunit polypeptide) or by indirect or genetic means (such as delivery of a nucleotide sequence encoding the 2-5 AS polypeptide or a catalytically active fragment thereof, or upregulating the endogenous 2-5 AS polypeptide activity).

As used herein, the term "administration" or "administering" refers to the process of delivering an agent to a patient, wherein the agent directly or indirectly increases 2-5 AS enzymatic function within the patient and, preferably, at the target site. The process of administration can be varied, depending on the agent, or agents, and the desired effect. Thus, wherein the agent is genetic material, such as DNA, the process of administration involves administering a DNA encoding 2-5 AS, or a catalytically active fragment thereof, to a patient in need of such treatment. Administration can be accomplished by any means appropriate for the therapeutic agent, for example, by parenteral, mucosal, pulmonary, topical, catheter-based, or oral means of delivery. Parenteral delivery can include for example, subcutaneous intravenous, intramuscular, intra-arterial, and injection into the tissue of an organ, particularly tumor tissue. Mucosal delivery can include, for example, intranasal delivery. According to the method of the present invention, a nucleotide sequence encoding the 2-5 AS or catalytically active fragment is preferably administered into the airways of a patient, i.e., nose, sinus, throat, lung, for example, as nose drops, by nebulization, vaporization, or other methods known in the art. Oral or intranasal delivery can include the administration of a propellant. Pulmonary delivery can include inhalation of the agent. Catheter-based delivery can include delivery by iontropheretic catheter-based delivery. Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid. Gene therapy protocol is also considered an administration in which the therapeutic agent is a polynucleotide capable of accomplishing a therapeutic goal when expressed as a transcript or a polypeptide into the patient. Further information concerning applicable gene therapy protocols is provided in the examples disclosed herein.

The pharmaceutical compositions of the subject invention can be formulated according to known methods for preparing pharmaceutically useful compositions. Formulations are described in a number of sources which are well known and readily available to those skilled in the art. For example, *Remington's Pharmaceutical Science* (Martin E W [1995] Easton Pennsylavania, Mack Publishing Company, $19^{th}$ ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Therapeutically effective and optimal dosage ranges for 2-5 AS or catalytically active fragments thereof can be determined using methods known in the art. Guidance as to appropriate dosages to achieve an anti-viral effect is provided from the exemplified assays disclosed herein.

As used herein, the term "catalytic activity" with respect to fragments, analogues, and homologs of the 2-5 AS polypeptide, or to fragments, analogues, and homologues of nucleotide sequences encoding the 2-5 AS polypeptide, refers to 2'-5' oligoadenylate synthetase activity. As used herein, "2'-5' oligoadenylate synthetase activity" refers to polymerization of ATP to produce 2'-5' linked oligoadenylates, which in turn, activate a latent ribonuclease, RNase L, that degrades RNAs (see, for example, Katze et al., *Nat. Rev. Immunol.*, September 2002, 2 (9):675-687; Justesen et al., *Cell Mol. Life. Sci.*, 57:1593-1612, 2000; Hartmann et al., *J. Bio. Chem.*, 273(6): 3236-3246, 1998; U.S. Pat. No. 5,766,864). Preferably, the catalytic activity is an amount effective to inhibit RNA virus infection (pre-infection or post-infection). 2'-5' oligoadenylate synthetase activity can be determined directly or indirectly in vivo, or in vitro, using methods known in the art. Thus, cell-based assays can be utilized to determine whether an agent, such as a nucleotide sequence or polypeptide, exhibits the relevant catalytic activity, and can be utilized to carry out the method of RNA virus inhibition of the subject invention.

RNA virus infections that can be inhibited using the present invention include those that must produce double-stranded RNA as an intermediate step in viral replication and those viruses for which interferon can actively inhibit viral replication. These RNA viruses can included single-stranded or double-stranded RNA viruses, and have genomes of positive (+) or negative (−) strand polarity.

The present invention further provides methods of making the host cells, pharmaceutical compositions, and vectors described herein by combining the various components using methods known in the art.

The term "patient", as used herein, refers to any vertebrate species. Preferably, the patient is of a mammalian species. Mammalian species which benefit from the disclosed methods of treatment include, and are not limited to, apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Human or non-human animal patients can range in age from neonates to elderly. The nucleotide sequences and polypeptides can be administered to patients of the same species or from different species. For example, mammalian, homologs can be administered to human patients.

The terms "2-5 AS p40 subunit" and "2-5 AS p40 subunit polypeptide" are used herein interchangeably to refer to the 2'-5' oligoadenylate synthetase p40 subunit gene or its coding sequence (CDS), its polypeptide product, or a catalytically active fragment or analogue of the polypeptide product, and includes 2-5 AS p40 subunit peptide homologs (such as mammalian orthologs (e.g., SEQ ID NOs: 11 and 12); NCBI Accession Number M33863) and isoforms, unless otherwise noted. Thus, the term includes all splice variants of the p40 subunit, such as the 40 kDa (SEQ ID NOs: 1 and 2), 42 kDa, and 46 kDa (SEQ ID NOs:3 and 4) splice variants of the 2-5 AS p40 subunit (NCBI Accession Number NM_016816).

The terms "2-5 AS p69 subunit" and "2-5 AS p69 subunit polypeptide" are used herein interchangeably to refer to the 2'-5' oligoadenylate synthetase p69 subunit gene or its coding sequence (CDS), its polypeptide product, or a catalytically active fragment or analogue of the polypeptide product, and includes 2-5 AS p69 subunit peptide homologs (such as mammalian orthologs) and isoforms, unless otherwise noted. Thus, the term includes all splice variants of the p69 subunit, such as the 69 kDa (SEQ ID NOs:5 and 6) and 71 kDa (SEQ ID NOs:7 and 8) splice variants of the 2-5 AS p69 subunit (NCBI Accession Number NM_002535).

The terms "2-5 AS p100 subunit" and "2-5 AS p100 subunit polypeptide" are used herein interchangeably to refer to the 2'-5' oligoadenylate synthetase p100 subunit gene or its coding sequence (CDS) (SEQ ID NO:9), its polypeptide product (SEQ ID NO:10), or a catalytically active fragment or analogue of the polypeptide product, and includes 2-5 AS p100 subunit peptide homologs (such as mammalian orthologs) and isoforms, unless otherwise noted. Thus, the term includes all splice variants of the p100 subunit (NCBI Accession Number AF063613).

The terms "comprising", "consisting of", and "consisting essentially of" are defined according to their standard meaning and may be substituted for one another throughout the instant application in order to attach the specific meaning associated with each term.

Materials and Methods

Epithelial Cell Culture, Virus Infection and Plaque Assay. The HEp-2 (ATCC CCL-23) cell line was obtained from the American Type Culture Collection (Manassas, Va.) and was maintained in Minimum Essential medium with Hank's salts (MEM) supplemented with 5% fetal bovine serum (FBS) (ATLANTA BIOLOGICALS, Norcross, Ga.) at 37° C. with 5% $CO_2$. Respiratory syncytial virus (RSV) A2 strain was obtained from ATCC (VR-1302) and was propagated in HEp-2 cells grown in MEM with 2% FBS on a monolayer culture. Viral stocks were prepared from infected HEp-2 cells 5 days post infection (p.i.), stored at −70° C. in aliquots and used as the viral inoculum. RSV titers were quantified by plaque assay as described earlier (21).

MTT Cytotoxicity Assay. The effect of IFN-γ on the viability of cells was determined using a MTT [3-(4,5-dimethylthiazol-2-yl)-2,5-diphenyltetrazolium bromide] (SIGMA, St. Louis, Mo.) cytotoxicity assay. Triplicate sets of cell monolayers were used for each IFN-γ dose tested and for each time point. In this system, the mitochondrial dehydrogenase enzymes of living cells cleave the tetrazolium ring of the yellow MTT to form purple formazan crystals, which are insoluble in aqueous solutions. The crystals were dissolved in acidified isopropanol, and the absorbance of the resulting purple solution was spectrophotometrically measured at 540 nm. An increase or decrease in the viable cell number results in a concomitant change in the amount of formazan formed, indicating the degree of cytotoxicity caused by the indicated dose of IFN-γ.

Immunoblot Analysis. IFN-γ treated cells were washed in cold PBS, pH 7.4 and scraped into PBS at various time points. The cells were collected by centrifugation at 6000 rpm for 3 min at 4° C. and the cell pellet was suspended in a 2-pack volume of cell lysis buffer (50 mM Tris-HCl, pH7.4; 1% NP-40; 150 mM NaCl; 1 mM EGTA; 1 mM PMSF; 1 mg/ml aprotinin, leupeptin, pepstatin) and vortexed thoroughly. The cell lysate was spun at 13,000 rpm for 15' at 4° C. to remove cellular debris. The supernatant was collected and the protein content estimated using the BCA (bicinchoninic acid) assay (PIERCE, Rockford, Ill.). 30 mg of total protein was mixed with an equal volume of 2×SDS sample buffer (22) and loaded onto a 10% SDS-PAGE and run at a 30 mA constant current for 2 to 2.5 hours. For the detection of iNOS, the lysate of the IFN-γ and LPS-stimulated murine macrophage (RAW 264.7) was loaded onto the gel as a positive control. The proteins were transferred to a nitrocellulose membrane overnight at a 12 mA constant current in transfer buffer (39 mM glycine, 48 mM Tris-HCl, 20% methanol) at 4° C.

Following protein transfer to the nitrocellulose membrane, the blots were immediately placed into blocking buffer (5% non-fat dry milk, 10 mM Tris-HCl, pH 7.5, 100 mM NaCl, 0.1% Tween 20) and incubated for 30' at room temperature. The blots were then individually incubated overnight with mAbs to IRF-1, IRF-2, PKR, cytokeratin-18 (SANTA CRUZ BIOTECHNOLOGY Inc, Santa Cruz, Calif.), iNOS (TRANSDUCTION LABORATORIES, Lexington, Ky.) and phospho-eIF-2a (CELL SIGNALING, Beverly, Mass.) at 4° C. Blots were washed three times in washing buffer (10 mM Tris-HCl, pH 7.5, 100 mM NaCl, 0.1% Tween 20) and were subsequently incubated with anti-mouse IgG HRP conjugate (BOEHRINGER MANNHEIM, Indianapolis, Ind.) (1:5000) for 30' at room temperature. The blots were again washed in washing buffer and developed by the addition of ECL chemiluminescent detection reagents (0.125 ml/cm2) according to the manufacturer's instructions (AMERSHAM LIFE SCIENCES, Arlington Heights, Ill.). The blots were wrapped in saran wrap and exposed to Kodak X-OMAT AR films (EASTMAN KODAK, Rochester, N.Y.).

Nitrite Assay. Nitrite, a stable breakdown product of NO in physiological systems, was assayed using the Griess reaction (23). Cell culture supernatants (100 μL) were added in triplicates to 100 μL of Griess reagent (sulfanilamide 1%, naphthylethylenediamine dihydrochloride 0.1%, phosphoric acid 2.5%) using 96-well plates (SIGMA, St. Louis, Mo.). After incubation at room temperature for 10 min, absorbance at 550 nm was measured. A doubling dilution of a 50 M sodium nitrite solution was used to generate a standard curve. The lower limit of the standard curve was 0.25 μM.

Northern Analysis. Northern blot analysis was performed to examine the mRNA expression profile of IFN-γ-induced genes. Total cellular RNA was isolated from cells using TRIZOL reagent (Life Technologies, Gaithersburg, Md.) following the manufacturer's instructions. Probes for northern hybridization were prepared by RT-PCR using gene specific primers for IRF-1 (nucleotides 7-359), 2-5 AS p40 (nucleotides 2-492), 2-5 AS p69 (nucleotides 21-503), RSV G (nucleotides 4688-5584), RSV F (nucleotides 5661-7385) and glyceraldehyde 3 phosphate dehydrogenase (GAPDH) (nucleotides 1-360). The PCR products were confirmed by sequencing. The probes were labeled using BrightStar Psoralen-Biotin labeling kit (AMBION, Austin, Tex.) following manufacturer's protocol. 10 mg of total RNA was size fractionated on 1% formaldehyde agarose gel, and transferred to nylon membranes (HYBOND N+, AMERSHAM, Piscataway, N.J.) using standard protocol (24) and cross-linked by UV irradiation (UV STRATALINKER 1800, STRATAGENE, San Diego, Calif.). Hybridization was carried out at 42° C. overnight with 2-4 μM labeled probe and UltraHyb hybridization solution (AMBION, Austin, Tex.).

The blots were washed twice with 2×SSC, 0.1% SDS for 5 minutes each and two more washes with 0.1×SSC, 0.1% SDS for 15 minutes each at 42° C. The blots were processed for detection using the BRIGHTSTAR BIODETECT Kit (AMBION, Austin, Tex.) following manufacturer's protocol. The blots were exposed to KODAK X-OMAT AR films (EASTMAN KODAK, Rochester, N.Y.) for 1-15 minutes. The bands were quantified by using Advanced Quantifier software (BIOIMAGE, Ann Arbor, Mich.) and the signals were normalized with the respective GAPDH signal.

Antisense Blocking of 2'-5' Oligoadenylate Synthetase. Phosphorothioate antisense oligonucleotides (ODNs) were designed against p40 and p69 subunits of 2'-5' oligoadenylate synthetase. The sequences of antisense ODNs are as follows: p40 subunit, 5'-TTT CTG AGA TCC ATC ATT GA-3' (SEQ ID NO: 17) and p69 subunit, 5'-TCC CCA TTT CCC ATT GC-3' (SEQ ID NO: 18). The control ODN sequences 5'-GTC TAT GAA TAC TTT CCT AG-3' (SEQ ID NO: 19) and 5'-CAC CTC TAT CTC TCT CG-3' (SEQ ID NO: 20) are a scramble of the antisense sequence to p40 and p69 isomers, respectively, i.e., identical in base composition. HEp-2 cells were treated with 1000 U/ml of IFN-γ protein for 20 hours. At the same time equimolar mixture of antisense ODNs to both the isoforms of 2-5 AS or their scrambled mismatch ODNs were added at concentrations 0, 3, 30 and 90 nM. Cells were infected with RSV at 20 h post-IFN-γ-treatment, as described earlier. After 1 h of virus adsorption, cultures were supplemented with complete medium, which contained 1000 U/ml of IFN-γ and respective concentrations of ODNs, and incubated for 72 hrs. ODNs were supplemented every 8 hours. At 72 h pi, cells were washed three times with cold PBS, pH 7.4, harvested and the clear cell homogenate was used for plaque assay.

2-5 AS Assay. A 2-5 Assay was done following the method described previously (Ghosh et al., *J. Biol. Chem.* 272:15452-15458, 1997). Briefly, 20 μl of reaction mixture containing the cell homogenate, 20 mM Tris-HCl, pH 7.5, 20 mM magnesium acetate, 2.5 mM dithiothreitol, 5 mM ATP, 5 μCi of [a-32P] ATP, and 50 μg/ml poly(I).poly(C) was incubated for 3 h at 30° C. The reaction was stopped by boiling for 3 min and centrifuged, and was incubated for 3 h at 37° C. with 3 μl of 1 unit/μl calf intestine alkaline phosphatase to convert the unreacted [a-32P]ATP to inorganic phosphate. Two μl of the sample were then spotted on a polyethyleneimine-cellulose thin layer chromatography plate and resolved in 750 mM $KH_2PO_4$, pH 3.5. The 2-5 A formed was then quantified by using Advanced Quantifier software (BIOIMAGE, Ann Arbor, Mich.) and expressed as arbitrary units.

Generation of Stable Cell Line Overexpressing Rnase L Inhibitor. Human RLI cDNA was amplified as KpnI-BamHI cassette and cloned in pcDNA3.1 (INVITROGEN, Carlsbad, Calif.) by the standard procedure (Sambrook et al., Molecular Cloning: A Laboratory Manual, and ed., Cold Spring Harbor Laboratory, NY, 1989). HEp-2 cells were transfected with 5 mg of pcDNA3.1-RLI using lipofectine (LIFE TECHNOLOGIES, Gaithersburg, Md.). The empty pcDNA3.1 vector was used as a control. Stable transfectants were selected by culturing the cells in the presence of G418 (LIFE TECHNOLOGIES, Gaithersburg, Md.). Individual clones were isolated and analyzed for the expression of RLI mRNA. The clone that expressed RLI at the highest level and had a normal morphology and growth pattern was selected and named RLI-14.

RNAse L Assay. An RNAse L assay was done by ribosomal RNA cleavage assay (Player et al., *Methods,* 15:243-253, 1998). Briefly, cells were harvested in NP-40 lysis buffer (10 mM HEPES, pH 7.5, 90 mM KCl, 1 mM magnesium acetate, 0.5% (v/v) NP-40, 2 mM 2-mercaptoethanol, 100 mg/ml leupeptin) and S10 lysate was prepared and protein content was estimated using the BCA (bicinchoninic acid) assay (Pierce, Rockford, Ill.). Ribosomal RNA cleavage by RNAse L was assayed in a 20 ml reaction containing 200 mg protein, 2 ml of 10× cleavage buffer (100 mM HEPES, pH 7.5, 1 mM KCl, 50 mM magnesium acetate, 10 mM ATP, 0.14 M 2-mercaptoethanol), 100 nM 2'-5'A and incubated at 30° C. for 2 h. RNA was isolated from the reaction using TRIZOL reagent (LIFE TECHNOLOGIES, Gaithersburg, Md.) following the manufacturer's instructions. 2 mg of RNA was separated on agarose gel electrophoresis and the rRNA cleavage products were compared.

Animals. Female 6-8 weeks old wild type and STAT4$^{-/-}$ BALB/c mice from Jackson Laboratory (Bar Harbor, Me.) were maintained in pathogen free conditions at the animal center at USF College of Medicine. All procedures were reviewed and approved by the committee on animal research at the University of South Florida College of Medicine.

Cloning and recombination of adenoviral vectors. Murine 25 AS (p40) cDNA was cloned into adenoviral transfer vector pShuttle-CMV (STRATAGENE, CA) at KpnI and XhoI sites. The left and right arms of pShuttle-CMV vector contains Ad5 nucleotides 34,931-35,935 and 3,534-5,790, which mediate homologous recombination with pAdEasy-1 vector in E. coli, plus inverted terminal repeat (ITR) and packaging signal sequences (nucleotides 1-480 of Ad5) required for viral production in mammalian cells. pAdEasy-1 adenoviral plasmid (STRATAGENE, CA) contains all Ad5 sequences except nucleotides 1-3,533 (encompassing the E1 gene) and nucleotides 28,130-30,820 (encompassing E3).

For generation of recombinant adenovirus plasmid, pShuttle-CMV-p40/LacZ plasmids were linearized with PmeI and co-transformed with pAdEasy-1 plasmid into recombination proficient BJ5183 cells. The recombination was confirmed by PacI digestion. The recombined clones were re-transformed into DH5α cells for large-scale plasmid purification.

Generation and purification of recombinant adenovirus. HEK293 cells, which produce the deleted E1 genes in trans, were transfected with 4 μg of PacI digested recombinant adenovirus plasmid DNA with lipofectin (LIFE TECHNOLOGIES, MD). Cells were harvested 7-10 days post-transfection, resuspended in PBS and recombinant virus was collected by 3-4 freeze-thaw cycles. The recombinant virus expressing murine p40 and LacZ were termed Ad-p40 and Ad-LacZ, respectively. The viruses were amplified by infecting fresh HEK-293 cells. Viruses were further purified by CsCl banding (Becker et al., *Methods Cell Biol.*, 43 Pt. A:161-189, 1994). The viral band was extracted and CsCl was removed by passing through Centricon-100 columns (MILLIPORE, MA).

Quantitation of RSV titers in lung. To quantify RSV titers in the mouse lung whole lungs were first weighed and placed immediately in EMEM media supplemented with 10% FBS. Lungs were homogenized, centrifuged at 10,000 RPM for 10 minutes at 4° C., the clear supernatants were used for plaque assays by shell vial technique (Kumar et al., 2002).

Pulmonary Function. To evaluate the pulmonary function in vaccinated and control groups, mice were administered IGT, as described earlier. Three days later, airway responsiveness was assessed non-invasively in conscious, unrestrained mice with a whole body plethysmograph (BUXCO ELECTRONICS, Troy, N.Y.), as previously described (Matsuse et al., *J. Immunol.* 164:6583-6592, 2000). With this system, the volume changes that occur during a normal respiratory cycle are recorded as the pressure difference between an animal-containing chamber and a reference chamber. The resulting signal is used to calculate respiratory frequency, minute volume, tidal volume, and enhanced pause (Penh). Penh was used as the measure of bronchoconstriction and was calculated from the formula: Penh=pause×(peak expiratory pressure/peak inspiratory pressure), where pause is the ratio of time required to exhale the last 30% of tidal volume relative to the total time of expiration. Mice were placed in the plethysmograph and the chamber was equilibrated for 10 min. They were exposed to aerosolized PBS (to establish baseline) followed by incremental doses (6, 12.5, 25, and 50 mg/ml) of methacholine (SIGMA CHEMICALS, St. Louis, Mo.). Each dose of methacholine was aerosolized for 5 min, and respiratory measurements were recorded for 5 min afterward. During the recording period, an average of each variable was derived from every 30 breaths (or 30 s, whichever occurred first). The maximum Penh value after each dose as used to measure the extent of bronchoconstriction.

Bronchoalveolar lavage (BAL) and histology of the lung. Bronchoalveolar lavage were performed on Ad-p40 administered and control mice, as described before (Kumar et al., 1999). Histological staining and a semiquantitative analysis of airway inflammation from the lungs of p40 treated and control groups of mice were performed, as described earlier (Kumar et al., 1999). Lung inflammation was assessed after staining the sections with hematoxylin and eosin (HE). The entire lung section was reviewed, and pathological changes were evaluated for epithelial damage, peribronchovascular cell infiltrate, and interstitial-alveolar cell infiltrate for the mononuclear cells and polmorphonuclear cells.

Statistical Analysis. Experiments were repeated 2 to 4 times for each experiment as indicated. Statistical significance was analyzed using paired two-tailed student's t-test. Differences were considered statistically significant when the p-value was less than 0.05.

Example 1

IFN-γ Attenuates RSV Infection in Human Epithelial Cells

Figure 1A:
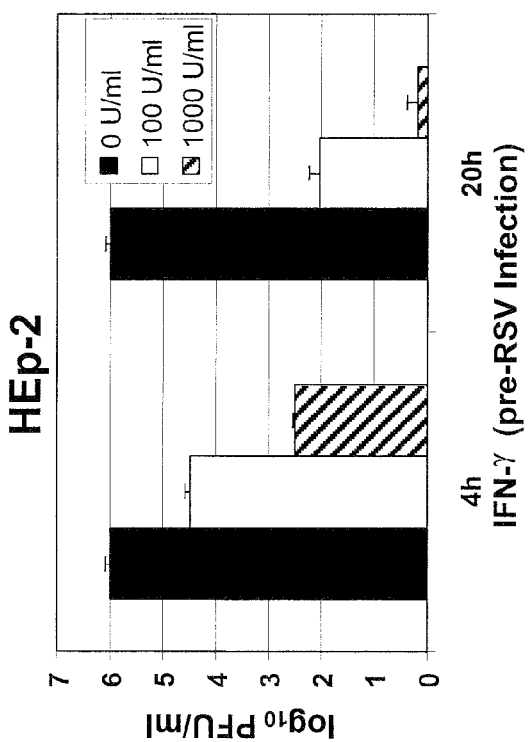
Figure 1D:
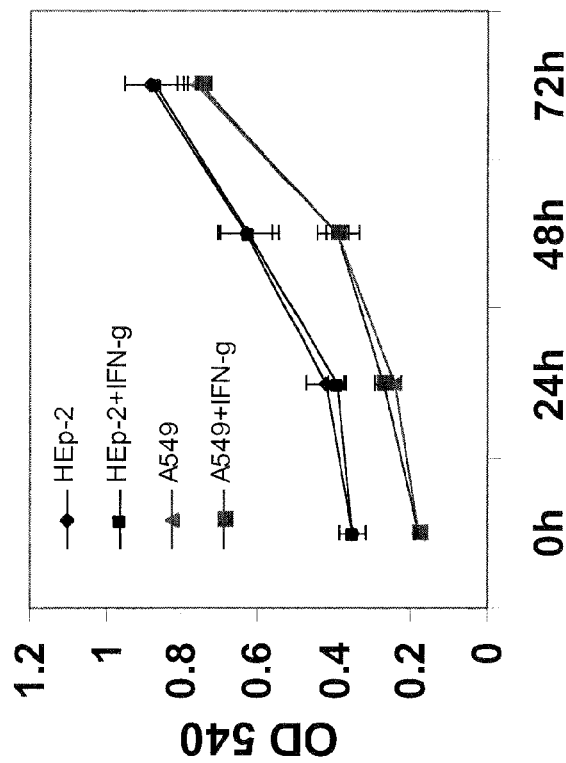
Figure 1C:
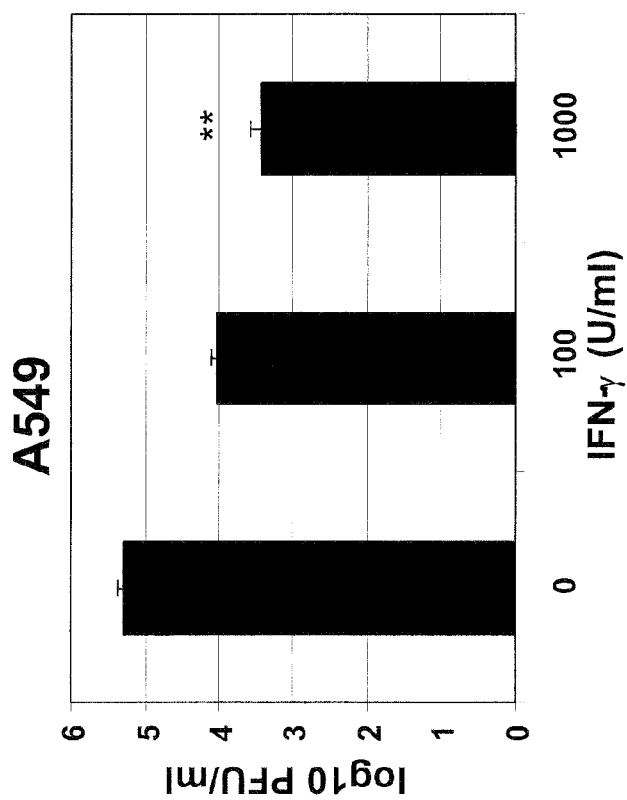

To examine the effect of IFN-γ on RSV infection, HEp-2 cells were pre-incubated for 4-20 h with different concentrations of IFN-γ and subsequently infected with RSV. Respective concentrations of IFN-γ were added back to the cells in complete medium after the removal of viral inoculum. Cells were harvested at 72 h p.i., and viral titer was determined by plaque assay. RSV replication was inhibited significantly with the addition of various concentrations of IFN-γ to both cell lines prior to RSV infection (FIGS. 1A and B). A 97% inhibition of replication was observed in HEp-2 and A549 cells, at 1000 U/ml of IFN-γ added at 20 h pre-infection. Cells treated with IFN-γ 4 h pre-infection also showed significant reduction (p<0.01) in RSV titer (50% reduction). A significant decrease (p<0.01) in RSV titer (39% reduction) was observed in A549 cells, which were not treated with IFN-γ before infection, but were only treated at 1 h post infection (FIG. 1C). To rule out the possibility that the reduction in RSV titers could be due to cytotoxicity of IFN-γ, a MTT cytotoxicity assay was performed. The results indicate that the cells were metabolically as viable as the untreated control cells when treated with the highest concentrations of IFN-γ (1,000 U/ml; FIG. 1D). Thus, IFN-γ did not exhibit any cytotoxic or growth inhibitory effect on these cells. These results suggest that the treatment of cells with soluble IFN-γ results in a significant decrease in RSV infection in epithelial cells.

Example 2

IFN-γ Induces IRF-1 Protein Expression

Figure 2A:
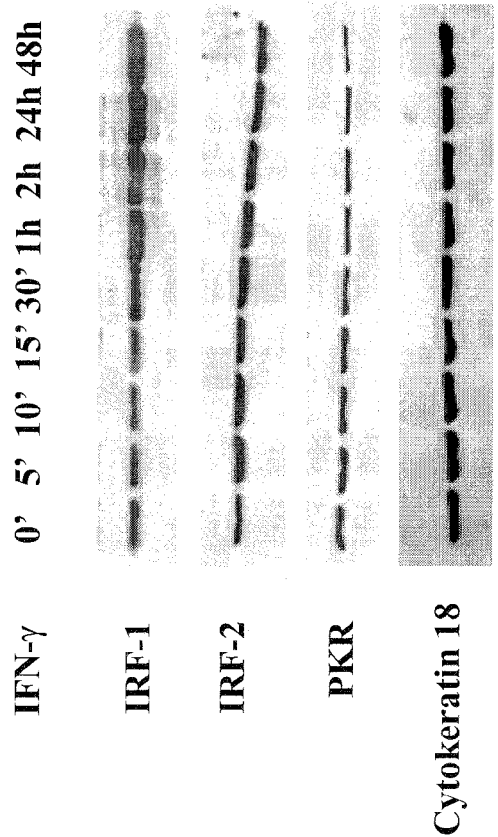
FIGS. 2A and 2B show results of a western blot analysis using specific antibodies to IRF-1, IRF-2, cytokeratin-18, double stranded RNA protein kinase (PKR), and inducible nitric oxide synthase (iNOS). Proteins were analyzed from cells at various time points post treatment with IFN-γ (1000 U/ml). Cytokeratin-18 was used as an internal control.
Figure 2B:
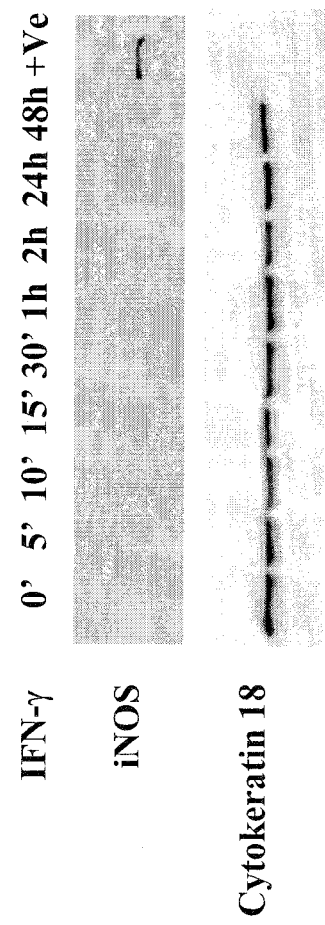

ISGs implicated in the antiviral activity of IFNs include IRFs, double stranded RNA activated protein kinase (PKR)

and inducible nitric oxide synthase (iNOS). To identify the ISGs in these cells potentially involved in protection against RSV infection, proteins were analyzed from cells at various time points post treatment with IFN-γ (1000 U/ml). A western blot analysis was performed using specific antibodies to IRF-1, IRF-2 and PKR (FIG. 2A). There was increased expression of IRF-1 but no change in the expression of IRF-2 following IFN-γ addition. Expression of IRF-1 increased after 30' of IFN-γ addition. The expression of PKR decreased gradually over time (FIG. 2B) and no change in the expression of phospho-eIF-2a was observed following IFN-γ addition. Cytokeratin-18 was used as an internal control, the expression of which did not change with the addition of IFN-γ. To examine if IFN-γ induced iNOS plays a role in antiviral action, iNOS expression was examined by western blotting (FIG. 2B). The expression of iNOS protein could not be detected before and after IFN-γ addition. Murine macrophage cell lysate containing iNOS was used as a positive control, which did not bind to the cytokeratin-18 antibody used as internal control. To rule out completely the involvement of iNOS in the antiviral effect of IFN-γ, the level of nitric oxide (NO) was examined in the culture supernatant of both HEp-2 and A549 cells before and after the addition of IFN-γ at various time points. No detectable level of NO (lowest concentration of standard was 0.25 mM) was observed in both cell lines at any time point, i.e., before or after IFN-γ addition in both cell lines. A similar expression pattern was observed for IRF1, IRF2, PKR and iNOS in A549 cells. These results indicate that IFN-γ up-regulates IRF-1 in these cells and neither PKR nor iNOS play any role in the antiviral activity of IFN-γ against RSV infection in human epithelial cell lines.

Example 3

Exogenous IFN-γ Upregulates mRNA Synthesis of IRF-1 and 2-5 AS

Figure 3:
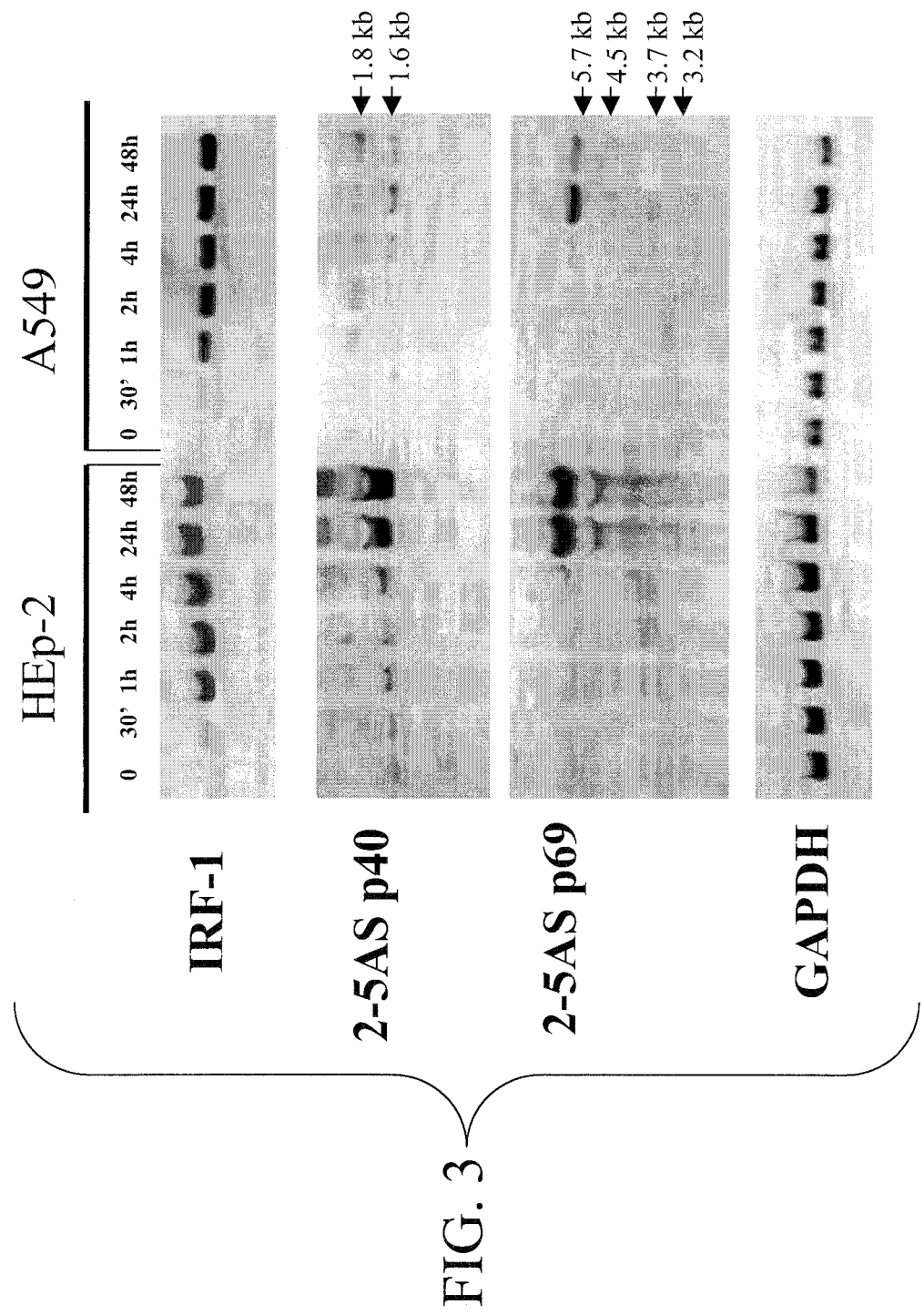

IRF-1 has been reported to play a role in antiviral activity via the induction and activation of 2-5 AS (Reis et al., *EMBO J.* 11:185-193, 1992). Northern analysis was performed using gene specific probes for IRF-1 and the p40 and p69 isoforms of 2-5 AS (FIG. 3). The IRF-1 mRNA was induced at 30 min after addition of IFN-γ and continued to increase gradually thereafter until 48 h post exposure. The induction of the p40 and p69 isoforms of 2-5 AS was observed starting at 4 h and peaked at 24 h post exposure. The p40 probe hybridized to two transcripts of 1.8 and 1.6 kbp. Similarly, the p69 probe hybridized to four expected transcripts of 5.7, 4.5, 3.7 and 3.2 kbp of which 5.7 kbp was the major transcript. These results suggest that IFN-γ induces IRF-1, which in turn, up regulates 2-5 AS, suggesting that the latter may be involved in the anti-RSV mechanism of IFN-γ.

Example 4

Figure 4:
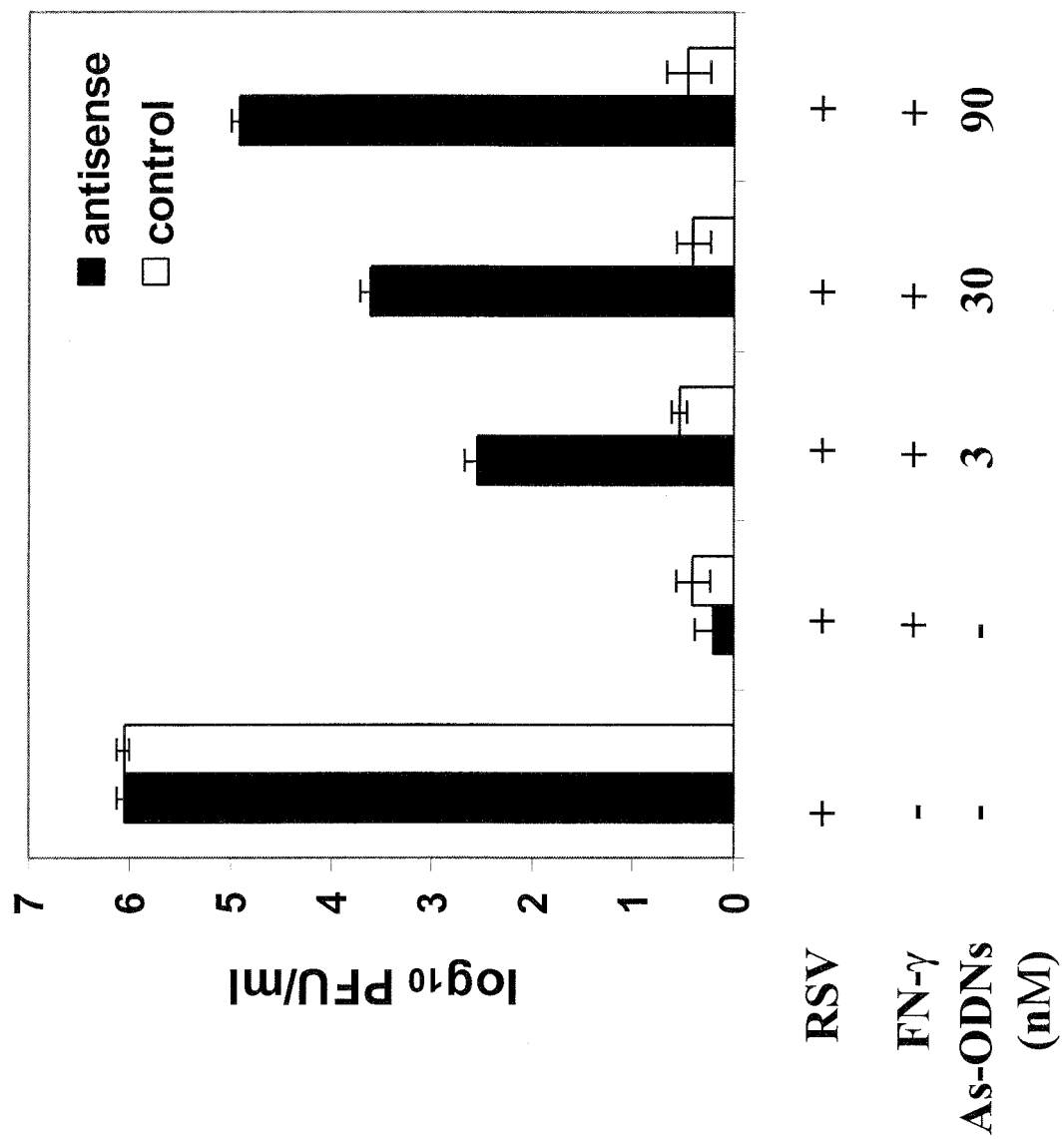
FIG. 4 shows results of exposure of HEp-2 cells to IFN-γ (1000 U/ml at 20 hours pre-infection) and treatment with equimolar mixtures of antisense oligonucleotides (ODNs) to both p40 and p69 isoforms of 2-5 AS. Scrambled mismatch of the antisense ODN sequence to p40 and p69 at the same concentration were used as control.

2-5 as Antisense Oligonucleotides Abrogate the Antiviral Effect of IFN-γ in HEp-2 Cells To investigate whether IFN-γ induced anti-RSV activity is mediated by 2-5 AS, IFN-γ exposed (1000 U/ml at 20 h pre-infection) HEp-2 cells were treated with equimolar mixture of antisense oligonucleotides (ODNs) to both p40 and p69 isoforms of 2-5 AS. Scrambled mismatch of the antisense ODN sequence to p40 and p69 at the same concentration were used as control. RSV infection was barely detectable in cells either treated with IFN-γ alone or with cells treated with IFN-γ and control ODNs but not in those treated with IFN-γ and antisense ODNs, as shown in FIG. 4. Addition of antisense ODN significantly reverted (p<0.01) the antiviral effect of IFN-γ against RSV infection and this reversal was dose-dependent and increased with increasing concentrations of antisense ODNs. As shown in FIG. 4, 2-5 AS activity was reduced in a dose dependent manner in the cells treated with antisense ODN to 2-5 AS but not control ODN. These results indicate that the addition of antisense ODNs to 2-5 AS to IFN-γ-treated cells reduced 2-5 AS activity in these cells and in turn the antiviral effect of IFN-γ.

Example 5

Figure 5D:
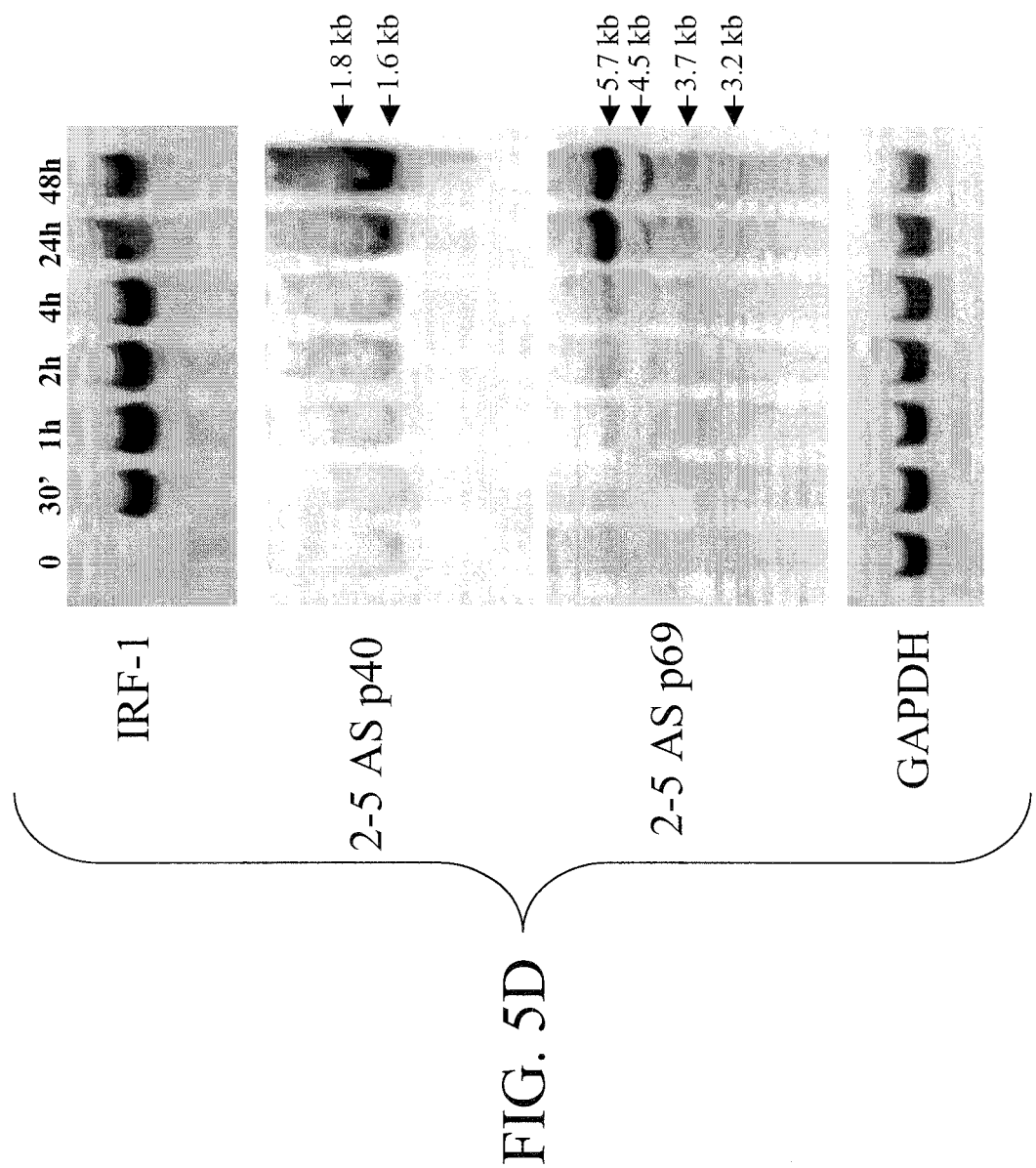

Overexpression of RNAse L Inhibitor (RLI) does not Alter the IFN-γ Responses in HEp-2 Cells In addition to RNAse L, RNAse L inhibitor (RLI) has been implicated in the antiviral effect of IFN-γ. To determine the role of 2-5 A/RNase L-mediated antiviral mechanism, a stable cell line expressing RLI, RLI-14, was established. A northern analysis of RNAs from RLI-14 and HEp-2 using gene specific probe for RLI showed a major 3.5 kb transcript and a minor 2.8 Kb transcript (FIGS. 5A and 5B). A seven-fold increase in the major RLI transcript expression was observed in RLI-14 cells when compared to HEp-2 cells. The analysis of IFN-γ induced proteins in RLI-14 cell line by western blotting showed that IFN-γ induced expression of IRF-1, but not IRF-2, at 30 min post induction and IRF-1 expression continued to increase thereafter until 48 h (FIG. 5C) as in HEp-2 cells (FIG. 2A). Also, a time-specific decrease in PKR protein concentration was observed after IFN-γ addition in the RLI-14 cell line. The expression of cytokeratin-18, used as an internal control, remained unchanged with IFN-γ addition. The level of mRNA expression of IRF-1, p40 and p69 isoforms of 2-5 AS was observed by northern analysis, and the expression level showed a gradual increase over time following IFN-γ stimulation (FIG. 5D) as in HEp-2 cells (FIG. 3). These results suggest that overexpression of RLI does not change the expression pattern of the IFN-γ-induced genes involved in antiviral activity of these cells.

Example 6

RNase L Inhibitor (RLI) Overexpression Decreases the Antiviral Activity of IFN-γ

Figure 6:
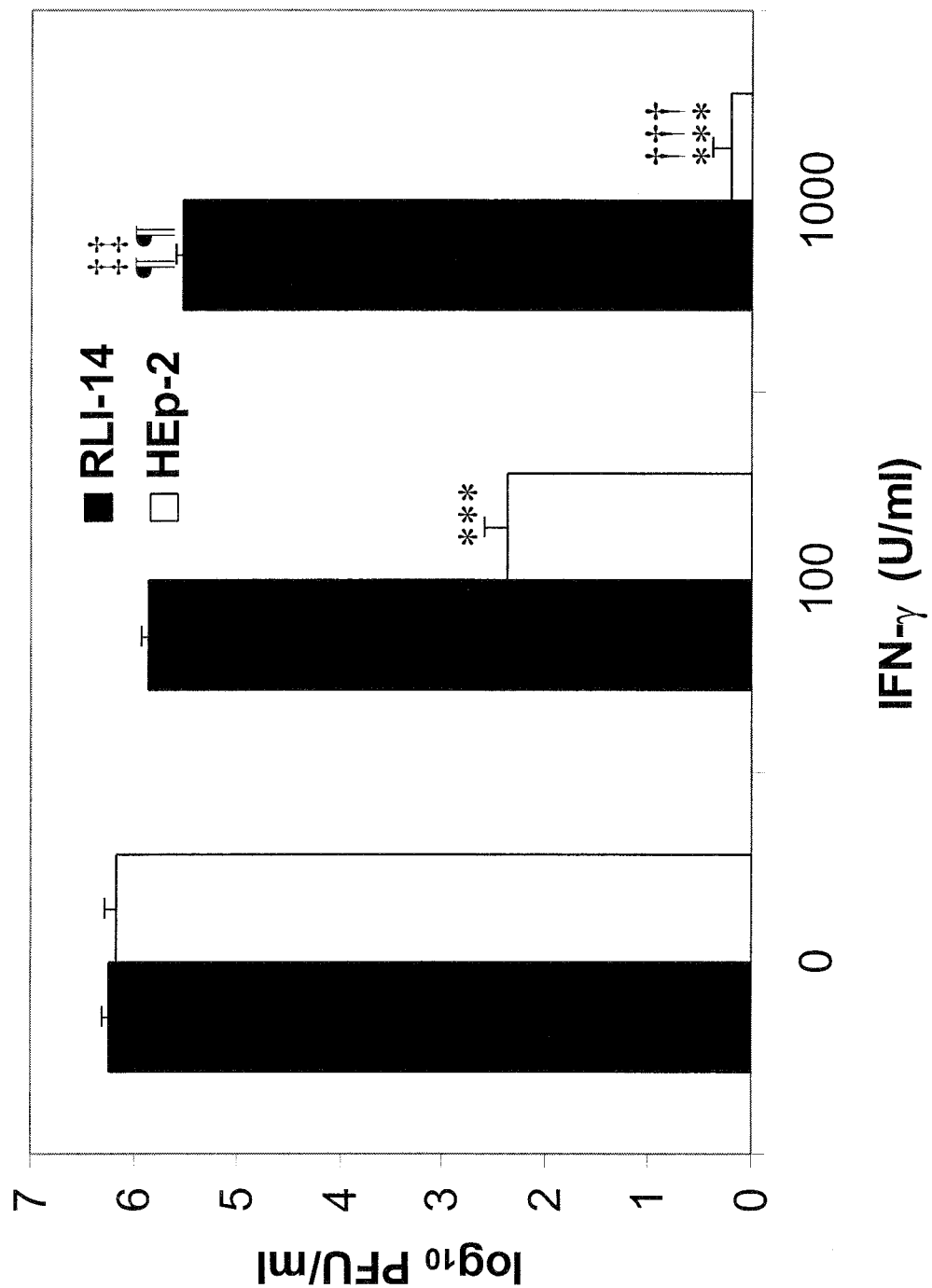
FIG. 6 show the results of treatment of both HEp-2 cells and RLI-14 cells with IFN-γ (at 100-1000 U/ml at 20 hours pre-infection) and subsequent infection with RSV.
Figure 7:
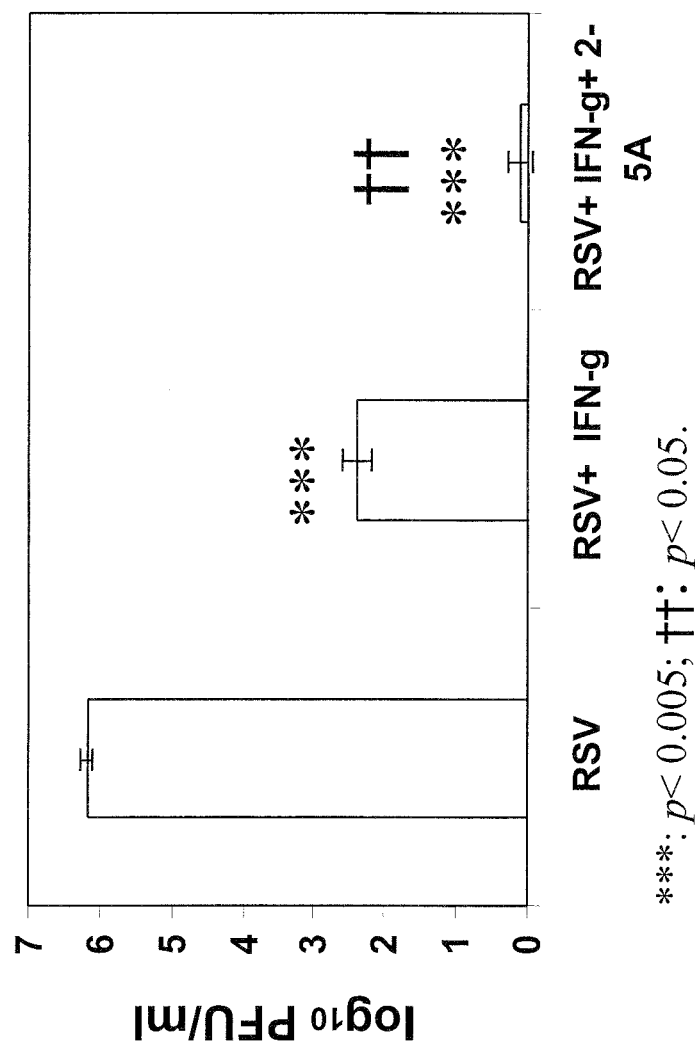
FIG. 7 shows the results of treatment of HEp-2 cells with IFN-γ (at 100-1000 U/ml at 20 hours pre-infection) and subsequent infection with RSV. 2-5 A was transfected at 3 hours prior to RSV infection. Cells were harvested at 72 hours post infection and the clear cell homogenate was used for the RSV plaque assay (***: $p<0.005$; ††: $p<0.05$).

To examine the effect of the overexpression of the RNase L inhibitor, both HEp-2 and RLI-14 cells were treated with IFN-γ at 100-1000 U/ml at 20 h pre-infection and subsequently infected with RSV. IFN-γ was added back to the cells at respective concentrations following RSV infection. HEp-2 cells treated with 100 and 1000 U/ml of IFN-γ showed significant inhibition (p<0.001) of RSV infection (72% and 97% reduction, respectively) when compared to untreated cells. In marked contrast, RLI-14 cells showed significantly lower inhibition of infection (only 12% and 22% reduction, respectively) compared to HEp-2 cells at respective concentrations of IFN-γ, as showed in FIG. 6. In absence of IFN-γ treatment, both cell lines exhibited identical RSV titers upon infection. However, the viral titer significantly decreased (p<0.01) when the concentration of IFN-γ was increased from 100 U/ml to 1000 U/ml in RLI-14 cells. This demonstrates that increase in IFN-γ led to higher expression of 2-5 AS and in turn production of 2-5 A, which subsequently bound to RNase L and increased the level of active RNase L by releasing RNase L from its inactive complex. Reduction in virus replication was inhibited in RLI-14 cells (%) when compared to HEp-2 cells (%), as shown in FIG. 6. In order to examine whether the reduction in inhibition of RSV infection in RLI-14 cells was due to reduced RNAse L activity in these cells, RNAse L assay was done using ribosomal RNA cleavage assay. This reaction uses cell lysate as a source of both substrate and enzyme, thus giving a comparison of the ribonuclease activity of RNAse L in different cell types. The results confirm that ribonuclease activity of RNAse L is indeed reduced in RLI-14 cells when compared to HEp-2 cells as evident from the rRNA cleavage products, as shown in FIG. 6. Together, these results confirm the involvement of 2-5 A/RNase L in the antiviral effect of IFN-γ against RSV infection.

The finding that treatment of HEp-2 and A549 cells at 20 h pre-infection with as low as 100 U/ml of IFN-γ proteins inhibits RSV infection and replication when compared to untreated cells, has significant therapeutic implications. HEp-2 and A549 cells treated with 1000 U/ml of IFN-γ at 20 h pre-infection exhibited a 97% (30-31 fold in log 10 PFU/ml) reduction in RSV titer. The RSV titer also decreased by 39% (1.7 fold reduction in log 10 PFU/ml) in these cells, which were not treated with IFN-γ prior to infection but were only treated immediately after RSV infection. RSV is resistant to the antiviral effects of type-I interferons and human MxA. It has been reported that overexpression of IFN-γ by gene transfer and by recombinant RSV attenuates RSV replication in a mouse model of RSV infection. However, the mechanism of antiviral action of IFN-γ against RSV is not known.

The elucidation of the mechanism underlying IFN-γ-mediated resistance to RSV infection in human epithelial cells has been the main focus of this invention. The mechanism of antiviral action of IFN-γ is complex and may be unique for individual cell lines and viruses. A profile of ISGs, relevant to antiviral activity in these epithelial cells, establish that IFN-γ exposure results in induction of both the mRNA and protein for IRF-1 but not IRF2. In non-induced cells the IRF-2 protein functions as a repressor of ISGs. IFN-γ induction temporarily removes this repression and activates ISGs including IRF-1. IRF-1 and IRF-2 compete for the same cis acting recognition sequences but with opposite effects. Findings in these epithelial cells are consistent with those found for human macrophages, where IFN-γ treatment does not enhance IRF-2 gene expression, despite strong upregulation of IRF-1 mRNA expression. Two additional ISGs, PKR and iNOS proteins were examined for their role in IFN-γ induced antiviral activity. IFN-γ activates PKR, which in turn phosphorylates and inactivates eukaryotic initiation factor-2a (eIF-2a) and leads to restriction of cellular as well as viral protein synthesis. The iNOS is also known to mediate antiviral property of IFN-γ. However, a time specific decrease in PKR expression and no change in phosphorylation of eIF-2a and the lack of detectable levels of iNOS protein or NO in IFN-γ-stimulated HEp-2 and A549 cells indicate that neither PKR and phospho-eIF-2a nor iNOS play any role in IFN-γ mediated inhibition of RSV infection in these cells.

To further dissect the mechanism of IFN-γ mediated anti-RSV activity in HEp-2 and A549 cells, IRF-1 induced expression of 2-5 AS was examined. Of the four isoforms (p40, p46, p69, and p100) of 2-5 AS detected in human cells to date, the expression pattern of the p40 and p69 isoforms following IFN-γ stimulation was examined in this study because of the following. The p40 and p46 isoforms of 2-5 AS, which are dependent on dsRNA for activation, are derived from the same gene by differential splicing between the fifth and an additional sixth exon of this gene and are thus identical for the first 346 residues, except for their C-terminal ends. Of the two high molecular weight isoforms, p69, but not p100, requires dsRNA for activation. The expression of 2-5 AS p40 and p69 are induced by IFN-γ in these cells at 4 h and peaks at 24 h post IFN-γ addition. Therefore, the antiviral effect of IFN-γ in these cells is observed when the cells are treated with IFN-γ at 4 h pre-infection and is highest when treated at 20 h pre-infection as the level of 2-5 AS is at peak at that time. These data suggest that the antiviral mechanism of IFN-γ against RSV infection is mediated by the activation of IRF-1, which in turn activates the 2-5 AS system. A dose-dependent abrogation of 2'-5' AS activity and in turn the anti-RSV effect of IFN-γ by the addition of an equimolar mixture of antisense ODNs to p40 and p69, but not by the scrambled mismatch ODNs, provide evidence supporting the role of 2-5 AS in the antiviral mechanism of IFN-γ against RSV infection.

2-5 AS induces 2-5 A, which binds to and activate RNase L, which cleaves double stranded RNA 3' of UpN residues. The levels of RNase L are increased in growth-arrested cells and following IFN-γ treatment; however, its biological activity is thought to be controlled at the level of enzymatic activation rather than through regulation of its transcription and translation. Increasing endogenous levels of 2-5 A leads to enhanced RNase L activity, which suggests that intracellular levels of 2-5 A are rate limiting in the activation of RNase L, whereas cellular levels of RNase L are sufficient for maximal biological activity. Furthermore, RNase L remains in an inactive form in the cells being bound to an inhibitor, RLI, which codes for a 68 kDa protein whose mRNA is not regulated by IFN-γ. RLI induces neither 2-5 A degradation nor reversible modification of RNase L when expressed in a reticulocyte lysate, but antagonizes the binding of 2-5 A to RNase L, thus, its nuclease activity, since 2-5 A binding is a prerequisite to RNase L dimerization and activation.

RLI-14, a stable cell line overexpressing RLI, was established from HEp-2 cells and characterized to determine precisely the involvement of RNase L in the antiviral mechanism of RSV infected epithelial cells. The finding that RLI-14 was almost identical to the parent HEp-2 cells in its response to IFN-γ shows that RLI overexpression does not alter the induction of ISGs in these cells (FIGS. 5A-D). Nonetheless, reduced RNAse L activity and antiviral activity of IFN-γ in RLI-14 cells (FIG. 6), confirmed that the RNase L activity is indeed critical to the antiviral effect of IFN-γ and is only partly controlled by the elevated levels of 2-5 AS in these cells following IFN-γ treatment. The reduction in antiviral effect of IFN-γ in these cells was dependent on the dose of IFN-γ, indicating that the level of 2-5 A, which is regulated by IFN-γ and the level of RLI are crucial in determining which pathway cells will follow. The importance of the level of 2-5 A was confirmed by preliminary findings which showed significant reduction in RSV infection when HEp-2 cells were treated with 100 U/ml of IFN-γ 20 h pre-infection and transfected with 1 mM 2-5 A 2 h pre-infection, when compared to the cells treated with 100 U/ml of IFN-g alone. Similarly the importance of the level of RLI in the antiviral activity was reported for HIV, where RLI is induced during HIV1 infection and down regulates the 2-5 A/RNase L pathway in human T cells.

In summary, these results demonstrate that IFN-γ inhibits RSV infection of human epithelial cells. Specifically, in HEp-2 and A549 epithelial cells, IFN-γ upregulates IRF-1, which in turn, induces 2-5 AS. Further, the 2-5 AS generates 2-5 A that activates RNase L, which is normally found in the cytoplasm in inactive state bound to RLI. Thus, RNase L-mediated cleavage of viral RNA is governed by the ying-yang mechanism involving 2-5 A and RLI. In a 2-5 A-dominant state cells are protected from RSV infection due to the activation of RNase L. In contrast, an RLI-dominant condition attenuates the antiviral effect by inactivation of RNase L. Since, 2-5 A and RLI are respectively, governed by IFN-γ-dependent and independent mechanisms, treatment with IFN-γ or overexpression of 2-5 AS should provide an efficient means to redirect the 2-5 A:RLI ratio toward a shift in favor of 2-5 A and achieve a profound antiviral effect.

Example 7

2-5 AS Plasmid DNA Vaccination Attenuates RSV Infection and Pathogenesis

As shown in FIG. 8A, 2-5 AS pDNA vaccine decreases lung RSV titers. BALB/c mice (n=4) were intranasally administered with p2'-5' AS (25 mg of DNA each time complexed with lipofectamine) or an equal amount of empty pVAX vector DNA 3 times in 2-day intervals. Mice were infected with RSV seven days after last DNA administration and were sacrificed on day 5 post-infection. BAL was performed and lungs were collected. RSV titer was determined by plaque assay from the lung homogenate. The results show that 2-5 AS cDNA vaccination can significantly attenuate lung titers of RSV in infected mice.

FIG. 8B shows that reduction of viral titers is associated with reduction in MIP-1α. Expression level of MIP-1α was determined from lung homogenate by ELISA. The results show that vaccination with 2-5 AS cDNA decreases production of chemokine MIP-1α which is known to be proinflammatory in action.

Figure 9A:
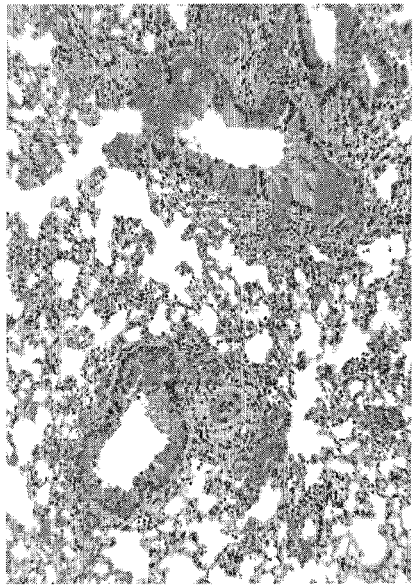
FIGS. 9A-9C show representative photomicrographs of lungs stained with hematoxylin and eosin (H & E).
Figure 9B:
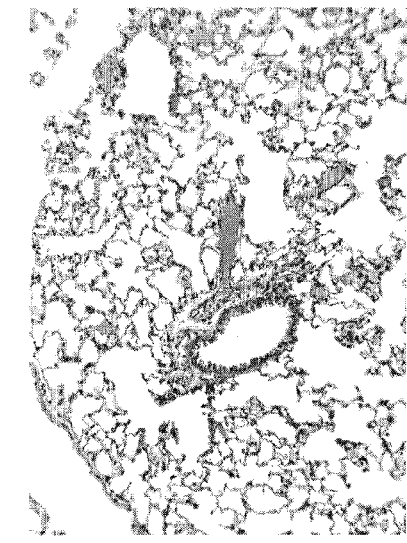
Figure 9C:
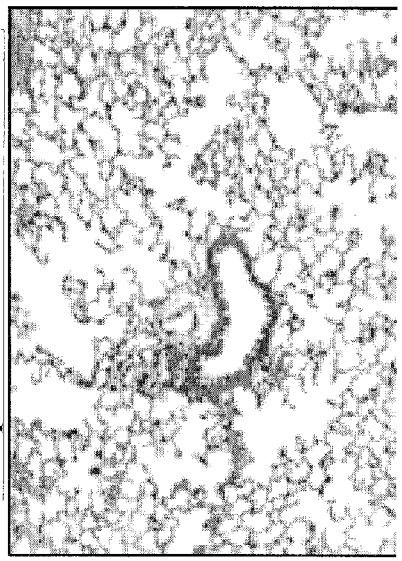

In FIG. 8C, 2-5 AS overexpression increased the macrophage population significantly compared to RSV infected mice. BAL cell differential was performed and percentages of macrophage, lymphocytes, and neutrophils were determined. The results show that 2-5 AS does not alter the cellular composition of the lung. No significant changes are seen in lymphocytes and macrophages, however the percent of neutrophils is increased in the lungs of mice treated with 2-5 AS cDNA. FIGS. 9A-9C show that 2-5 AS vaccination significantly decreased pulmonary inflammation. Histological sections from lungs were stained with hematoxylin and eosin and representative photomicrographs are shown.

Example 8

AD-2-5 AS (P40) Decreases Lung RSV Titers

Figures 10, 11:
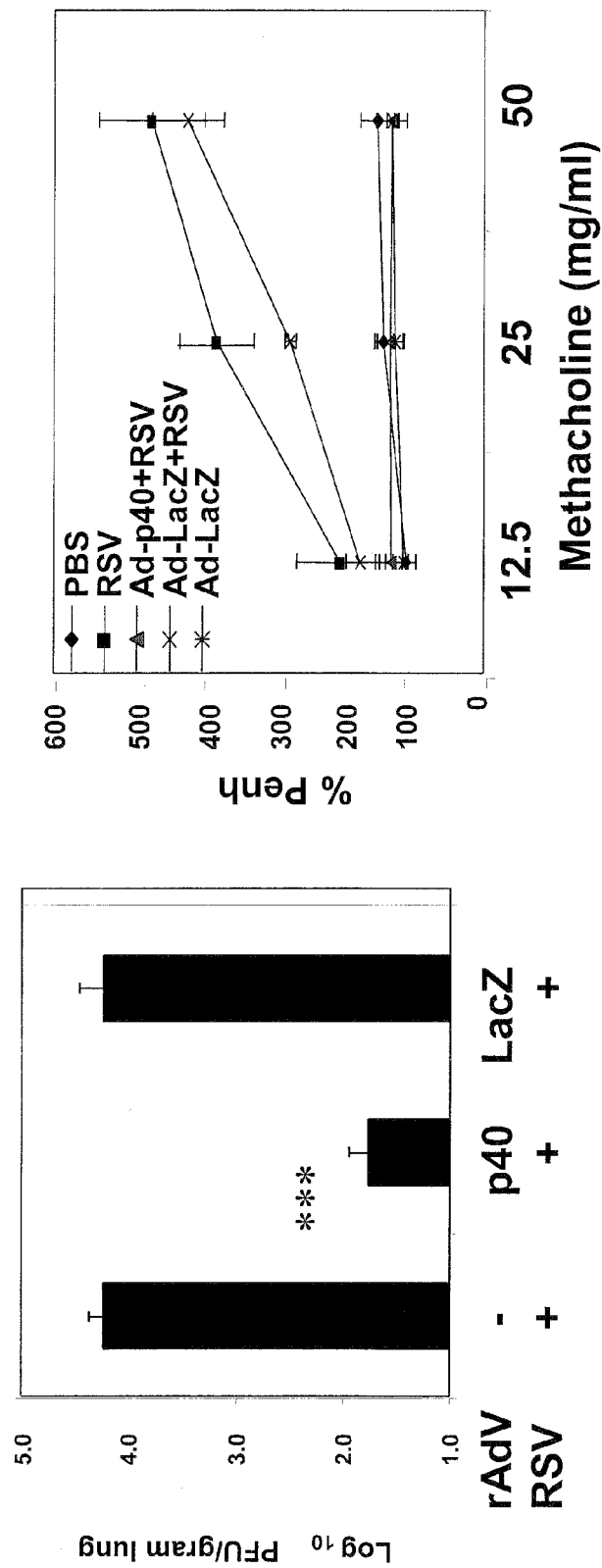
FIG. 10 shows results of treatment with adenoviral vector (Ad)-2-5 AS (p40) results in attenuation of RSV replication. BALB/c mice were intranasally administered with Ad-p40 and then infected with RSV. Lungs were harvested five days post RSV infection and RSV replication was assayed by RT-PCR analysis of RSV-N gene. GAPDH was used as internal control.
FIG. 11 shows that Ad-p40 attenuates RSV lung titers. Mice were intranasally given Ad-p40 and then infected with RSV. Lungs were harvested five days post RSV infection and lung homogenate was used for RSV plaque assay. Ad-LacZ was used as control.

A reduction in virus titer is the gold standard by which the effectiveness of an antiviral therapy is measured. Mice were intranasally administered with $10^8$ PFU/ml rAD-p40 and then infected with RSV 4 h later. Analysis of lung virus titers following acute, live RSV infection at day 5 post infection show a significant (100-fold, $P<0.01$) reduction in RSV titers in Ad-p40 treated mice compared to controls (FIG. 10). These results indicate that the rAD-p40 treatment constitutes an effective prophylaxis against RSV infection.

Example 9

AD-2-5 AS (P40) Decreases AHR in Mice

The safety of an antiviral therapy especially can be measured by a decrease in RSV-induced AHR. To test whether Ad-p40 administration reduces RSV-induced airway hyperreactivity, the % baseline enhanced pause (Penh) was measured in a group of mice treated with rAD-p40 prior to RSV infection and their AHR was compared with untreated RSV infected group. Mice receiving Ad-p40 exhibited a similar response to methacholine challenge when compared to uninfected PBS control group (FIG. 10). These results suggest that the Ad-p40 induced decrease in RSV infection decreases AHR.

Example 10

AD-2-5 AS (P40) Normalizes Cellular Infiltration to the Lung

The inflammation in the lung due to RSV infection is due to infiltration into the lung of a large number of macrophages and lymphocytes. To determine whether treatment with rAD-p40 affects migration of these cells to the lung, mice administered with rAD-p40 and RSV infected were compared to RSV infected mice without treatment and naïve mice as control and to rAd-lacZ as control. Mice with p40 gene transfer and RSV infection show a BAL cell differential similar to that of normal uninfected animals, lack of AHR compared to RSV-infected animals without p40 gene transfer and lack of the peribronchiolar and perivascular inflammation suggesting that intranasal p40 can potentially be an effective antiviral approach in vivo for RSV infection.

Example 11

AD-2-5 AS(P40) Decreases RSV Infection-Induced Pulmonary Inflammation

Lung inflammation was examined in different groups of mice. Mice treated with Ad-p40 and Ad-lacZ upon acute RSV infection exhibit relatively less disruption of the epithelium and cellular infiltration. Representative pathological features reveal that groups of mice receiving Ad-p40 exhibit less epithelial damage, and reduced mononuclear cell (MNC) and polymorphonuclear cell (PMNC) infiltrates in the interstitial and peribronchovascular region, as compared to Ad-lacZcontrols (FIGS. 12A-12H). These results suggest that the Ad-p40 protects mice from RSV infection-induced pulmonary inflammation. These results suggest that Ad-p40 protects mice from RSV infection-induced pulmonary inflammation.

The finding that transient gene expression therapy can substantially reduce lung RSV titers by 2 logs (100-fold), inhibit RSV-infection induced AHR and make the lung resistant to inflammation by acute RSV infection is very significant. These results suggest tremendous therapeutic potential of this approach. The other members of this family include the measles virus, the sendai virus, parainfluenza 1, 2, and 3, the mumps virus, the simian virus, and the newcastle virus. This finding is also important for other Paramyxoviruses, such as rotavirus that causes juvenile diarrhea in millions of children worldwide. Furthermore, beyond this family of viruses, the 2-5 AS/RNase L cascade has been implicated in the anti-viral activity of picorna viruses, (Hassel, B A et al. *Embo J*, 1993, 12 (8):3297-304; Benavente, J et al. *J. Virol*. 1984, 51 (3): 866-71; Goswami, B B and Sharma, O K. *J Biol Chem*, 1984, 259 (3):1371-4; Nilsen, T W et al. *Mol Cell Biol*, 1983, 3 (1):64-9), vaccinia virus (Maitra, R K and Silverman, R H. *J Virol*, 1998, 72 (2):1146-52; Banerjee, R et al. Virology, 1990, 179 (1):410-5), reovirus (Kumar, R et al. *J Virol*, 1988, 62 (9):3175-81), HIV (Saito, H et al. *Keio J Med*, 1996, 45 (3):161-7; 45), EMCV (Glezen, W P et al. *Am J Dis Child*, 1986, 140 (6):543-6), Hepatitis B and C virus (Groothuis, J R et al. *Pediatrics*, 1988, 82 (2):199-203; Nelson W E, Behrman R E, Kliegman R. *Nelson Textbook of Pediatrics*. 15 ed. Philadelphia).

Moreover, besides human disease, this finding may have implications, for RSV of cattle (BRSV), sheep, and goats. If 2-5 AS mediated approach is successful, the mortality and morbidity due to RSV infection can be reduced. Also, RSV has been linked with the development of asthma, and hence, prevention or successful treatment of RSV is expected to decrease the incidence of asthma and fatal exacerbation of asthma due to RSV. Adults infected with RSV miss work for an average of 7-9 days as opposed those with flu who miss an average of 6-7 days. Therapeutic treatment can reduce the number of absences from the work, which exceeds the flu infection. Also, prophylaxis prior to and during viral season and treatment immediately after infection can lead to a substantial decrease in hospitalization and emergency visits due to RSV infection.

RSV is one of the important viral respiratory pathogens that produce an annual epidemic of respiratory illness. In children, common diseases associated with RSV infection primarily include interstitial lung diseases, such as bronchiolitis, and asthma. RSV is estimated to cause 85% of the cases of acute bronchiolitis that affects infants and young children (Shay, D K et al. *Jama,* 1999, 282 (15):1440-6). Some children may become infected during three or four successive RSV seasons. Each year, RSV is responsible for up to an estimated 125,000 pediatric hospitalizations, with a mortality rate of approximately 2% (Heilman, C A. *J Infect Dis* 1990, 161 (3):402-6; Shay, D K et al. *J Infect Dis,* 2001, 183 (1): 16-22; Altman, C A et al. *Pediatr Cardiol,* 2000, 21 (5):433-8; Simoes, E A. *Lancet,* 1999, 354 (9181):847-52; Falsey, A R. et al. *J Infect Dis,* 1995, 172 (2):389-94). Among hospitalized infants with chronic lung and heart disease, the RSV mortality rate may be as high as 5%. Up to half of all pediatric admissions for bronchiolitis and one-quarter of admissions for pneumonia are due to RSV (La Via et al., *Clin. Pediatr. (Phila),* 32 (8):450-454, 1993). RSV is a major risk factor for a number of other health conditions, such as immuno-deficiency, cardiac arrhythmia, congenital heart disease, and unusual atrial tachycardia (Donnerstein et al., *J. Pediair.* 125 (1):23-28, 1994).

Emerging evidence also suggests that RSV is an important pathogen in profusely healthy adults as well (Hall et al., *Clin. Infect. Dis.* 33(6):792-796, 2001). In a study of 15 adults who were challenged by RSV after a natural infection, 50% were reinfected after two months; by 26 months 73% were reinfected (Fixler, D E. et al. *Pediatr Cardiol,* 1996, 17 (3):163-8). RSV infection is also clinically important in previously healthy working adults (Hogg, J C. et al. *American Journal of Respiratory & Critical Care Medicine,* 1999, 160 (5):S26-S28). In this study, of a total of 2960 18-60 year-old adults studied during 1975 to 1995, 211 (7%) acquired RSV infection; 84% of infections were symptomatic—74% upper respiratory tract infection, 26% lower respiratory tract infection and 40% were febrile. RSV is a major risk factor for the development and/or exacerbation of asthma and chronic obstructive pulmonary disorder (COPD), and about 30 million of Americans suffers from asthma and COPD.

The prevalence of bronchiolitis in infants as well as asthma and COPD has increased throughout the world, including in the United States, over the past two decades. The rates of death from asthma have increased from 0.8 per 100,000 in 1977-78 to 2.0 per 100,000 in 1991, and these rates have increased in almost all age groups in the United States (Sly, R M. *Ann Allergy.* 1994, 73 (3):259-68). Asthma is the most common cause of the admission of children to the hospital, and it is the most common chronic illness causing absence from school and work in North America (Nelson, R P, Jr., et al. *J Allergy Clin Immunol,* 1996, 98 (2):258-63). The total costs of illnesses related to asthma in 1990 were 6.2 billion, a 53% increase in direct medical expenditures and a 23% increase in indirect costs since 1985 (Weiss, K B et al. *N Engl J Med,* 1992, 326 (13):862-6). The total estimated cost in 1995 for the treatment of allergic diseases, asthma, chronic sinusitis, otitis media, and nasal polyps, was about $10 billion (Baraniuk, J N. *J Resp Dis,* 1996, 17 (S11)). Together, these diseases lead to a significant reduction in the quality of life and a tremendous economic loss.

Finally, although studies with 2-5 AS (p40) in the adenovirus system provides the "proof of concept" for the anti-RSV activity, other virus vectors, including adeno-associated vectors (Zhao, N et al. *Mol Biotechnol,* 2001, 19 (3):229-37; Monahan, P E et al. *Mol Med Today,* 2000, 6 (11):433-40; Senior, K. *Lancet,* 2002, 359 (9313):1216) can be used to express this p-40 or other 2-5 AS gene(s) for the antiviral activity.

Example 12

Gene Therapy

In the therapeutic and prophylactic methods of the present invention, the nucleotide sequence encoding 2-5 AS, or a catalytically active fragment thereof, can be administered to a patient in various ways. It should be noted that the vaccine can be administered as the compound or as pharmaceutically acceptable salt and can be administered alone or as an active ingredient in combination with pharmaceutically acceptable carriers, diluents, adjuvants and vehicles. In those cases in which the RNA virus is a virus that infects the patient's respiratory system, the compounds can be administered intranasally, bronchially, via inhalation pathways, for example. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the present invention.

It is noted that humans are treated generally longer than the mice exemplified herein, which treatment has a length proportional to the length of the disease process and drug effectiveness. The doses may be single doses or multiple doses over a period of several days, but single doses are preferred.

The carrier for gene therapy can be a solvent or dispersing medium containing, for example, water, ethanol, polyol (for example, glycerol, propylene glycol, liquid polyethylene glycol, and the like), suitable mixtures thereof, and vegetable oils.

Proper fluidity, when desired, can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives that enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Examples of delivery systems useful in the present invention include, but are not limited to: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other delivery systems and modules are well known to those skilled in the art.

A pharmacological formulation of the nucleotide sequence utilized in the present invention can be administered orally to the patient. Conventional methods such as administering the compounds in tablets, suspensions, solutions, emulsions, capsules, powders, syrups and the like are usable. Known techniques which deliver the vaccine orally or intravenously and retain the biological activity are preferred.

In one embodiment, the nucleotide sequence can be administered initially by nasal infection to increase the local levels of 2-5 AS enzymatic activity. The patient's 2-5 AS activity levels are then maintained by an oral dosage form, although other forms of administration, dependent upon the patient's condition and as indicated above, can be used. The quantity of vaccine to be administered will vary for the patient being treated and will vary from about 100 ng/kg of body weight to 100 mg/kg of body weight per day and preferably will be from 10 mg/kg to 10 mg/kg per day.

As indicated above, standard molecular biology techniques known in the art and not specifically described can be generally followed as in Sambrook et al., Molecular Cloning: A Laboratory Manual, Cold Spring Harbor Laboratory Press, New York (1989), and in Ausubel et al., Current Protocols in Molecular Biology, John Wiley and Sons, Baltimore, Md. (1989) and in Perbal, A Practical Guide to Molecular Cloning, John Wiley & Sons, New York (1988), and in Watson et al., Recombinant DNA, Scientific American Books, New York and in Birren et al. (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659; and 5,272,057, the contents of which are incorporated herein by reference in their entirety. Polymerase chain reaction (PCR) can be carried out generally as in PCR Protocols: A Guide To Methods And Applications, Academic Press, San Diego, Calif. (1990). In-situ (In-cell) PCR in combination with Flow Cytometry can be used for detection of cells containing specific DNA and mRNA sequences (Testoni et al., 1996, *Blood* 87:3822).

As used herein, the term "gene therapy" refers to the transfer of genetic material (e.g., DNA or RNA) of interest into a host to treat or prevent a genetic or acquired disease or condition phenotype. The genetic material of interest encodes a product (e.g., a protein, polypeptide, peptide or functional RNA) whose production in vivo is desired. For example, in addition to the nucleotide encoding 2-5 AS, or a catalytically active fragment thereof, the genetic material of interest can encode a hormone, receptor, or other enzyme, polypeptide or peptide of therapeutic value. For a review see, in general, the text "Gene Therapy" (*Advances in Pharmacology* 40, Academic Press, 1997).

Two basic approaches to gene therapy have evolved: (1) ex vivo and (2) in vivo gene therapy. In ex vivo gene therapy, cells are removed from a patient, and while being cultured are treated in vitro. Generally, a functional replacement gene is introduced into the cell via an appropriate gene delivery vehicle/method (transfection, transduction, homologous recombination, etc.) and an expression system as needed and then the genetically modified cells are expanded in culture and returned to the host/patient. These genetically reimplanted cells produce the transfected gene product in situ. Alternatively, a xenogenic or allogeneic donor's cells can be genetically modified with the nucleotide sequence in vitro and subsequently administered to the patient.

In in vivo gene therapy, target cells are not removed from the patient; rather, the gene to be transferred is introduced into the cells of the recipient organism in situ, that is within the recipient. Alternatively, if the host gene is defective, the gene is repaired in situ. These genetically modified cells produce the transfected gene product in situ.

The gene expression vehicle is capable of delivery/transfer of heterologous nucleic acids into a host cell. As indicated previously, the expression vehicle may include elements to control targeting, expression and transcription of the nucleotide sequence in a cell selective or tissue-specific manner, as is known in the art. It should be noted that often the 5'UTR and/or 3'UTR of the gene may be replaced by the 5'UTR and/or 3'UTR of the expression vehicle. Therefore as used herein the expression vehicle may, as needed, not include the 5'UTR and/or 3'UTR and only include the specific amino acid coding region.

The expression vehicle can include a promoter for controlling transcription of the heterologous material and can be either a constitutive or inducible promoter to allow selective transcription. Enhancers that may be required to obtain necessary transcription levels can optionally be included. Enhancers are generally any non-translated DNA sequence which works contiguously with the coding sequence (in cis) to change the basal transcription level dictated by the promoter. The expression vehicle can also include a selection gene as described herein below.

Vectors can be introduced into cells or tissues by any one of a variety of known methods within the art. Such methods can be found generally described in Sambrook et al., Molecular Cloning: A Laboratory Manual, Cold Springs Harbor Laboratory, New York (1989, 1992); in Ausubel et al., Current Protocols in Molecular Biology, John Wiley and Sons, Baltimore, Md. (1989); Chang et al., Somatic Gene Therapy, CRC Press, Ann Arbor, Mich. (1995); Vega et al., Gene Targeting, CRC Press, Ann Arbor, Mich. (1995); Vectors: A Survey of Molecular Cloning Vectors and Their Uses, Butterworths, Boston Mass. (1988); and Gilboa et al. (1986) and include, for example, stable or transient transfection, lipofection, electroporation and infection with recombinant viral vectors. In addition, see U.S. Pat. No. 4,866,042 for vectors involving the central nervous system and also U.S. Pat. Nos. 5,464,764 and 5,487,992 for positive-negative selection methods.

Introduction of nucleic acids by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

A specific example of a DNA viral vector for introducing and expressing recombinant nucleotide sequences is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes most cancers of epithelial origin as well as others. This vector as well as others that exhibit similar desired functions can be used to treat a mixed population of cells and can include, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the antibiotic gancyclovir. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types or tissue types can also be included. Such features include, for example, promoter and regulatory elements that are specific for the desired cell type or tissue type.

In addition, recombinant viral vectors are useful for in vivo expression of a desired nucleic acid because they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the present invention will depend on desired the cell type or cell types to be targeted and will be known to those skilled in the art. For example, if RSV infection is to be inhibited (i.e., treated or prevented), then a vector specific for such respiratory mucosal epithelial cells would preferably be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles that are capable of undergoing further rounds of infection. The vector's genome is also engineered to encode and express the desired recombinant nucleotide sequence. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

The recombinant vector can be administered in several ways. If viral vectors are used, for example, the procedure can take advantage of their target specificity and consequently, do not have to be administered locally at the diseased site. However, local administration can provide a quicker and more effective treatment, administration can also be performed by, for example, intravenous or subcutaneous injection into the subject. Injection of the viral vectors into a spinal fluid can also be used as a mode of administration, especially in the case of RNA virus infections of the central nervous system. Following injection, the viral vectors will circulate until they recognize host cells with the appropriate target specificity for infection.

An alternate mode of administration can be by direct inoculation locally at the site of the disease or pathological condition or by inoculation into the vascular system supplying the site with nutrients or into the spinal fluid. Local administration is advantageous because there is no dilution effect and, therefore, a smaller dose is required to achieve expression in a majority of the targeted cells. Additionally, local inoculation can alleviate the targeting requirement required with other forms of administration since a vector can be used that infects all cells in the inoculated area. If expression is desired in only a specific subset of cells within the inoculated area, then promoter and regulatory elements that are specific for the desired subset can be used to accomplish this goal. Such non-targeting vectors can be, for example, viral vectors, viral genome, plasmids, phagemids and the like. Transfection vehicles such as liposomes and colloidal polymeric particles can also be used to introduce the non-viral vectors described above into recipient cells within the inoculated area. Such transfection vehicles are known to those skilled within the art.

Direct DNA inoculations can be administered as a method of vaccination. Plasmid DNAs encoding influenza virus hemagglutinin glycoproteins have been tested for the ability to provide protection against lethal influenza challenges. In immunization trials using inoculations of purified DNA in saline, 67-95% of test mice and 25-63% of test chickens were protected against the lethal challenge. Good protection was achieved by intramuscular, intravenous and intradermal injections. In mice, 95% protection was achieved by gene gun delivery of 250-2500 times less DNA than the saline inoculations. Successful DNA vaccination by multiple routes of inoculation and the high efficiency of gene-gun delivery highlight the potential of this promising new approach to immunization. Plasmid DNAs expressing influenza virus hemagglutinin glycoproteins have been tested for their ability to raise protective immunity against lethal influenza challenges of the same subtype. In trials using two inoculations of from 50 to 300 micrograms of purified DNA in saline, 67-95% of test mice and 25-63% of test chickens have been protected against a lethal influenza challenge. Parenteral routes of inoculation that achieved good protection included intramuscular and intravenous injections. Successful mucosal routes of vaccination included DNA drops administered to the nares or trachea. By far, the most efficient DNA immunizations were achieved by using a gene gun to deliver DNA-coated gold beads to the epidermis. In mice, 95% protection was achieved by two immunizations with beads loaded with as little as 0.4 micrograms of DNA. The breadth of routes supporting successful DNA immunizations, coupled with the very small amounts of DNA required for gene-gun immunizations, highlight the potential of this remarkably simple technique for the development of subunit vaccines. In contrast to the DNA based antigen vaccines, the present invention provides the development of an intranasal gene transfer method using 2-5 AS, or a catalytically active fragment thereof, which can be used as a prophylaxis against multiple respiratory infections. In a preferred embodiment, the preventative and therapeutic method is used against respiratory RNA viral infection, most preferably against RSV.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method of increasing expression of 2'-5' oligoadenylate synthetase in a mammal, said method comprising administering to the mammal a nucleotide sequence encoding a 2'-5' oligoadenylate synthetase, or at least one enzymatically active fragment thereof, wherein the nucleotide sequence is expressed in the mammal.

2. The method of claim 1, wherein the enzymatically active fragment comprises an enzymatically active subunit of 2'-5' oligoadenylate synthetase selected from the group consisting of p40, p69, and p100.

3. The method according to claim 1, wherein the nucleotide sequence is administered to the mammal within a viral vector.

4. The method of claim 1, wherein the nucleotide sequence is administered to the mammal intranasally.

5. The method of claim 1, wherein the expression of 2'-5' oligoadenylate synthetase is increased to treat infection of the mammal by an RNA virus, and wherein the RNA virus is a type that transiently produces double-stranded RNA during intermediate replication.

6. The method of claim 5, wherein the mammal is a human.

7. The method of claim 6, wherein the human is a child.

8. The method of claim 6, wherein the human is elderly.

* * * * *

UNITED STATES PATENT AND TRADEMARK OFFICE
CERTIFICATE OF CORRECTION

PATENT NO. : 8,802,647 B2  
APPLICATION NO. : 13/621470  
DATED : August 12, 2014  
INVENTOR(S) : Shyam S. Mohapatra and Aruna K. Behera It is certified that error appears in the above-identified patent and that said Letters Patent is hereby corrected as shown below:

In the Specification

Figure 12:
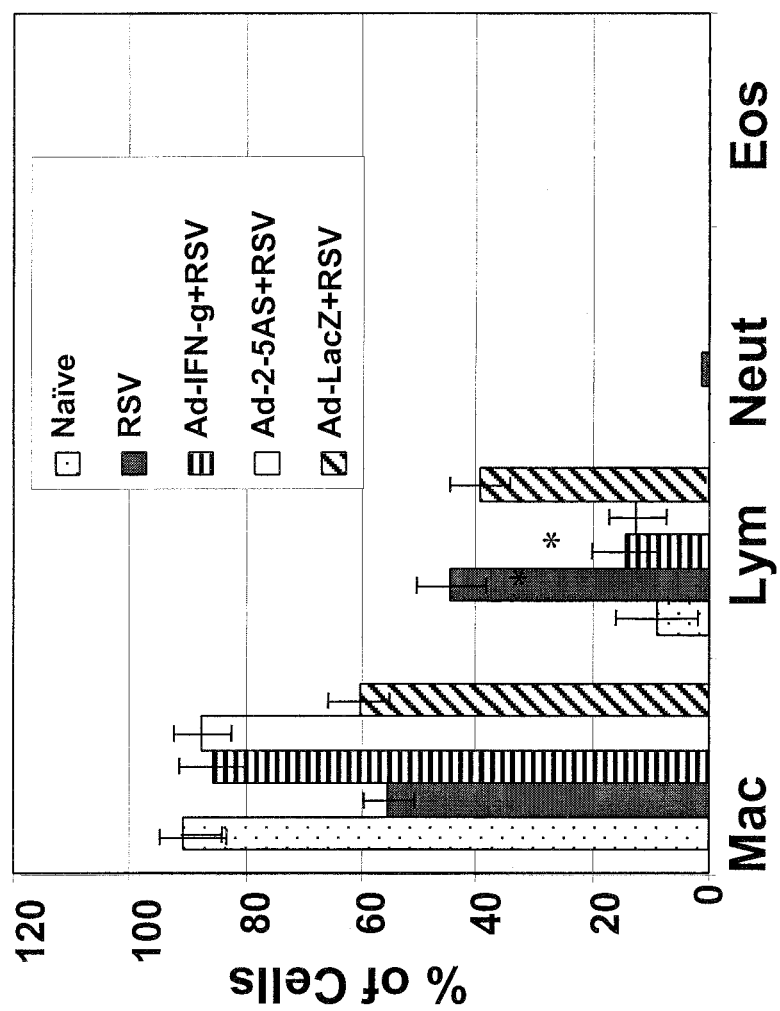
FIG. 12 shows that Ad-p40 inhibits RSV induced airway reactivity. BALB/c mice were intranasally administered with Ad-p40 and subsequently infected with RSV. AHR was measured on day 4 post-RSV infection. Ad-p40 treatment significantly decreased pulmonary inflammation.

Column 3, Line 47 through Column 4, Line 10:
"Figure 10 shows results of treatment with adenoviral vector (Ad)- 2-5AS (p40) results in attenuation of RSV replication. BALB/c mice were intranasally administered with Ad-p40 and then infected with RSV. Lungs were harvested five days post RSV infection and RSV replication was assayed by RT-PCR analysis of RSV- N gene. GAPDH was used as internal control.
Figure 11 shows that Ad-p40 attenuates RSV lung titers. Mice were intranasally given Ad-p40 and then infected with RSV. Lungs were harvested five days post RSV infection and lung homogenate was used for RSV plaque assay. Ad-LacZ was used as control.
Figure 12 shows that Ad-p40 inhibits RSV induced airway reactivity. BALB/c mice were intranasally administered with Ad-p40 and subsequently infected with RSV. AHR was measured on day 4 post-RSV infection. Ad-p40 treatment significantly decreased pulmonary inflammation.
Figures 13A-13H show that Ad-p40 overexpression normalizes macrophage and lymphocyte numbers in the lung in RSV infected mice. BAL cell differential was performed and percentages of macrophage, lymphocytes and neutrophils was determined. Both Ad-IFNg and Ad-p40 treatment reduced the lymphocyte population to normal, compared to RSV-infected mice. Histological sections from lungs were stained with hematoxylin and eosin and representative photomicrographs are shown. Sections shown are as follows: Naive mice (Figure 13A; with magnified inset Figure 13B); RSV infected mice (Figure 13C; with magnified inset, Figure 13D); Ad-p40 treated mice (Figure 13E; with magnified inset, Figure 13F); and Ad-lacZ treated mice (Figure 13G; with magnified inset, Figure 13H)."

SHOULD READ
--Figure 10 shows that Ad-p40 attenuates RSV lung titers. Mice were intranasally given Ad-p40 and then infected with RSV. Lungs were harvested five days post RSV infection and lung homogenate was used for RSV plaque assay. Ad-LacZ was used as control. RSV replication was also assayed by RT-PCR analysis of RSV- N gene. GAPDH was used as internal control (data not shown).

Signed and Sealed this
Fifth Day of May, 2015

Michelle K. Lee
*Director of the United States Patent and Trademark Office*

Figure 11 shows that Ad-p40 inhibits RSV induced airway reactivity. BALB/c mice were intranasally administered with Ad-p40 and subsequently infected with RSV. AHR was measured on day 4 post-RSV infection. Ad-p40 treatment significantly decreased pulmonary inflammation.

Figure 12 shows that Ad-p40 overexpression normalizes macrophage and lymphocyte numbers in the lung in RSV infected mice. BAL cell differential was performed and percentages of macrophage, lymphocytes and neutrophils was determined. Both Ad-IFNg and Ad-p40 treatment reduced the lymphocyte population to normal, compared to RSV-infected mice.

Figures 13A-13H show histological sections from lungs were stained with hematoxylin and eosin and representative photomicrographs are shown. Sections shown are as follows: Naive mice (Figure 13A; with magnified inset Figure 13B); RSV infected mice (Figure 13C; with magnified inset, Figure 13D); Ad-p40 treated mice (Figure 13E; with magnified inset, Figure 13F); and Ad-lacZ treated mice (Figure 13G; with magnified inset, Figure 13H).--

Column 18,
Line 51, "Pennsylavania" should read --Pennsylvania--

Column 20,
Line 65, "pH7.4" should read --pH 7.4--

Column 21,
Line 40, "50 M" should read --50 µM--

Column 23,
Line 16, "25 AS" should read --2-5 AS--

Column 27,
Line 20, "log 10 PFU/ml" should read --log10 PFU/ml--
Line 22, "log 10 PFU/ml" should read --log10 PFU/ml--

Column 30,
Line 3, "(FIG. 10)" should read --(FIG. 11)--
Line 39, "(FIGS. 12A-12H)" should read --(FIGS. 13A-13H)--

Column 31,
Line 38, "*J. Pediair.*" should read --*J. Pediatr.*--

SEQUENCE LISTING

```
<160> NUMBER OF SEQ ID NOS: 20

<210> SEQ ID NO 1
<211> LENGTH: 1203
<212> TYPE: DNA
<213> ORGANISM: Homo sapiens
<220> FEATURE:
<221> NAME/KEY: CDS
<222> LOCATION: (1)..(1203)
<223> OTHER INFORMATION:
<300> PUBLICATION INFORMATION:
<301> AUTHORS: Aissouni, Y., et al.
<302> TITLE: The cleavage/polyadenylation activity triggered by a U-rich
      motif sequence
<303> JOURNAL: J. Biol. Chem.
<304> VOLUME: 277
<305> ISSUE: 39
<306> PAGES: 35808-35814
<307> DATE: 2002
<308> DATABASE ACCESSION NUMBER: NCBI/NM_016816
<309> DATABASE ENTRY DATE: 2003-04-06
<300> PUBLICATION INFORMATION:
<301> AUTHORS: Behera, A.K., et al.
<302> TITLE: 2'-5' Oligoadenylate synthesis plays a critical role in
      interferon-gamma inhibition
<303> JOURNAL: J. Biol. Chem.
<304> VOLUME: 277
<305> ISSUE: 28
<306> PAGES: 25601-25608
<307> DATE: 2002
<308> DATABASE ACCESSION NUMBER: NCBI/NM_016816
<309> DATABASE ENTRY DATE: 2003-04-06
<300> PUBLICATION INFORMATION:
<301> AUTHORS: Sarker, S.N., et al.
<302> TITLE: Identification of the substrate-binding sites of
      2'-5'-oligoadenylate synthetase
<303> JOURNAL: J. Biol. Chem.
<304> VOLUME: 277
<305> ISSUE: 27
<306> PAGES: 24321-24330
<307> DATE: 2002
<308> DATABASE ACCESSION NUMBER: NCBI/NM_016816
<309> DATABASE ENTRY DATE: 2003-04-06
<300> PUBLICATION INFORMATION:
<301> AUTHORS: Hovnanian, A., et al.
<302> TITLE: The human 2',5'-oligoadenylate synthetase locus is composed
      of three distinct genes
<303> JOURNAL: Genomics
<304> VOLUME: 52
<305> ISSUE: 3
<306> PAGES: 267-277
<307> DATE: 1998
<308> DATABASE ACCESSION NUMBER: NCBI/NM_016816
<309> DATABASE ENTRY DATE: 2003-04-06
<300> PUBLICATION INFORMATION:
<301> AUTHORS: Renault, B., et al.
<302> TITLE: A sequence-ready physical map of a region of 12q24.1
<303> JOURNAL: Genomics
<304> VOLUME: 45
<305> ISSUE: 2
<306> PAGES: 271-278
<307> DATE: 1997
<308> DATABASE ACCESSION NUMBER: NCBI/NM_016816
<309> DATABASE ENTRY DATE: 2003-04-06
<300> PUBLICATION INFORMATION:
<301> AUTHORS: Nechiporuk, T., et al.
<302> TITLE: A high-resolution PAC and BAC map of the SCA2 region
<303> JOURNAL: Genomics
<304> VOLUME: 44
<305> ISSUE: 3
<306> PAGES: 321-329
```

```
<307> DATE: 1997
<308> DATABASE ACCESSION NUMBER: NCBI/NM_016816
<309> DATABASE ENTRY DATE: 2003-04-06
<300> PUBLICATION INFORMATION:
<301> AUTHORS: Wathelet, M.G., et al.
<302> TITLE: Cloning and chromosomal location of human genes inducible
      by type I interferon
<303> JOURNAL: Somat. Cell Mol. Genet.
<304> VOLUME: 14
<305> ISSUE: 5
<306> PAGES: 415-426
<307> DATE: 1988
<308> DATABASE ACCESSION NUMBER: NCBI/NM_016816
<309> DATABASE ENTRY DATE: 2003-04-06
<300> PUBLICATION INFORMATION:
<301> AUTHORS: Rutherford, M.N., et al.
<302> TITLE: Interferon-induced binding of nuclear factors to promoter
      elements of the 2-5A synthetase gene
<303> JOURNAL: EMBO J.
<304> VOLUME: 7
<305> ISSUE: 3
<306> PAGES: 751-759
<307> DATE: 1988
<308> DATABASE ACCESSION NUMBER: NCBI/NM_016816
<309> DATABASE ENTRY DATE: 2003-04-06
<300> PUBLICATION INFORMATION:
<301> AUTHORS: Wathelet, M.G., et al.
<302> TITLE: New inducers revealed by the promoter sequence analysis of
      two interferon-activated human genes
<303> JOURNAL: Eur. J. Biochem.
<304> VOLUME: 169
<305> ISSUE: 2
<306> PAGES: 313-321
<307> DATE: 1987
<308> DATABASE ACCESSION NUMBER: NCBI/NM_016816
<309> DATABASE ENTRY DATE: 2003-04-06
<300> PUBLICATION INFORMATION:
<301> AUTHORS: Benech, P., et al.
<302> TITLE: Interferon-responsive regulatory elements in the promoter
      of the human 2',5'-oligo(A) synthetase gene
<303> JOURNAL: Mol. Cell. Biol.
<304> VOLUME: 7
<305> ISSUE: 12
<306> PAGES: 4498-4504
<307> DATE: 1987
<308> DATABASE ACCESSION NUMBER: NCBI/NM_016816
<309> DATABASE ENTRY DATE: 2003-04-06
<300> PUBLICATION INFORMATION:
<301> AUTHORS: Hovanessian, A.G., et al.
<302> TITLE: Identification of 69-kd and 100-kd forms of 2-5A synthetase
<303> JOURNAL: EMBO J.
<304> VOLUME: 6
<305> ISSUE: 5
<306> PAGES: 1273-1280
<307> DATE: 1987
<308> DATABASE ACCESSION NUMBER: NCBI/NM_016816
<309> DATABASE ENTRY DATE: 2003-04-06
<300> PUBLICATION INFORMATION:
<301> AUTHORS: Williams, B.R., et al.
<302> TITLE: Interferon-regulated human 2-5A synthetase gene maps to
      chromosome
<303> JOURNAL: Somat. Cell Mol. Genet.
<304> VOLUME: 12
<305> ISSUE: 4
<306> PAGES: 403-408
<307> DATE: 1986
<308> DATABASE ACCESSION NUMBER: NCBI/NM_016816
<309> DATABASE ENTRY DATE: 2003-04-06
<300> PUBLICATION INFORMATION:
<301> AUTHORS: Shiojiri, S., et al.
<302> TITLE: Structure and expression of a cloned cDNA for human (2'-5')
      oligoadenylate synthetase
<303> JOURNAL: J. Biochem.
<304> VOLUME: 99
<305> ISSUE: 5
<306> PAGES: 1455-1464
<307> DATE: 1986
<308> DATABASE ACCESSION NUMBER: NCBI/NM_016816
<309> DATABASE ENTRY DATE: 2003-04-06
```

```
<300> PUBLICATION INFORMATION:
<301> AUTHORS: Wathelet, M., et al.
<302> TITLE: Full-length sequence and expression of the 42 kDa 2-5A
       synthetase
<303> JOURNAL: FEBS Lett.
<304> VOLUME: 196
<305> ISSUE: 1
<306> PAGES: 113-120
<307> DATE: 1986
<308> DATABASE ACCESSION NUMBER: NCBI/NM_016816
<309> DATABASE ENTRY DATE: 2003-04-06
<300> PUBLICATION INFORMATION:
<301> AUTHORS: Benech, P., et al.
<302> TITLE: Structure of two forms of the interferon-induced (2'-5')
       oligo A synthetase of human cells
<303> JOURNAL: EMBO J.
<304> VOLUME: 4
<305> ISSUE: 9
<306> PAGES: 2249-2256
<307> DATE: 1985
<308> DATABASE ACCESSION NUMBER: NCBI/NM_016816
<309> DATABASE ENTRY DATE: 2003-04-06
<300> PUBLICATION INFORMATION:
<301> AUTHORS: Saunders, M.E., et al.
<302> TITLE: Human 2-5A synthetase: characterization of a novel cDNA
       and corresponding gene structure
<303> JOURNAL: EMBO J.
<304> VOLUME: 4
<305> ISSUE: 7
<306> PAGES: 1761-1768
<307> DATE: 1985
<308> DATABASE ACCESSION NUMBER: NCBI/NM_016816
<309> DATABASE ENTRY DATE: 2003-04-06
<300> PUBLICATION INFORMATION:
<301> AUTHORS: Merlin, G., et al.
<302> TITLE: Molecular cloning and sequence of partial cDNA for
       interferon-induced (2'-5')oligo(A_ synthetase mRNA from human
       cells
<303> JOURNAL: Proc. Natl. Acad. Sci. U.S.A.
<304> VOLUME: 80
<305> ISSUE: 16
<306> PAGES: 4904-4908
<307> DATE: 1983
<308> DATABASE ACCESSION NUMBER: NCBI/NM_016816
<309> DATABASE ENTRY DATE: 2003-04-06

<400> SEQUENCE: 1 atg atg gat ctc aga aat acc cca gcc aaa tct ctg gac aag ttc att        48
Met Met Asp Leu Arg Asn Thr Pro Ala Lys Ser Leu Asp Lys Phe Ile
1               5                   10                  15 gaa gac tat ctc ttg cca gac acg tgt ttc cgc atg caa atc gac cat        96
Glu Asp Tyr Leu Leu Pro Asp Thr Cys Phe Arg Met Gln Ile Asp His
            20                  25                  30 gcc att gac atc atc tgt ggg ttc ctg aag gaa agg tgc ttc cga ggt       144
Ala Ile Asp Ile Ile Cys Gly Phe Leu Lys Glu Arg Cys Phe Arg Gly
        35                  40                  45 agc tcc tac cct gtg tgt gtg tcc aag gtg gta aag ggt ggc tcc tca       192
Ser Ser Tyr Pro Val Cys Val Ser Lys Val Val Lys Gly Gly Ser Ser
    50                  55                  60 ggc aag ggc acc acc ctc aga ggc cga tct gac gct gac ctg gtt gtc       240
Gly Lys Gly Thr Thr Leu Arg Gly Arg Ser Asp Ala Asp Leu Val Val
65                  70                  75                  80 ttc ctc agt cct ctc acc act ttt cag gat cag tta aat cgc cgg gga       288
Phe Leu Ser Pro Leu Thr Thr Phe Gln Asp Gln Leu Asn Arg Arg Gly
                85                  90                  95 gag ttc atc cag gaa att agg aga cag ctg gaa gcc tgt caa aga gag       336
Glu Phe Ile Gln Glu Ile Arg Arg Gln Leu Glu Ala Cys Gln Arg Glu
            100                 105                 110 aga gca ctt tcc gtg aag ttt gag gtc cag gct cca cgc tgg ggc aac       384
Arg Ala Leu Ser Val Lys Phe Glu Val Gln Ala Pro Arg Trp Gly Asn
        115                 120                 125
```

```
ccc cgt gcg ctc agc ttc gta ctg agt tcg ctc cag ctc ggg gag ggg      432
Pro Arg Ala Leu Ser Phe Val Leu Ser Ser Leu Gln Leu Gly Glu Gly
    130                 135                 140 gtg gag ttc gat gtg ctg cct gcc ttt gat gcc ctg ggt cag ttg act      480
Val Glu Phe Asp Val Leu Pro Ala Phe Asp Ala Leu Gly Gln Leu Thr
145                 150                 155                 160 ggc agc tat aaa cct aac ccc caa atc tat gtc aag ctc atc gag gag      528
Gly Ser Tyr Lys Pro Asn Pro Gln Ile Tyr Val Lys Leu Ile Glu Glu
                165                 170                 175 tgc acc gac ctg cag aaa gag ggc gag ttc tcc acc tgc ttc aca gaa      576
Cys Thr Asp Leu Gln Lys Glu Gly Glu Phe Ser Thr Cys Phe Thr Glu
            180                 185                 190 cta cag aga gac ttc ctg aag cag cgc ccc acc aag ctc aag agc ctc      624
Leu Gln Arg Asp Phe Leu Lys Gln Arg Pro Thr Lys Leu Lys Ser Leu
        195                 200                 205 atc cgc cta gtc aag cac tgg tac caa aat tgt aag aag aag ctt ggg      672
Ile Arg Leu Val Lys His Trp Tyr Gln Asn Cys Lys Lys Lys Leu Gly
    210                 215                 220 aag ctg cca cct cag tat gcc ctg gag ctc ctg acg gtc tat gct tgg      720
Lys Leu Pro Pro Gln Tyr Ala Leu Glu Leu Leu Thr Val Tyr Ala Trp
225                 230                 235                 240 gag cga ggg agc atg aaa aca cat ttc aac aca gcc caa gga ttt cgg      768
Glu Arg Gly Ser Met Lys Thr His Phe Asn Thr Ala Gln Gly Phe Arg
                245                 250                 255 acg gtc ttg gaa tta gtc ata aac tac cag caa ctc tgc atc tac tgg      816
Thr Val Leu Glu Leu Val Ile Asn Tyr Gln Gln Leu Cys Ile Tyr Trp
            260                 265                 270 aca aag tat tat gac ttt aaa aac ccc att att gaa aag tac ctg aga      864
Thr Lys Tyr Tyr Asp Phe Lys Asn Pro Ile Ile Glu Lys Tyr Leu Arg
        275                 280                 285 agg cag ctc acg aaa ccc agg cct gtg atc ctg gac ccg gcg gac cct      912
Arg Gln Leu Thr Lys Pro Arg Pro Val Ile Leu Asp Pro Ala Asp Pro
    290                 295                 300 aca gga aac ttg ggt ggt gga gac cca aag ggt tgg agg cag ctg gca      960
Thr Gly Asn Leu Gly Gly Gly Asp Pro Lys Gly Trp Arg Gln Leu Ala
305                 310                 315                 320 caa gag gct gag gcc tgg ctg aat tac cca tgc ttt aag aat tgg gat     1008
Gln Glu Ala Glu Ala Trp Leu Asn Tyr Pro Cys Phe Lys Asn Trp Asp
                325                 330                 335 ggg tcc cca gtg agc tcc tgg att ctg ctg gct gaa agc aac agt aca     1056
Gly Ser Pro Val Ser Ser Trp Ile Leu Leu Ala Glu Ser Asn Ser Thr
            340                 345                 350 gac gat gag acc gac gat ccc agg acg tat cag aaa tat ggt tac att     1104
Asp Asp Glu Thr Asp Asp Pro Arg Thr Tyr Gln Lys Tyr Gly Tyr Ile
        355                 360                 365 gga aca cat gag tac cct cat ttc tct cat aga ccc agc acg ctc cag     1152
Gly Thr His Glu Tyr Pro His Phe Ser His Arg Pro Ser Thr Leu Gln
    370                 375                 380 gca gca tcc acc cca cag gca gaa gag gac tgg acc tgc acc atc ctc     1200
Ala Ala Ser Thr Pro Gln Ala Glu Glu Asp Trp Thr Cys Thr Ile Leu
385                 390                 395                 400 tga                                                                 1203
```

<210> SEQ ID NO 2
<211> LENGTH: 400
<212> TYPE: PRT
<213> ORGANISM: Homo sapiens

<400> SEQUENCE: 2

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asp His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Arg Ala Leu Ser Val Lys Phe Glu Val Gln Ala Pro Arg Trp Gly Asn
            115                 120                 125

Pro Arg Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr
145                 150                 155                 160

Gly Ser Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
        210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Glu Lys Tyr Leu Arg
            275                 280                 285

Arg Gln Leu Thr Lys Pro Arg Pro Val Ile Leu Asp Pro Ala Asp Pro
        290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asn Ser Thr
                340                 345                 350

Asp Asp Glu Thr Asp Asp Pro Arg Thr Tyr Gln Lys Tyr Gly Tyr Ile
            355                 360                 365

Gly Thr His Glu Tyr Pro His Phe Ser His Arg Pro Ser Thr Leu Gln
        370                 375                 380

Ala Ala Ser Thr Pro Gln Ala Glu Glu Asp Trp Thr Cys Thr Ile Leu
385                 390                 395                 400

<210> SEQ ID NO 3
<211> LENGTH: 1207
<212> TYPE: DNA
```

<213> ORGANISM: Homo sapiens
<220> FEATURE:
<221> NAME/KEY: CDS
<222> LOCATION: (1)..(1206)
<223> OTHER INFORMATION:
<300> PUBLICATION INFORMATION:
<301> AUTHORS: Benech et al.
<302> TITLE: Structure of two forms of the interferon-induced (2'-5')
    oligo A synthetase human cells based on cDNAs and gene sequences
<303> JOURNAL: EMBO J.
<304> VOLUME: 4
<305> ISSUE: 9
<306> PAGES: 2249-2256
<307> DATE: 1985
<308> DATABASE ACCESSION NUMBER: NM_016816
<309> DATABASE ENTRY DATE: 2003-04-06

<400> SEQUENCE: 3

```
atg atg gat ctc aga aat acc cca gcc aaa tct ctg gac aag ttc att      48
Met Met Asp Leu Arg Asn Thr Pro Ala Lys Ser Leu Asp Lys Phe Ile
1               5                   10                  15 gaa gac tat ctc ttg cca gac acg tgt ttc cgc atg caa atc gac cat      96
Glu Asp Tyr Leu Leu Pro Asp Thr Cys Phe Arg Met Gln Ile Asp His
            20                  25                  30 gcc att gac atc atc tgt ggg ttc ctg aag gaa agg tgc ttc cga ggt     144
Ala Ile Asp Ile Ile Cys Gly Phe Leu Lys Glu Arg Cys Phe Arg Gly
        35                  40                  45 agc tcc tac cct gtg tgt gtg tcc aag gtg gta aag ggt ggc tcc tca     192
Ser Ser Tyr Pro Val Cys Val Ser Lys Val Val Lys Gly Gly Ser Ser
50                  55                  60 ggc aag ggc acc acc ctc aga ggc cga tct gac gct gac ctg gtt gtc     240
Gly Lys Gly Thr Thr Leu Arg Gly Arg Ser Asp Ala Asp Leu Val Val
65                  70                  75                  80 ttc ctc agt cct ctc acc act ttt cag gat cag tta aat cgc cgg gga     288
Phe Leu Ser Pro Leu Thr Thr Phe Gln Asp Gln Leu Asn Arg Arg Gly
                85                  90                  95 gag ttc atc cag gaa att agg aga cag ctg gaa gcc tgt caa aga gag     336
Glu Phe Ile Gln Glu Ile Arg Arg Gln Leu Glu Ala Cys Gln Arg Glu
            100                 105                 110 aga gca ctt tcc gtg aag ttt gag gtc cag gct cca cgc tgg ggc aac     384
Arg Ala Leu Ser Val Lys Phe Glu Val Gln Ala Pro Arg Trp Gly Asn
        115                 120                 125 ccc cgt gcg ctc agc ttc gta ctg agt tcg ctc cag ctc ggg gag ggg     432
Pro Arg Ala Leu Ser Phe Val Leu Ser Ser Leu Gln Leu Gly Glu Gly
130                 135                 140 gtg gag ttc gat gtg ctg cct gcc ttt gat gcc ctg ggt cag ttg act     480
Val Glu Phe Asp Val Leu Pro Ala Phe Asp Ala Leu Gly Gln Leu Thr
145                 150                 155                 160 ggc agc tat aaa cct aac ccc caa atc tat gtc aag ctc atc gag gag     528
Gly Ser Tyr Lys Pro Asn Pro Gln Ile Tyr Val Lys Leu Ile Glu Glu
                165                 170                 175 tgc acc gac ctg cag aaa gag ggc gag ttc tcc acc tgc ttc aca gaa     576
Cys Thr Asp Leu Gln Lys Glu Gly Glu Phe Ser Thr Cys Phe Thr Glu
            180                 185                 190 cta cag aga gac ttc ctg aag cag cgc ccc acc aag ctc aag agc ctc     624
Leu Gln Arg Asp Phe Leu Lys Gln Arg Pro Thr Lys Leu Lys Ser Leu
        195                 200                 205 atc cgc cta gtc aag cac tgg tac caa aat tgt aag aag aag ctt ggg     672
Ile Arg Leu Val Lys His Trp Tyr Gln Asn Cys Lys Lys Lys Leu Gly
210                 215                 220 aag ctg cca cct cag tat gcc ctg gag ctc ctg acg gtc tat gct tgg     720
Lys Leu Pro Pro Gln Tyr Ala Leu Glu Leu Leu Thr Val Tyr Ala Trp
225                 230                 235                 240
```

| | | |
|---|---|---|
| gag cga ggg agc atg aaa aca cat ttc aac aca gcc caa gga ttt cgg<br>Glu Arg Gly Ser Met Lys Thr His Phe Asn Thr Ala Gln Gly Phe Arg<br>245 250 255 | | 768 |
| acg gtc ttg gaa tta gtc ata aac tac cag caa ctc tgc atc tac tgg<br>Thr Val Leu Glu Leu Val Ile Asn Tyr Gln Gln Leu Cys Ile Tyr Trp<br>260 265 270 | | 816 |
| aca aag tat tat gac ttt aaa aac ccc att att gaa aag tac ctg aga<br>Thr Lys Tyr Tyr Asp Phe Lys Asn Pro Ile Ile Glu Lys Tyr Leu Arg<br>275 280 285 | | 864 |
| agg cag ctc acg aaa ccc agg cct gtg atc ctg gac ccg gcg gac cct<br>Arg Gln Leu Thr Lys Pro Arg Pro Val Ile Leu Asp Pro Ala Asp Pro<br>290 295 300 | | 912 |
| aca gga aac ttg ggt ggt gga gac cca aag ggt tgg agg cag ctg gca<br>Thr Gly Asn Leu Gly Gly Gly Asp Pro Lys Gly Trp Arg Gln Leu Ala<br>305 310 315 320 | | 960 |
| caa gag gct gag gcc tgg ctg aat tac cca tgc ttt aag aat tgg gat<br>Gln Glu Ala Glu Ala Trp Leu Asn Tyr Pro Cys Phe Lys Asn Trp Asp<br>325 330 335 | | 1008 |
| ggg tcc cca gtg agc tcc tgg att ctg ctg gct gaa agc aac agt aca<br>Gly Ser Pro Val Ser Ser Trp Ile Leu Leu Ala Glu Ser Asn Ser Thr<br>340 345 350 | | 1056 |
| gac gat gag acc gac gat ccc agg acg tat cag aaa tat ggt tac att<br>Asp Asp Glu Thr Asp Asp Pro Arg Thr Tyr Gln Lys Tyr Gly Tyr Ile<br>355 360 365 | | 1104 |
| gga aca cat gag tac cct cat ttc tct cat aga ccc agc acg ctc cag<br>Gly Thr His Glu Tyr Pro His Phe Ser His Arg Pro Ser Thr Leu Gln<br>370 375 380 | | 1152 |
| gca gca tcc acc cca cag gca gaa gag gac tgg acc tgc acc atc ctc<br>Ala Ala Ser Thr Pro Gln Ala Glu Glu Asp Trp Thr Cys Thr Ile Leu<br>385 390 395 400 | | 1200 |
| tga atg c<br>Met | | 1207 |

<210> SEQ ID NO 4
<211> LENGTH: 400
<212> TYPE: PRT
<213> ORGANISM: Homo sapiens

<400> SEQUENCE: 4

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Asp His
                20                  25                  30

Ala Ile Asp Ile Ile Cys Gly Phe Leu Lys Glu Arg Cys Phe Arg Gly
            35                  40                  45

Ser Ser Tyr Pro Val Cys Val Ser Lys Val Lys Gly Gly Ser Ser
        50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
                100                 105                 110

Arg Ala Leu Ser Val Lys Phe Glu Val Gln Ala Pro Arg Trp Gly Asn
            115                 120                 125

Pro Arg Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr

```
145                 150                 155                 160

Gly Ser Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
        210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Asn Pro Ile Ile Glu Lys Tyr Leu Arg
            275                 280                 285

Arg Gln Leu Thr Lys Pro Arg Pro Val Ile Leu Asp Pro Ala Asp Pro
        290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Ala Glu Ser Asn Ser Thr
                340                 345                 350

Asp Asp Glu Thr Asp Asp Pro Arg Thr Tyr Gln Lys Tyr Gly Tyr Ile
            355                 360                 365

Gly Thr His Glu Tyr Pro His Phe Ser His Arg Pro Ser Thr Leu Gln
        370                 375                 380

Ala Ala Ser Thr Pro Gln Ala Glu Glu Asp Trp Thr Cys Thr Ile Leu
385                 390                 395                 400

<210> SEQ ID NO 5
<211> LENGTH: 2064
<212> TYPE: DNA
<213> ORGANISM: Homo sapiens
<220> FEATURE:
<221> NAME/KEY: CDS
<222> LOCATION: (1)..(2064)
<223> OTHER INFORMATION:
<300> PUBLICATION INFORMATION:
<301> AUTHORS: Hovnanian, A., et al.
<302> TITLE: The human 2', 5'-oligoadenylate synthetase locus is
       composed of three distinct genes
<303> JOURNAL: Genomics
<304> VOLUME: 52
<305> ISSUE: 3
<306> PAGES: 267-277
<307> DATE: 1998
<308> DATABASE ACCESSION NUMBER: NCBI/NM_002535
<309> DATABASE ENTRY DATE: 2003-04-03
<300> PUBLICATION INFORMATION:
<301> AUTHORS: Marie, I. and Hovanessian, A.G.
<302> TITLE: The 69-kDa 2-5A synthetase is composed of two homologous
       and adjacent functional domains
<303> JOURNAL: J. Biol. Chem.
<304> VOLUME: 267
<305> ISSUE: 14
<306> PAGES: 9933-9939
<307> DATE: 1992
<308> DATABASE ACCESSION NUMBER: NCBI/NM_002535
<309> DATABASE ENTRY DATE: 2003-04-03
<300> PUBLICATION INFORMATION:
```

```
<301> AUTHORS: Marie, I., et al.
<302> TITLE: Differential expression and distinct structure of 69- and
      100-kDa forms of 2-5A synthetase
<303> JOURNAL: J. Biol. Chem.
<304> VOLUME: 265
<305> ISSUE: 30
<306> PAGES: 18601-18607
<307> DATE: 1990
<308> DATABASE ACCESSION NUMBER: NCBI/NM_002535
<309> DATABASE ENTRY DATE: 2003-04-03
<300> PUBLICATION INFORMATION:
<301> AUTHORS: Marie, I., et al.
<302> TITLE: Preparation and characterization of polyclonal antibodies
      specific for the 69 and 100 k-dalton forms of human 2-5A
      synthetase
<303> JOURNAL: Biochem. Biophys. Res. Commun.
<304> VOLUME: 160
<305> ISSUE: 2
<306> PAGES: 580-587
<307> DATE: 1989
<308> DATABASE ACCESSION NUMBER: NCBI/NM_002535
<309> DATABASE ENTRY DATE: 2003-04-03
<300> PUBLICATION INFORMATION:
<301> AUTHORS: Hovanessian, A.G., et al.
<302> TITLE: Characterization of 69- and 100-kDa forms of
      2-5A-synthetase from interferon-treated human cells
<303> JOURNAL: J. Biol. Chem.
<304> VOLUME: 263
<305> ISSUE: 10
<306> PAGES: 4959
<307> DATE: 1988
<308> DATABASE ACCESSION NUMBER: NCBI/NM_002535
<309> DATABASE ENTRY DATE: 2003-04-03
<300> PUBLICATION INFORMATION:
<301> AUTHORS: Hovanessian, A.G., et al.
<302> TITLE: Identification of 69-kd and 100-kd forms of 2-5A synthetase
<303> JOURNAL: EMBO J.
<304> VOLUME: 6
<305> ISSUE: 5
<306> PAGES: 1273-1280
<307> DATE: 1987
<308> DATABASE ACCESSION NUMBER: NCBI/NM_002535
<309> DATABASE ENTRY DATE: 2003-04-03

<400> SEQUENCE: 5 atg gga aat ggg gag tcc cag ctg tcc tcg gtg cct gct cag aag ctg      48
Met Gly Asn Gly Glu Ser Gln Leu Ser Ser Val Pro Ala Gln Lys Leu
1               5                   10                  15 ggt tgg ttt atc cag gaa tac ctg aag ccc tac gaa gaa tgt cag aca      96
Gly Trp Phe Ile Gln Glu Tyr Leu Lys Pro Tyr Glu Glu Cys Gln Thr
            20                  25                  30 ctg atc gac gag atg gtg aac acc atc tgt gac gtc tgc agg aac ccc     144
Leu Ile Asp Glu Met Val Asn Thr Ile Cys Asp Val Cys Arg Asn Pro
        35                  40                  45 gaa cag ttc ccc ctg gtg cag gga gtg gcc ata ggt ggc tcc tat gga     192
Glu Gln Phe Pro Leu Val Gln Gly Val Ala Ile Gly Gly Ser Tyr Gly
    50                  55                  60 cgg aaa aca gtc tta aga ggc aac tcc gat ggt acc ctt gtc ctt ttc     240
Arg Lys Thr Val Leu Arg Gly Asn Ser Asp Gly Thr Leu Val Leu Phe
65                  70                  75                  80 ttc agt gac tta aaa caa ttc cag gat cag aag aga agc caa cgt gac     288
Phe Ser Asp Leu Lys Gln Phe Gln Asp Gln Lys Arg Ser Gln Arg Asp
                85                  90                  95 atc ctc gat aaa act ggg gat aag ctg aag ttc tgt ctg ttc acg aag     336
Ile Leu Asp Lys Thr Gly Asp Lys Leu Lys Phe Cys Leu Phe Thr Lys
            100                 105                 110 tgg ttg aaa aac aat ttc gag atc cag aag tcc ctt gat ggg tcc acc     384
Trp Leu Lys Asn Asn Phe Glu Ile Gln Lys Ser Leu Asp Gly Ser Thr
        115                 120                 125 atc cag gtg ttc aca aaa aat cag aga atc tct ttc gag gtg ctg gcc     432
```

```
Ile Gln Val Phe Thr Lys Asn Gln Arg Ile Ser Phe Glu Val Leu Ala
    130                 135                 140 gcc ttc aac gct ctg agc tta aat gat aat ccc agc ccc tgg atc tat      480
Ala Phe Asn Ala Leu Ser Leu Asn Asp Asn Pro Ser Pro Trp Ile Tyr
145                 150                 155                 160 cga gag ctc aaa aga tcc ttg gat aag aca aat gcc agt cct ggt gag      528
Arg Glu Leu Lys Arg Ser Leu Asp Lys Thr Asn Ala Ser Pro Gly Glu
                165                 170                 175 ttt gca gtc tgc ttc act gaa ctc cag cag aag ttt ttt gac aac cgt      576
Phe Ala Val Cys Phe Thr Glu Leu Gln Gln Lys Phe Phe Asp Asn Arg
            180                 185                 190 cct gga aaa cta aag gat ttg atc ctc ttg ata aag cac tgg cat caa      624
Pro Gly Lys Leu Lys Asp Leu Ile Leu Leu Ile Lys His Trp His Gln
        195                 200                 205 cag tgc cag aaa aaa atc aag gat tta ccc tcg ctg tct ccg tat gcc      672
Gln Cys Gln Lys Lys Ile Lys Asp Leu Pro Ser Leu Ser Pro Tyr Ala
    210                 215                 220 ctg gag ctg ctt acg gtg tat gcc tgg gaa cag ggg tgc aga aaa gac      720
Leu Glu Leu Leu Thr Val Tyr Ala Trp Glu Gln Gly Cys Arg Lys Asp
225                 230                 235                 240 aac ttt gac att gct gaa ggc gtc aga acg gtt ctg gag ctg atc aaa      768
Asn Phe Asp Ile Ala Glu Gly Val Arg Thr Val Leu Glu Leu Ile Lys
                245                 250                 255 tgc cag gag aag ctg tgt atc tat tgg atg gtc aac tac aac ttt gaa      816
Cys Gln Glu Lys Leu Cys Ile Tyr Trp Met Val Asn Tyr Asn Phe Glu
            260                 265                 270 gat gag acc atc agg aac atc ctg ctg cac cag ctc caa tca gcg agg      864
Asp Glu Thr Ile Arg Asn Ile Leu Leu His Gln Leu Gln Ser Ala Arg
        275                 280                 285 cca gta atc ttg gat cca gtt gac cca acc aat aat gtg agt gga gat      912
Pro Val Ile Leu Asp Pro Val Asp Pro Thr Asn Asn Val Ser Gly Asp
    290                 295                 300 aaa ata tgc tgg caa tgg ctg aaa aaa gaa gct caa acc tgg ttg act      960
Lys Ile Cys Trp Gln Trp Leu Lys Lys Glu Ala Gln Thr Trp Leu Thr
305                 310                 315                 320 tct ccc aac ctg gat aat gag tta cct gca cca tct tgg aat gtc ctg     1008
Ser Pro Asn Leu Asp Asn Glu Leu Pro Ala Pro Ser Trp Asn Val Leu
                325                 330                 335 cct gca cca ctc ttc acg acc cca ggc cac ctt ctg gat aag ttc atc     1056
Pro Ala Pro Leu Phe Thr Thr Pro Gly His Leu Leu Asp Lys Phe Ile
            340                 345                 350 aag gag ttt ctc cag ccc aac aaa tgc ttc cta gag cag att gac agt     1104
Lys Glu Phe Leu Gln Pro Asn Lys Cys Phe Leu Glu Gln Ile Asp Ser
        355                 360                 365 gct gtt aac atc atc cgt aca ttc ctt aaa gaa aac tgc ttc cga caa     1152
Ala Val Asn Ile Ile Arg Thr Phe Leu Lys Glu Asn Cys Phe Arg Gln
    370                 375                 380 tca aca gcc aag atc cag att gtc cgg gga gga tca acc gcc aaa ggc     1200
Ser Thr Ala Lys Ile Gln Ile Val Arg Gly Gly Ser Thr Ala Lys Gly
385                 390                 395                 400 aca gct ctg aag act ggc tct gat gcc gat ctc gtc gtg ttc cat aac     1248
Thr Ala Leu Lys Thr Gly Ser Asp Ala Asp Leu Val Val Phe His Asn
                405                 410                 415 tca ctt aaa agc tac acc tcc caa aaa aac gag cgg cac aaa atc gtc     1296
Ser Leu Lys Ser Tyr Thr Ser Gln Lys Asn Glu Arg His Lys Ile Val
            420                 425                 430 aag gaa atc cat gaa cag ctg aaa gcc ttt tgg agg gag aag gag gag     1344
Lys Glu Ile His Glu Gln Leu Lys Ala Phe Trp Arg Glu Lys Glu Glu
        435                 440                 445
```

```
gag ctt gaa gtc agc ttt gag cct ccc aag tgg aag gct ccc agg gtg    1392
Glu Leu Glu Val Ser Phe Glu Pro Pro Lys Trp Lys Ala Pro Arg Val
    450                 455                 460 ctg agc ttc tct ctg aaa tcc aaa gtc ctc aac gaa agt gtc agc ttt    1440
Leu Ser Phe Ser Leu Lys Ser Lys Val Leu Asn Glu Ser Val Ser Phe
465                 470                 475                 480 gat gtg ctt cct gcc ttt aat gca ctg ggt cag ctg agt tct ggc tcc    1488
Asp Val Leu Pro Ala Phe Asn Ala Leu Gly Gln Leu Ser Ser Gly Ser
                485                 490                 495 aca ccc agc ccc gag gtt tat gca ggg ctc att gat ctg tat aaa tcc    1536
Thr Pro Ser Pro Glu Val Tyr Ala Gly Leu Ile Asp Leu Tyr Lys Ser
500                 505                 510 tcg gac ctc ccg gga gga gag ttt tct acc tgt ttc aca gtc ctg cag    1584
Ser Asp Leu Pro Gly Gly Glu Phe Ser Thr Cys Phe Thr Val Leu Gln
            515                 520                 525 cga aac ttc att cgc tcc cgg ccc acc aaa cta aag gat tta att cgc    1632
Arg Asn Phe Ile Arg Ser Arg Pro Thr Lys Leu Lys Asp Leu Ile Arg
        530                 535                 540 ctg gtg aag cac tgg tac aaa gag tgt gaa agg aaa ctg aag cca aag    1680
Leu Val Lys His Trp Tyr Lys Glu Cys Glu Arg Lys Leu Lys Pro Lys
545                 550                 555                 560 ggg tct ttg ccc cca aag tat gcc ttg gag ctg ctc acc atc tat gcc    1728
Gly Ser Leu Pro Pro Lys Tyr Ala Leu Glu Leu Leu Thr Ile Tyr Ala
                565                 570                 575 tgg gag cag ggg agt gga gtg ccg gat ttt gac act gca gaa ggt ttc    1776
Trp Glu Gln Gly Ser Gly Val Pro Asp Phe Asp Thr Ala Glu Gly Phe
            580                 585                 590 cgg aca gtc ctg gag ctg gtc aca caa tat cag cag ctc ggc atc ttc    1824
Arg Thr Val Leu Glu Leu Val Thr Gln Tyr Gln Gln Leu Gly Ile Phe
        595                 600                 605 tgg aag gtc aat tac aac ttt gaa gat gag acc gtg agg aag ttt cta    1872
Trp Lys Val Asn Tyr Asn Phe Glu Asp Glu Thr Val Arg Lys Phe Leu
    610                 615                 620 ctg agc cag ttg cag aaa acc agg cct gtg atc ttg gac cca ggc gaa    1920
Leu Ser Gln Leu Gln Lys Thr Arg Pro Val Ile Leu Asp Pro Gly Glu
625                 630                 635                 640 ccc aca ggt gac gtg ggt gga ggg gac cgt tgg tgt tgg cat ctt ctg    1968
Pro Thr Gly Asp Val Gly Gly Gly Asp Arg Trp Cys Trp His Leu Leu
                645                 650                 655 gac aaa gaa gca aag gtt agg tta tcc tct ccc tgc ttc aag gat ggg    2016
Asp Lys Glu Ala Lys Val Arg Leu Ser Ser Pro Cys Phe Lys Asp Gly
            660                 665                 670 act gga aac cca ata cca cct tgg aaa gtg ccg gta aaa gtc atc taa    2064
Thr Gly Asn Pro Ile Pro Pro Trp Lys Val Pro Val Lys Val Ile
        675                 680                 685

<210> SEQ ID NO 6
<211> LENGTH: 687
<212> TYPE: PRT
<213> ORGANISM: Homo sapiens

<400> SEQUENCE: 6

Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Cys Arg Asn Pro
        35                  40                  45

Glu Gln Phe Pro Leu Val Gln Gly Val Ala Ile Gly Gly Ser Tyr Gly
    50                  55                  60
```

```
Arg Lys Thr Val Leu Arg Gly Asn Ser Asp Gly Thr Leu Val Leu Phe
 65                  70                  75                  80

Phe Ser Asp Leu Lys Gln Phe Gln Asp Gln Lys Arg Ser Gln Arg Asp
                 85                  90                  95

Ile Leu Asp Lys Thr Gly Asp Lys Leu Lys Phe Cys Leu Phe Thr Lys
                100                 105                 110

Trp Leu Lys Asn Asn Phe Glu Ile Gln Lys Ser Leu Asp Gly Ser Thr
            115                 120                 125

Ile Gln Val Phe Thr Lys Asn Gln Arg Ile Ser Phe Glu Val Leu Ala
        130                 135                 140

Ala Phe Asn Ala Leu Ser Leu Asn Asp Asn Pro Ser Pro Trp Ile Tyr
145                 150                 155                 160

Arg Glu Leu Lys Arg Ser Leu Asp Lys Thr Asn Ala Ser Pro Gly Glu
                165                 170                 175

Phe Ala Val Cys Phe Thr Glu Leu Gln Gln Lys Phe Phe Asp Asn Arg
                180                 185                 190

Pro Gly Lys Leu Lys Asp Leu Ile Leu Leu Ile Lys His Trp His Gln
            195                 200                 205

Gln Cys Gln Lys Ile Lys Asp Leu Pro Ser Leu Ser Pro Tyr Ala
        210                 215                 220

Leu Glu Leu Leu Thr Val Tyr Ala Trp Glu Gln Gly Cys Arg Lys Asp
225                 230                 235                 240

Asn Phe Asp Ile Ala Glu Gly Val Arg Thr Val Leu Glu Leu Ile Lys
                245                 250                 255

Cys Gln Glu Lys Leu Cys Ile Tyr Trp Met Val Asn Tyr Asn Phe Glu
                260                 265                 270

Asp Glu Thr Ile Arg Asn Ile Leu Leu His Gln Leu Gln Ser Ala Arg
            275                 280                 285

Pro Val Ile Leu Asp Pro Val Asp Pro Thr Asn Asn Val Ser Gly Asp
        290                 295                 300

Lys Ile Cys Trp Gln Trp Leu Lys Lys Glu Ala Gln Thr Trp Leu Thr
305                 310                 315                 320

Ser Pro Asn Leu Asp Asn Glu Leu Pro Ala Pro Ser Trp Asn Val Leu
                325                 330                 335

Pro Ala Pro Leu Phe Thr Thr Pro Gly His Leu Leu Asp Lys Phe Ile
                340                 345                 350

Lys Glu Phe Leu Gln Pro Asn Lys Cys Phe Leu Glu Gln Ile Asp Ser
            355                 360                 365

Ala Val Asn Ile Ile Arg Thr Phe Leu Lys Glu Asn Cys Phe Arg Gln
        370                 375                 380

Ser Thr Ala Lys Ile Gln Ile Val Arg Gly Gly Ser Thr Ala Lys Gly
385                 390                 395                 400

Thr Ala Leu Lys Thr Gly Ser Asp Ala Asp Leu Val Val Phe His Asn
                405                 410                 415

Ser Leu Lys Ser Tyr Thr Ser Gln Lys Asn Glu Arg His Lys Ile Val
                420                 425                 430

Lys Glu Ile His Glu Gln Leu Lys Ala Phe Trp Arg Glu Lys Glu Glu
            435                 440                 445

Glu Leu Glu Val Ser Phe Glu Pro Pro Lys Trp Lys Ala Pro Arg Val
        450                 455                 460

Leu Ser Phe Ser Leu Lys Ser Lys Val Leu Asn Glu Ser Val Ser Phe
465                 470                 475                 480
```

Asp Val Leu Pro Ala Phe Asn Ala Leu Gly Gln Leu Ser Ser Gly Ser
                485                 490                 495

Thr Pro Ser Pro Glu Val Tyr Ala Gly Leu Ile Asp Leu Tyr Lys Ser
            500                 505                 510

Ser Asp Leu Pro Gly Gly Glu Phe Ser Thr Cys Phe Thr Val Leu Gln
            515                 520                 525

Arg Asn Phe Ile Arg Ser Arg Pro Thr Lys Leu Lys Asp Leu Ile Arg
            530                 535                 540

Leu Val Lys His Trp Tyr Lys Glu Cys Glu Arg Lys Leu Lys Pro Lys
545                 550                 555                 560

Gly Ser Leu Pro Pro Lys Tyr Ala Leu Glu Leu Leu Thr Ile Tyr Ala
                565                 570                 575

Trp Glu Gln Gly Ser Gly Val Pro Asp Phe Asp Thr Ala Glu Gly Phe
                580                 585                 590

Arg Thr Val Leu Glu Leu Val Thr Gln Tyr Gln Gln Leu Gly Ile Phe
            595                 600                 605

Trp Lys Val Asn Tyr Asn Phe Glu Asp Glu Thr Val Arg Lys Phe Leu
            610                 615                 620

Leu Ser Gln Leu Gln Lys Thr Arg Pro Val Ile Leu Asp Pro Gly Glu
625                 630                 635                 640

Pro Thr Gly Asp Val Gly Gly Asp Arg Trp Cys Trp His Leu Leu
                645                 650                 655

Asp Lys Glu Ala Lys Val Arg Leu Ser Ser Pro Cys Phe Lys Asp Gly
                660                 665                 670

Thr Gly Asn Pro Ile Pro Pro Trp Lys Val Pro Val Lys Val Ile
                675                 680                 685

<210> SEQ ID NO 7
<211> LENGTH: 2186
<212> TYPE: DNA
<213> ORGANISM: Homo sapiens
<300> PUBLICATION INFORMATION:
<301> AUTHORS: Marie, I. and Hovanessian, A.G.
<302> TITLE: The 69-kDa 2-5A synthetase is composed of two homologous
       and adjacent functional domains
<303> JOURNAL: J. Biol. Chem.
<304> VOLUME: 267
<305> ISSUE: 14
<306> PAGES: 9933-9939
<307> DATE: 1992
<308> DATABASE ACCESSION NUMBER: (unknown)
<309> DATABASE ENTRY DATE: 2003-04-03

<400> SEQUENCE: 7
atgggaaatg gggagtccca gctgtcctcg gtgcctgctc agaagctggg ttggtttatc      60
caggaatacc tgaagcccta cgaagaatgt cagacactga tcgacgagat ggtgaacacc     120
atctgtgacg tctgcaggaa ccccgaacag ttccccctgg tgcagggagt ggccataggt     180
ggctcctatg gacggaaaac agtcttaaga ggcaactccg atggtaccct tgtccttttc     240
ttcagtgact taaacaatt ccaggatcag aagagaagcc aacgtgacat cctcgataaa     300
actggggata agctgaagtt ctgtctgttc acgaagtggt tgaaaaacaa tttcgagatc     360
cagaagtccc ttgatgggtc caccatccag gtgttcacaa aaaatcagag aatctctttc     420
gaggtgctgg ccgccttcaa cgctctgagc ttaaatgata tcccagcccc ctggatctat     480
cgagagctca aagatccett ggataagaca aatgccagtc ctggtgagtt tgcagtctgc     540
ttcactgaac tccagcagaa gttttttgac aaccgtcctg aaaaactaaa ggatttgatc     600
ctcttgataa agcactggca tcaacagtgc cagaaaaaaa tcaaggattt accctcgctg     660

-continued

```
tctccgtatg ccctggagct gcttacggtg tatgcctggg aacagggggtg cagaaaagac    720 aactttgaca ttgctgaagg cgtcagaacg gttctggagc tgatcaaatg ccaggagaag    780
ctgtgtatct attggatggt caactacaac tttgaagatg agaccatcag gaacatcctg    840
ctgcaccagc tccaatcagc gaggccagta atcttggatc cagttgaccc aaccaataat    900
gtgagtggag ataaaatatg ctggcaatgg ctgaaaaaag aagctcaaac ctggttgact    960
tctcccaacc tggataatga gttacctgca ccatcttgga atgtcctgcc tgcaccactc   1020
ttcacgaccc caggccacct tctggataag ttcatcaagg agtttctcca gcccaacaaa   1080
tgcttcctag agcagattga cagtgctgtt aacatcatcc gtacattcct aaagaaaaac   1140
tgcttccgac aatcaacagc caagatccag attgtccggg gaggatcaac cgccaaaggc   1200
acagctctga agactggctc tgatgccgat ctcgtcgtgt ccataactc  acttaaaagc   1260 tacacctccc aaaaaaacga gcggcacaaa atcgtcaagg aaatccatga acagctgaaa   1320
gccttttgga gggagaagga ggaggagctt gaagtcagct ttgagcctcc caagtggaag   1380
gctcccaggg tgctgagctt ctctctgaaa tccaaagtcc tcaacgaaag tgtcagcttt   1440
gatgtgcttc ctgccttaa tgcactgggt cagctgagtt ctggctccac acccagcccc   1500
gaggtttatg cagggctcat tgatctgtat aaatcctcgg acctcccggg aggagagttt   1560
tctacctgtt tcacagtcct gcagcgaaac ttcattcgct cccggccac  caaactaaag   1620 gatttaattc gcctggtgaa gcactggtac aaagagtgtg aaaggaaact gaagccaaag   1680
gggtctttgc ccccaaagta tgccttggag ctgctcacca tctatgcctg ggagcagggg   1740
agtggagtgc cggattttga cactgcagaa ggtttccgga cagtcctgga gctggtcaca   1800
caatatcagc agctcggcat cttctggaag gtcaattaca actttgaaga tgagaccgtg   1860
aggaagtttc tactgagcca gttgcagaaa accaggcctg tgatcttgga cccaggcgaa   1920
cccacaggtg acgtgggtgg aggggaccgt tggtgttggc atcttctgga caaagaagca   1980
aaggttaggt tatcctctcc ctgcttcaag gatgggactg aaacccaat  accaccttgg   2040 aaagtgccga caatgcagac accaggaagt tgtggagcta ggattccatc ctattgtcaa   2100
tgagatgttg tcatccagaa gccatagaat cctgaataat aattctaaaa gaaacttctg   2160
gagatcatct ggcaatcgct tttaaa                                         2186
```

<210> SEQ ID NO 8
<211> LENGTH: 727
<212> TYPE: PRT
<213> ORGANISM: Homo sapiens

<400> SEQUENCE: 8

Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Cys Arg Asn Pro
        35                  40                  45

Glu Gln Phe Pro Leu Val Gln Gly Val Ala Ile Gly Gly Ser Tyr Gly
    50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

```
Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Ser Thr
        115                 120                 125

Ile Gln Val Phe Thr Lys Asn Gln Arg Ile Ser Phe Glu Val Leu Ala
    130                 135                 140

Ala Phe Asn Ala Leu Ser Leu Asn Asp Asn Pro Ser Pro Trp Ile Tyr
145                 150                 155                 160

Arg Glu Leu Lys Arg Ser Leu Asp Lys Thr Asn Ala Ser Pro Gly Glu
                165                 170                 175

Phe Ala Val Cys Phe Thr Glu Leu Gln Gln Lys Phe Phe Asp Asn Arg
            180                 185                 190

Pro Gly Lys Leu Lys Asp Leu Ile Leu Leu Ile Lys His Trp His Gln
        195                 200                 205

Gln Cys Gln Lys Lys Ile Lys Asp Leu Pro Ser Leu Ser Pro Tyr Ala
    210                 215                 220

Leu Glu Leu Leu Thr Val Tyr Ala Trp Glu Gln Gly Cys Arg Lys Asp
225                 230                 235                 240

Asn Phe Asp Ile Ala Glu Gly Val Arg Thr Val Leu Glu Leu Ile Lys
                245                 250                 255

Cys Gln Glu Lys Leu Cys Ile Tyr Trp Met Val Asn Tyr Asn Phe Glu
            260                 265                 270

Asp Glu Thr Ile Arg Asn Ile Leu His Gln Leu Gln Ser Ala Arg
        275                 280                 285

Pro Val Ile Leu Asp Pro Val Asp Pro Thr Asn Asn Val Ser Gly Asp
    290                 295                 300

Lys Ile Cys Trp Gln Trp Leu Lys Lys Glu Ala Gln Thr Trp Leu Thr
305                 310                 315                 320

Ser Pro Asn Leu Asp Asn Glu Leu Pro Ala Pro Ser Trp Asn Val Leu
                325                 330                 335

Pro Ala Pro Leu Phe Thr Thr Pro Gly His Leu Leu Asp Lys Phe Ile
            340                 345                 350

Lys Glu Phe Leu Gln Pro Asn Lys Cys Phe Leu Glu Gln Ile Asp Ser
        355                 360                 365

Ala Val Asn Ile Ile Arg Thr Phe Leu Lys Glu Asn Cys Phe Arg Gln
    370                 375                 380

Ser Thr Ala Lys Ile Gln Ile Val Arg Gly Gly Ser Thr Ala Lys Gly
385                 390                 395                 400

Thr Ala Leu Lys Thr Gly Ser Asp Ala Asp Leu Val Val Phe His Asn
                405                 410                 415

Ser Leu Lys Ser Tyr Thr Ser Gln Lys Asn Glu Arg His Lys Ile Val
            420                 425                 430

Lys Glu Ile His Glu Gln Leu Lys Ala Phe Trp Arg Glu Lys Glu Glu
        435                 440                 445

Glu Leu Glu Val Ser Phe Glu Pro Pro Lys Trp Lys Ala Pro Arg Val
    450                 455                 460

Leu Ser Phe Ser Leu Lys Ser Lys Val Leu Asn Glu Ser Val Ser Phe
465                 470                 475                 480

Asp Val Leu Pro Ala Phe Asn Ala Leu Gly Gln Leu Ser Ser Gly Ser
                485                 490                 495

Thr Pro Ser Pro Glu Val Tyr Ala Gly Leu Ile Asp Leu Tyr Lys Ser
            500                 505                 510

Ser Asp Leu Pro Gly Gly Glu Phe Ser Thr Cys Phe Thr Val Leu Gln
```

```
                515                 520                 525
Arg Asn Phe Ile Arg Ser Arg Pro Thr Lys Leu Lys Asp Leu Ile Arg
    530                 535                 540

Leu Val Lys His Trp Tyr Lys Glu Cys Glu Arg Lys Leu Lys Pro Lys
545                 550                 555                 560

Gly Ser Leu Pro Pro Lys Tyr Ala Leu Glu Leu Leu Thr Ile Tyr Ala
                565                 570                 575

Trp Glu Gln Gly Ser Gly Val Pro Asp Phe Asp Thr Ala Glu Gly Phe
            580                 585                 590

Arg Thr Val Leu Glu Leu Val Thr Gln Tyr Gln Gln Leu Gly Ile Phe
        595                 600                 605

Trp Lys Val Asn Tyr Asn Phe Glu Asp Glu Thr Val Arg Lys Phe Leu
    610                 615                 620

Leu Ser Gln Leu Gln Lys Thr Arg Pro Val Ile Leu Asp Pro Gly Glu
625                 630                 635                 640

Pro Thr Gly Asp Val Gly Gly Asp Arg Trp Cys Trp His Leu Leu
                645                 650                 655

Asp Lys Glu Ala Lys Val Arg Leu Ser Ser Pro Cys Phe Lys Asp Gly
            660                 665                 670

Thr Gly Asn Pro Ile Pro Pro Trp Lys Val Pro Thr Met Gln Thr Pro
        675                 680                 685

Gly Ser Cys Gly Ala Arg Ile His Pro Ile Val Asn Glu Met Phe Ser
    690                 695                 700

Ser Arg Ser His Arg Ile Leu Asn Asn Asn Ser Lys Arg Asn Phe Thr
705                 710                 715                 720

Arg Ser Ser Gly Asn Arg Phe
                725

<210> SEQ ID NO 9
<211> LENGTH: 3264
<212> TYPE: DNA
<213> ORGANISM: Homo sapiens
<220> FEATURE:
<221> NAME/KEY: CDS
<222> LOCATION: (1)..(3264)
<223> OTHER INFORMATION:
<300> PUBLICATION INFORMATION:
<301> AUTHORS: Rebouillat, D., et al.
<302> TITLE: The 100-kDa 2',5'-oligoadenylate synthetase catalyzing
      preferentially the synthesis of dimeric pppA2'p5'A molecules
<303> JOURNAL: J. Biol. Chem.
<304> VOLUME: 274
<305> ISSUE: 3
<306> PAGES: 1557-1565
<307> DATE: 1999
<308> DATABASE ACCESSION NUMBER: NCBI/AF_063613
<309> DATABASE ENTRY DATE: 1999-05-04
<300> PUBLICATION INFORMATION:
<301> AUTHORS: Rebouillat, D. and Hovanessian, A.G.
<302> TITLE: Direct Submission
<303> JOURNAL: Submitted (07-May-1998) Dept.of Aids and Retroviruses,
      Institut Pasteur
<304> VOLUME: 0
<305> ISSUE: 0
<306> PAGES: 0
<307> DATE: 1998
<308> DATABASE ACCESSION NUMBER: NCBI/AF_063613
<309> DATABASE ENTRY DATE: 1999-05-04

<400> SEQUENCE: 9 atg gac ttg tac agc acc ccg gcc gct gcg ctg gac agg ttc gtg gcc    48
Met Asp Leu Tyr Ser Thr Pro Ala Ala Ala Leu Asp Arg Phe Val Ala
1               5                  10                  15
```

| | | |
|---|---|---|
| aga agg ctg cag ccg cgg aag gag ttc gta gag aag gcg cgg cgc gct<br>Arg Arg Leu Gln Pro Arg Lys Glu Phe Val Glu Lys Ala Arg Arg Ala<br>20 25 30 | | 96 |
| ctg ggc gcc ctg gcc gct gcc ctg agg gag cgc ggg ggc cgc ctc ggt<br>Leu Gly Ala Leu Ala Ala Ala Leu Arg Glu Arg Gly Gly Arg Leu Gly<br>35 40 45 | | 144 |
| gct gct gcc ccg cgg gtg ctg aaa act gtc aag gga ggc tcc tcg ggc<br>Ala Ala Ala Pro Arg Val Leu Lys Thr Val Lys Gly Gly Ser Ser Gly<br>50 55 60 | | 192 |
| cgg ggc aca gct ctc aag ggt ggc tgt gat tct gaa ctt gtc atc ttc<br>Arg Gly Thr Ala Leu Lys Gly Gly Cys Asp Ser Glu Leu Val Ile Phe<br>65 70 75 80 | | 240 |
| ctc gac tgc ttc aag agc tat gtg gac cag agg gcc cgc cgt gca gag<br>Leu Asp Cys Phe Lys Ser Tyr Val Asp Gln Arg Ala Arg Arg Ala Glu<br>85 90 95 | | 288 |
| atc ctc agt gag atg cgg gca tcg ctg gaa tcc tgg tgg cag aac cca<br>Ile Leu Ser Glu Met Arg Ala Ser Leu Glu Ser Trp Trp Gln Asn Pro<br>100 105 110 | | 336 |
| gtc cct ggt ctg aga ctc acg ttt cct gag cag agc gtg cct ggg gcc<br>Val Pro Gly Leu Arg Leu Thr Phe Pro Glu Gln Ser Val Pro Gly Ala<br>115 120 125 | | 384 |
| ctg cag ttc cgc ctg aca tcc gta gat ctt gag gac tgg atg gat gtt<br>Leu Gln Phe Arg Leu Thr Ser Val Asp Leu Glu Asp Trp Met Asp Val<br>130 135 140 | | 432 |
| agc ctg gtg cct gcc ttc aat gtc ctg ggt cag gcc ggc tcc gcg gtc<br>Ser Leu Val Pro Ala Phe Asn Val Leu Gly Gln Ala Gly Ser Ala Val<br>145 150 155 160 | | 480 |
| aaa ccc aag cca caa gtc tac tct acc ctc ctc aac agt ggc tgc caa<br>Lys Pro Lys Pro Gln Val Tyr Ser Thr Leu Leu Asn Ser Gly Cys Gln<br>165 170 175 | | 528 |
| ggg ggc gag cat gcg gcc tgc ttc aca gag ctg cgg agg aac ttt gtg<br>Gly Gly Glu His Ala Ala Cys Phe Thr Glu Leu Arg Arg Asn Phe Val<br>180 185 190 | | 576 |
| aac att cgc cca gcc aag ttg aag aac cta atc ttg ctg gtg aag cac<br>Asn Ile Arg Pro Ala Lys Leu Lys Asn Leu Ile Leu Leu Val Lys His<br>195 200 205 | | 624 |
| tgg tac cac cag gtg tgc cta cag ggg ttg tgg aag gag acg ctg ccc<br>Trp Tyr His Gln Val Cys Leu Gln Gly Leu Trp Lys Glu Thr Leu Pro<br>210 215 220 | | 672 |
| ccg gtc tat gcc ctg gaa ttg ctg acc atc ttc gcc tgg gag cag ggc<br>Pro Val Tyr Ala Leu Glu Leu Leu Thr Ile Phe Ala Trp Glu Gln Gly<br>225 230 235 240 | | 720 |
| tgt aag aag gat gct ttc agc cta ggc gaa ggc ctc cga act gtc ctg<br>Cys Lys Lys Asp Ala Phe Ser Leu Gly Glu Gly Leu Arg Thr Val Leu<br>245 250 255 | | 768 |
| ggc ctg atc caa cag cat cag cac ctg tgt gtt ttc tgg act gtc aac<br>Gly Leu Ile Gln Gln His Gln His Leu Cys Val Phe Trp Thr Val Asn<br>260 265 270 | | 816 |
| tat ggc ttc gag gac cct gca gtt ggg cag ttc ttg cag cgg cac gtt<br>Tyr Gly Phe Glu Asp Pro Ala Val Gly Gln Phe Leu Gln Arg His Val<br>275 280 285 | | 864 |
| aag aga ccc agg cct gtg atc ctg gac cca gct gac ccc aca tgg gac<br>Lys Arg Pro Arg Pro Val Ile Leu Asp Pro Ala Asp Pro Thr Trp Asp<br>290 295 300 | | 912 |
| ctg ggg aat ggg gca gcc tgg cac tgg gat ttg cat gcc cag gag gca<br>Leu Gly Asn Gly Ala Ala Trp His Trp Asp Leu His Ala Gln Glu Ala<br>305 310 315 320 | | 960 |
| gca tcc tgc tat gac cac cca tgc ttt ctg agg ggg atg ggg gac cca<br>Ala Ser Cys Tyr Asp His Pro Cys Phe Leu Arg Gly Met Gly Asp Pro<br>325 330 335 | | 1008 |

```
gtg cag tct tgg aag ggg ccg ggc ctt cca cgt gct gga tgc tca ggt      1056
Val Gln Ser Trp Lys Gly Pro Gly Leu Pro Arg Ala Gly Cys Ser Gly
            340                 345                 350 ttg ggc cac ccc atc cag cta gac cct aac cag aag acc cct gaa aac      1104
Leu Gly His Pro Ile Gln Leu Asp Pro Asn Gln Lys Thr Pro Glu Asn
            355                 360                 365 agc aag agc ctc aat gct gtg tac cca aga gca ggg agc aaa cct ccc      1152
Ser Lys Ser Leu Asn Ala Val Tyr Pro Arg Ala Gly Ser Lys Pro Pro
            370                 375                 380 tca tgc cca gct cct ggc ccc act gcg gag cca gca tcg tac ccc tct      1200
Ser Cys Pro Ala Pro Gly Pro Thr Ala Glu Pro Ala Ser Tyr Pro Ser
385                 390                 395                 400 gtg ccg gga atg gcc ttg gac ctg tct cag atc ccc acc aag gag ctg      1248
Val Pro Gly Met Ala Leu Asp Leu Ser Gln Ile Pro Thr Lys Glu Leu
                405                 410                 415 gac cgc ttc atc cag gac cac ctg aag ccg agc ccc cag ttc cag gag      1296
Asp Arg Phe Ile Gln Asp His Leu Lys Pro Ser Pro Gln Phe Gln Glu
                420                 425                 430 cag gtg aaa aag gcc atc gac atc atc ttg cgc tgc ctc cat gag aac      1344
Gln Val Lys Lys Ala Ile Asp Ile Ile Leu Arg Cys Leu His Glu Asn
            435                 440                 445 tgt gtt cac aag gcc tca aga gtc agt aaa ggg ggc tca ttt ggc cgg      1392
Cys Val His Lys Ala Ser Arg Val Ser Lys Gly Gly Ser Phe Gly Arg
450                 455                 460 ggc aca gac cta agg gat ggc tgt gat gtt gaa ctc atc atc ttc ctc      1440
Gly Thr Asp Leu Arg Asp Gly Cys Asp Val Glu Leu Ile Ile Phe Leu
465                 470                 475                 480 aac tgc ttc acg gac tac aag gac cag ggg ccc cgc cgc gca gag atc      1488
Asn Cys Phe Thr Asp Tyr Lys Asp Gln Gly Pro Arg Arg Ala Glu Ile
                485                 490                 495 ctt gat gag atg cga gcg cac gta gaa tcc tgg tgg cag gac cag gtg      1536
Leu Asp Glu Met Arg Ala His Val Glu Ser Trp Trp Gln Asp Gln Val
                500                 505                 510 ccc agc ctg agc ctt cag ttt cct gag cag aat gtg cct gag gct ctg      1584
Pro Ser Leu Ser Leu Gln Phe Pro Glu Gln Asn Val Pro Glu Ala Leu
            515                 520                 525 cag ttc cag ctg gtg tcc aca gcc ctg aag agc tgg acg gat gtt agc      1632
Gln Phe Gln Leu Val Ser Thr Ala Leu Lys Ser Trp Thr Asp Val Ser
530                 535                 540 ctg ctg cct gcc ttc gat gct gtg ggg cag ctc agt tct ggc acc aaa      1680
Leu Leu Pro Ala Phe Asp Ala Val Gly Gln Leu Ser Ser Gly Thr Lys
545                 550                 555                 560 cca aat ccc cag gtc tac tcg agg ctc ctc acc agt ggc tgc cag gag      1728
Pro Asn Pro Gln Val Tyr Ser Arg Leu Leu Thr Ser Gly Cys Gln Glu
                565                 570                 575 ggc gag cat aag gcc tgc ttc gca gag ctg cgg agg aac ttc atg aac      1776
Gly Glu His Lys Ala Cys Phe Ala Glu Leu Arg Arg Asn Phe Met Asn
            580                 585                 590 att cgc cct gtc aag ctg aag aac ctg att ctg ctg gtg aag cac tgg      1824
Ile Arg Pro Val Lys Leu Lys Asn Leu Ile Leu Leu Val Lys His Trp
            595                 600                 605 tac cgc cag gtt gcg gct cag aac aaa gga aaa gga cca gcc cct gcc      1872
Tyr Arg Gln Val Ala Ala Gln Asn Lys Gly Lys Gly Pro Ala Pro Ala
            610                 615                 620 tct ctg ccc cca gcc tat gcc ctg gag ctc ctc acc atc ttt gcc tgg      1920
Ser Leu Pro Pro Ala Tyr Ala Leu Glu Leu Leu Thr Ile Phe Ala Trp
625                 630                 635                 640 gag cag ggc tgc agg cag gat tgt ttc aac atg gcc caa ggc ttc cgg      1968
Glu Gln Gly Cys Arg Gln Asp Cys Phe Asn Met Ala Gln Gly Phe Arg
```

-continued

```
                    645                 650                 655
acg gtg ctg ggg ctc gtg caa cag cat cag cag ctc tgt gtc tac tgg      2016
Thr Val Leu Gly Leu Val Gln Gln His Gln Gln Leu Cys Val Tyr Trp
            660                 665                 670 acg gtc aac tat agc act gag gac cca gcc atg aga atg cac ctt ctt      2064
Thr Val Asn Tyr Ser Thr Glu Asp Pro Ala Met Arg Met His Leu Leu
        675                 680                 685 ggc cag ctt cga aaa ccc aga ccc ctg gtc ctg gac ccc gct gat ccc      2112
Gly Gln Leu Arg Lys Pro Arg Pro Leu Val Leu Asp Pro Ala Asp Pro
690                 695                 700 acc tgg aac gtg ggc cac ggt agc tgg gag ctg ttg gcc cag gaa gca      2160
Thr Trp Asn Val Gly His Gly Ser Trp Glu Leu Leu Ala Gln Glu Ala
705                 710                 715                 720 gca gcg ctg ggg atg cag gcc tgc ttt ctg agt aga gac ggg aca tct      2208
Ala Ala Leu Gly Met Gln Ala Cys Phe Leu Ser Arg Asp Gly Thr Ser
                725                 730                 735 gtg cag ccc tgg gat gtg atg cca gcc ctc ctt tac caa acc cca gct      2256
Val Gln Pro Trp Asp Val Met Pro Ala Leu Leu Tyr Gln Thr Pro Ala
            740                 745                 750 ggg gac ctt gac aag ttc atc agt gaa ttt ctc cag ccc aac cgc cag      2304
Gly Asp Leu Asp Lys Phe Ile Ser Glu Phe Leu Gln Pro Asn Arg Gln
        755                 760                 765 ttc ctg gcc cag gtg aac aag gcc gtt gat acc atc tgt tca ttt ttg      2352
Phe Leu Ala Gln Val Asn Lys Ala Val Asp Thr Ile Cys Ser Phe Leu
770                 775                 780 aag gaa aac tgc ttc cgg aat tct ccc atc aaa gtg atc aag gtg gtc      2400
Lys Glu Asn Cys Phe Arg Asn Ser Pro Ile Lys Val Ile Lys Val Val
785                 790                 795                 800 aag ggt ggc tct tca gcc aaa ggc aca gct ctg cga ggc cgc tca gat      2448
Lys Gly Gly Ser Ser Ala Lys Gly Thr Ala Leu Arg Gly Arg Ser Asp
                805                 810                 815 gcc gac ctc gtg gtg ttc ctc agc tgc ttc agc cag ttc act gag cag      2496
Ala Asp Leu Val Val Phe Leu Ser Cys Phe Ser Gln Phe Thr Glu Gln
            820                 825                 830 ggc aac aag cgg gcc gag atc atc tcc gag atc cga gcc cag ctg gag      2544
Gly Asn Lys Arg Ala Glu Ile Ile Ser Glu Ile Arg Ala Gln Leu Glu
        835                 840                 845 gca tgt caa cag gag cgg cag ttc gag gtc aag ttt gaa gtc tcc aaa      2592
Ala Cys Gln Gln Glu Arg Gln Phe Glu Val Lys Phe Glu Val Ser Lys
850                 855                 860 tgg gag aat ccc cgc gtg ctg agc ttc tca ctg aca tcc cag acg atg      2640
Trp Glu Asn Pro Arg Val Leu Ser Phe Ser Leu Thr Ser Gln Thr Met
865                 870                 875                 880 ctg gac cag agt gtg gac ttt gat gtg ctg cca gcc ttt gac gcc cta      2688
Leu Asp Gln Ser Val Asp Phe Asp Val Leu Pro Ala Phe Asp Ala Leu
                885                 890                 895 ggc cag ctg gtc tct ggc tcc agg ccc agc tct caa gtc tac gtc gac      2736
Gly Gln Leu Val Ser Gly Ser Arg Pro Ser Ser Gln Val Tyr Val Asp
            900                 905                 910 ctc atc cac agc tac agc aat gcg ggc gag tac tcc acc tgc ttc aca      2784
Leu Ile His Ser Tyr Ser Asn Ala Gly Glu Tyr Ser Thr Cys Phe Thr
        915                 920                 925 gag cta caa cgg gac ttc atc atc tct cgc cct acc aag ctg aag agc      2832
Glu Leu Gln Arg Asp Phe Ile Ile Ser Arg Pro Thr Lys Leu Lys Ser
930                 935                 940 ctg atc cgg ctg gtg aag cac tgg tac cag cag tgt acc aag atc tcc      2880
Leu Ile Arg Leu Val Lys His Trp Tyr Gln Gln Cys Thr Lys Ile Ser
945                 950                 955                 960 aag ggg aga ggc tcc cta ccc cca cag cac ggg ctg gaa ctc ctg act      2928
```

```
                                     Lys Gly Arg Gly Ser Leu Pro Pro Gln His Gly Leu Glu Leu Leu Thr
                                                     965                 970                 975 gtg tat gcc tgg gag cag ggc ggg aag gac tcc cag ttc aac atg gct                                 2976
Val Tyr Ala Trp Glu Gln Gly Gly Lys Asp Ser Gln Phe Asn Met Ala
            980                 985                 990 ggc ttc cgc acg gtc ctg gag ctg gtc acc cag tac cgc cag ctc                                     3024
Glu Gly Phe Arg Thr Val Leu Glu Leu Val Thr Gln Tyr Arg Gln Leu
        995                 1000                1005 tgt atc tac tgg acc atc aac tac aac gcc aag gac aag act gtt                                     3069
Cys Ile Tyr Trp Thr Ile Asn Tyr Asn Ala Lys Asp Lys Thr Val
    1010                1015                1020 gga gac ttc ctg aaa cag cag ctt cag aag ccc agg cct atc atc                                     3114
Gly Asp Phe Leu Lys Gln Gln Leu Gln Lys Pro Arg Pro Ile Ile
    1025                1030                1035 ctg gat ccg gct gac ccg aca ggc aac ctg ggc cac aat gcc cgc                                     3159
Leu Asp Pro Ala Asp Pro Thr Gly Asn Leu Gly His Asn Ala Arg
    1040                1045                1050 tgg gac ctg ctg gcc aag gaa gct gca gcc tgc aca tct gcc ctg                                     3204
Trp Asp Leu Leu Ala Lys Glu Ala Ala Ala Cys Thr Ser Ala Leu
    1055                1060                1065 tgc tgc atg gga cgg aat ggc atc ccc atc cag cca tgg cca gtg                                     3249
Cys Cys Met Gly Arg Asn Gly Ile Pro Ile Gln Pro Trp Pro Val
    1070                1075                1080 aag gct gct gtg tga                                                                             3264
Lys Ala Ala Val
    1085

<210> SEQ ID NO 10
<211> LENGTH: 1087
<212> TYPE: PRT
<213> ORGANISM: Homo sapiens

<400> SEQUENCE: 10

Met Asp Leu Tyr Ser Thr Pro Ala Ala Ala Leu Asp Arg Phe Val Ala
1               5                   10                  15

Arg Arg Leu Gln Pro Arg Lys Glu Phe Val Glu Lys Ala Arg Arg Ala
            20                  25                  30

Leu Gly Ala Leu Ala Ala Leu Arg Glu Arg Gly Gly Arg Leu Gly
        35                  40                  45

Ala Ala Ala Pro Arg Val Leu Lys Thr Val Lys Gly Gly Ser Ser Gly
    50                  55                  60

Arg Gly Thr Ala Leu Lys Gly Gly Cys Asp Ser Glu Leu Val Ile Phe
65                  70                  75                  80

Leu Asp Cys Phe Lys Ser Tyr Val Asp Gln Arg Ala Arg Arg Ala Glu
                85                  90                  95

Ile Leu Ser Glu Met Arg Ala Ser Leu Glu Ser Trp Trp Gln Asn Pro
            100                 105                 110

Val Pro Gly Leu Arg Leu Thr Phe Pro Glu Gln Ser Val Pro Gly Ala
        115                 120                 125

Leu Gln Phe Arg Leu Thr Ser Val Asp Leu Glu Asp Trp Met Asp Val
    130                 135                 140

Ser Leu Val Pro Ala Phe Asn Val Leu Gly Gln Ala Gly Ser Ala Val
145                 150                 155                 160

Lys Pro Lys Pro Gln Val Tyr Ser Thr Leu Leu Asn Ser Gly Cys Gln
                165                 170                 175

Gly Gly Glu His Ala Ala Cys Phe Thr Glu Leu Arg Arg Asn Phe Val
            180                 185                 190
```

-continued

```
Asn Ile Arg Pro Ala Lys Leu Lys Asn Leu Ile Leu Leu Val Lys His
        195                 200                 205
Trp Tyr His Gln Val Cys Leu Gln Gly Leu Trp Lys Glu Thr Leu Pro
210                 215                 220
Pro Val Tyr Ala Leu Glu Leu Leu Thr Ile Phe Ala Trp Glu Gln Gly
225                 230                 235                 240
Cys Lys Lys Asp Ala Phe Ser Leu Gly Glu Gly Leu Arg Thr Val Leu
                245                 250                 255
Gly Leu Ile Gln Gln His Gln His Leu Cys Val Phe Trp Thr Val Asn
            260                 265                 270
Tyr Gly Phe Glu Asp Pro Ala Val Gly Gln Phe Leu Gln Arg His Val
        275                 280                 285
Lys Arg Pro Arg Pro Val Ile Leu Asp Pro Ala Asp Pro Thr Trp Asp
290                 295                 300
Leu Gly Asn Gly Ala Ala Trp His Trp Asp Leu His Ala Gln Glu Ala
305                 310                 315                 320
Ala Ser Cys Tyr Asp His Pro Cys Phe Leu Arg Gly Met Gly Asp Pro
                325                 330                 335
Val Gln Ser Trp Lys Gly Pro Gly Leu Pro Arg Ala Gly Cys Ser Gly
            340                 345                 350
Leu Gly His Pro Ile Gln Leu Asp Pro Asn Gln Lys Thr Pro Glu Asn
        355                 360                 365
Ser Lys Ser Leu Asn Ala Val Tyr Pro Arg Ala Gly Ser Lys Pro Pro
370                 375                 380
Ser Cys Pro Ala Pro Gly Pro Thr Ala Glu Pro Ala Ser Tyr Pro Ser
385                 390                 395                 400
Val Pro Gly Met Ala Leu Asp Leu Ser Gln Ile Pro Thr Lys Glu Leu
                405                 410                 415
Asp Arg Phe Ile Gln Asp His Leu Lys Pro Ser Pro Gln Phe Gln Glu
            420                 425                 430
Gln Val Lys Lys Ala Ile Asp Ile Ile Leu Arg Cys Leu His Glu Asn
        435                 440                 445
Cys Val His Lys Ala Ser Arg Val Ser Lys Gly Gly Ser Phe Gly Arg
450                 455                 460
Gly Thr Asp Leu Arg Asp Gly Cys Asp Val Glu Leu Ile Ile Phe Leu
465                 470                 475                 480
Asn Cys Phe Thr Asp Tyr Lys Asp Gln Gly Pro Arg Arg Ala Glu Ile
                485                 490                 495
Leu Asp Glu Met Arg Ala His Val Glu Ser Trp Trp Gln Asp Gln Val
            500                 505                 510
Pro Ser Leu Ser Leu Gln Phe Pro Glu Gln Asn Val Pro Glu Ala Leu
        515                 520                 525
Gln Phe Gln Leu Val Ser Thr Ala Leu Lys Ser Trp Thr Asp Val Ser
530                 535                 540
Leu Leu Pro Ala Phe Asp Ala Val Gly Gln Leu Ser Ser Gly Thr Lys
545                 550                 555                 560
Pro Asn Pro Gln Val Tyr Ser Arg Leu Leu Thr Ser Gly Cys Gln Glu
                565                 570                 575
Gly Glu His Lys Ala Cys Phe Ala Glu Leu Arg Arg Asn Phe Met Asn
            580                 585                 590
Ile Arg Pro Val Lys Leu Lys Asn Leu Ile Leu Leu Val Lys His Trp
        595                 600                 605
Tyr Arg Gln Val Ala Ala Gln Asn Lys Gly Lys Gly Pro Ala Pro Ala
```

```
            610                 615                 620
Ser Leu Pro Pro Ala Tyr Ala Leu Glu Leu Leu Thr Ile Phe Ala Trp
625                 630                 635                 640

Glu Gln Gly Cys Arg Gln Asp Cys Phe Asn Met Ala Gln Gly Phe Arg
                645                 650                 655

Thr Val Leu Gly Leu Val Gln His Gln Gln Leu Cys Val Tyr Trp
                660                 665                 670

Thr Val Asn Tyr Ser Thr Glu Asp Pro Ala Met Arg Met His Leu Leu
                675                 680                 685

Gly Gln Leu Arg Lys Pro Arg Pro Leu Val Leu Asp Pro Ala Asp Pro
690                 695                 700

Thr Trp Asn Val Gly His Gly Ser Trp Glu Leu Leu Ala Gln Glu Ala
705                 710                 715                 720

Ala Ala Leu Gly Met Gln Ala Cys Phe Leu Ser Arg Asp Gly Thr Ser
                725                 730                 735

Val Gln Pro Trp Asp Val Met Pro Ala Leu Leu Tyr Gln Thr Pro Ala
                740                 745                 750

Gly Asp Leu Asp Lys Phe Ile Ser Glu Phe Leu Gln Pro Asn Arg Gln
                755                 760                 765

Phe Leu Ala Gln Val Asn Lys Ala Val Asp Thr Ile Cys Ser Phe Leu
770                 775                 780

Lys Glu Asn Cys Phe Arg Asn Ser Pro Ile Lys Val Ile Lys Val Val
785                 790                 795                 800

Lys Gly Gly Ser Ser Ala Lys Gly Thr Ala Leu Arg Gly Arg Ser Asp
                805                 810                 815

Ala Asp Leu Val Val Phe Leu Ser Cys Phe Ser Gln Phe Thr Glu Gln
                820                 825                 830

Gly Asn Lys Arg Ala Glu Ile Ile Ser Glu Ile Arg Ala Gln Leu Glu
                835                 840                 845

Ala Cys Gln Gln Glu Arg Gln Phe Glu Val Lys Phe Glu Val Ser Lys
850                 855                 860

Trp Glu Asn Pro Arg Val Leu Ser Phe Ser Leu Thr Ser Gln Thr Met
865                 870                 875                 880

Leu Asp Gln Ser Val Asp Phe Asp Val Leu Pro Ala Phe Asp Ala Leu
                885                 890                 895

Gly Gln Leu Val Ser Gly Ser Arg Pro Ser Ser Gln Val Tyr Val Asp
                900                 905                 910

Leu Ile His Ser Tyr Ser Asn Ala Gly Glu Tyr Ser Thr Cys Phe Thr
                915                 920                 925

Glu Leu Gln Arg Asp Phe Ile Ile Ser Arg Pro Thr Lys Leu Lys Ser
930                 935                 940

Leu Ile Arg Leu Val Lys His Trp Tyr Gln Gln Cys Thr Lys Ile Ser
945                 950                 955                 960

Lys Gly Arg Gly Ser Leu Pro Pro Gln His Gly Leu Glu Leu Leu Thr
                965                 970                 975

Val Tyr Ala Trp Glu Gln Gly Gly Lys Asp Ser Gln Phe Asn Met Ala
                980                 985                 990

Glu Gly Phe Arg Thr Val Leu Glu Leu Val Thr Gln Tyr Arg Gln Leu
                995                 1000                1005

Cys Ile Tyr Trp Thr Ile Asn Tyr Asn Ala Lys Asp Lys Thr Val
    1010                1015                1020

Gly Asp Phe Leu Lys Gln Gln Leu Gln Lys Pro Arg Pro Ile Ile
    1025                1030                1035
```

Leu Asp Pro Ala Asp Pro Thr Gly Asn Leu Gly His Asn Ala Arg
1040                1045                1050

Trp Asp Leu Leu Ala Lys Glu Ala Ala Ala Cys Thr Ser Ala Leu
1055                1060                1065

Cys Cys Met Gly Arg Asn Gly Ile Pro Ile Gln Pro Trp Pro Val
1070                1075                1080

Lys Ala Ala Val
    1085

<210> SEQ ID NO 11
<211> LENGTH: 1104
<212> TYPE: DNA
<213> ORGANISM: Mus musculus
<220> FEATURE:
<221> NAME/KEY: CDS
<222> LOCATION: (1)..(1104)
<223> OTHER INFORMATION:
<300> PUBLICATION INFORMATION:
<301> AUTHORS: Coccia, E.M., et al.
<302> TITLE: A full-length murine 2-5A synthetase cDNA transfected in
      NIH-3T3 cells
<303> JOURNAL: Virology
<304> VOLUME: 179
<305> ISSUE: 1
<306> PAGES: 228-233
<307> DATE: 1990
<308> DATABASE ACCESSION NUMBER: NCBI/M33863
<309> DATABASE ENTRY DATE: 1993-06-11

<400> SEQUENCE: 11 atg gag cac gga ctc agg agc atc cca gcc tgg acg ctg gac aag ttc     48
Met Glu His Gly Leu Arg Ser Ile Pro Ala Trp Thr Leu Asp Lys Phe
1               5                   10                  15 ata gag gat tac ctc ctt ccc gac acc acc ttt ggt gct gat gtc aaa     96
Ile Glu Asp Tyr Leu Leu Pro Asp Thr Thr Phe Gly Ala Asp Val Lys
                20                  25                  30 tca gcc gtc aat gtc gtg tgt gat ttc ctg aag gag aga tgc ttc caa    144
Ser Ala Val Asn Val Val Cys Asp Phe Leu Lys Glu Arg Cys Phe Gln
            35                  40                  45 ggt gct gcc cac cca gtg agg gtc tcc aag gtg gtg aag ggt ggc tcc    192
Gly Ala Ala His Pro Val Arg Val Ser Lys Val Val Lys Gly Gly Ser
        50                  55                  60 tca ggc aaa ggc acc aca ctc aag ggc agg tca gac gct gac ctg gtg    240
Ser Gly Lys Gly Thr Thr Leu Lys Gly Arg Ser Asp Ala Asp Leu Val
65                  70                  75                  80 gtg ttc ctt aac aat ctc acc agc ttt gag gat cag tta aac cga cgg    288
Val Phe Leu Asn Asn Leu Thr Ser Phe Glu Asp Gln Leu Asn Arg Arg
                85                  90                  95 gga gag ttc atc aag gaa att aag aaa cag ctg tac gag gtt cag cat    336
Gly Glu Phe Ile Lys Glu Ile Lys Lys Gln Leu Tyr Glu Val Gln His
                100                 105                 110 gag aga cgt ttt aga gtc aag ttt gag gtc cag agt tca tgg tgg ccc    384
Glu Arg Arg Phe Arg Val Lys Phe Glu Val Gln Ser Ser Trp Trp Pro
            115                 120                 125 aac gcc cgg tct ctg agc ttc aag ctg agc gcc ccc cat ctg cat cag    432
Asn Ala Arg Ser Leu Ser Phe Lys Leu Ser Ala Pro His Leu His Gln
        130                 135                 140 gag gtg gag ttt gat gtg ctg cca gcc ttt gat gtc ctg ggt cat gtt    480
Glu Val Glu Phe Asp Val Leu Pro Ala Phe Asp Val Leu Gly His Val
145                 150                 155                 160 aat act tcc agc aag cct gat ccc aga atc tat gcc atc ctc atc gag    528
Asn Thr Ser Ser Lys Pro Asp Pro Arg Ile Tyr Ala Ile Leu Ile Glu
                165                 170                 175

| | | | | | | | | | | | | | | | | |
|---|---|---|---|---|---|---|---|---|---|---|---|---|---|---|---|---|
| gaa | tgt | acc | tcc | ctg | ggg | aag | gat | ggc | gag | ttc | tct | acc | tgc | ttc | acg | 576 |
| Glu | Cys | Thr | Ser | Leu | Gly | Lys | Asp | Gly | Glu | Phe | Ser | Thr | Cys | Phe | Thr | |
| | | | 180 | | | | | 185 | | | | | 190 | | | |
| gag | ctc | cag | cgg | aac | ttc | ctg | aag | cag | cgc | cca | acc | aag | ctg | aag | agt | 624 |
| Glu | Leu | Gln | Arg | Asn | Phe | Leu | Lys | Gln | Arg | Pro | Thr | Lys | Leu | Lys | Ser | |
| | | | 195 | | | | | 200 | | | | | 205 | | | |
| ctc | atc | cgc | ctg | gtc | aag | cac | tgg | tac | caa | ctg | tgt | aag | gag | aag | ctg | 672 |
| Leu | Ile | Arg | Leu | Val | Lys | His | Trp | Tyr | Gln | Leu | Cys | Lys | Glu | Lys | Leu | |
| | 210 | | | | | 215 | | | | | 220 | | | | | |
| ggg | aag | cca | ttg | cct | cca | cag | tac | gcc | cta | gag | ttg | ctc | act | gtc | ttt | 720 |
| Gly | Lys | Pro | Leu | Pro | Pro | Gln | Tyr | Ala | Leu | Glu | Leu | Leu | Thr | Val | Phe | |
| 225 | | | | | 230 | | | | | 235 | | | | | 240 | |
| gcc | tgg | gaa | caa | ggg | aat | gga | tgt | tat | gag | ttc | aac | aca | gcc | cag | ggc | 768 |
| Ala | Trp | Glu | Gln | Gly | Asn | Gly | Cys | Tyr | Glu | Phe | Asn | Thr | Ala | Gln | Gly | |
| | | | | 245 | | | | | 250 | | | | | 255 | | |
| ttc | cgg | acc | gtc | ttg | gaa | ctg | gtc | atc | aat | tat | cag | cat | ctt | cga | atc | 816 |
| Phe | Arg | Thr | Val | Leu | Glu | Leu | Val | Ile | Asn | Tyr | Gln | His | Leu | Arg | Ile | |
| | | | 260 | | | | | 265 | | | | | 270 | | | |
| tac | tgg | aca | aag | tat | tat | gac | ttt | caa | cac | cag | gag | gtc | tcc | aaa | tac | 864 |
| Tyr | Trp | Thr | Lys | Tyr | Tyr | Asp | Phe | Gln | His | Gln | Glu | Val | Ser | Lys | Tyr | |
| | | | 275 | | | | | 280 | | | | | 285 | | | |
| ctg | cac | aga | cag | ctc | aga | aaa | gcc | agg | cct | gtg | atc | ctg | gac | cca | gct | 912 |
| Leu | His | Arg | Gln | Leu | Arg | Lys | Ala | Arg | Pro | Val | Ile | Leu | Asp | Pro | Ala | |
| | 290 | | | | | 295 | | | | | 300 | | | | | |
| gac | cca | aca | ggg | aat | gtg | gcc | ggt | ggg | aac | cca | gag | ggc | tgg | agg | cgg | 960 |
| Asp | Pro | Thr | Gly | Asn | Val | Ala | Gly | Gly | Asn | Pro | Glu | Gly | Trp | Arg | Arg | |
| 305 | | | | | 310 | | | | | 315 | | | | | 320 | |
| ttg | gct | gaa | gag | gct | gat | gtg | tgg | cta | tgg | tac | cca | tgt | ttt | att | aaa | 1008 |
| Leu | Ala | Glu | Glu | Ala | Asp | Val | Trp | Leu | Trp | Tyr | Pro | Cys | Phe | Ile | Lys | |
| | | | | 325 | | | | | 330 | | | | | 335 | | |
| aag | gat | ggt | tcc | cga | gtg | agc | tcc | tgg | gat | gtg | ccg | acg | gtg | gtt | cct | 1056 |
| Lys | Asp | Gly | Ser | Arg | Val | Ser | Ser | Trp | Asp | Val | Pro | Thr | Val | Val | Pro | |
| | | | 340 | | | | | 345 | | | | | 350 | | | |
| gta | cct | ttt | gag | cag | gta | gaa | gag | aac | tgg | aca | tgt | atc | ctg | ctg | tga | 1104 |
| Val | Pro | Phe | Glu | Gln | Val | Glu | Glu | Asn | Trp | Thr | Cys | Ile | Leu | Leu | | |
| | | | 355 | | | | | 360 | | | | | 365 | | | |

<210> SEQ ID NO 12
<211> LENGTH: 367
<212> TYPE: PRT
<213> ORGANISM: Mus musculus

<400> SEQUENCE: 12

Met Glu His Gly Leu Arg Ser Ile Pro Ala Trp Thr Leu Asp Lys Phe
1               5                   10                  15

Ile Glu Asp Tyr Leu Leu Pro Asp Thr Thr Phe Gly Ala Asp Val Lys
                20                  25                  30

Ser Ala Val Asn Val Val Cys Asp Phe Leu Lys Glu Arg Cys Phe Gln
            35                  40                  45

Gly Ala Ala His Pro Val Arg Val Ser Lys Val Lys Gly Gly Ser
        50                  55                  60

Ser Gly Lys Gly Thr Thr Leu Lys Gly Arg Ser Asp Ala Asp Leu Val
65                  70                  75                  80

Val Phe Leu Asn Asn Leu Thr Ser Phe Glu Asp Gln Leu Asn Arg Arg
                85                  90                  95

Gly Glu Phe Ile Lys Glu Ile Lys Lys Gln Leu Tyr Glu Val Gln His
                100                 105                 110

Glu Arg Arg Phe Arg Val Lys Phe Glu Val Gln Ser Ser Trp Trp Pro

```
                    115                 120                 125
Asn Ala Arg Ser Leu Ser Phe Lys Leu Ser Ala Pro His Leu His Gln
    130                 135                 140

Glu Val Glu Phe Asp Val Leu Pro Ala Phe Asp Val Leu Gly His Val
145                 150                 155                 160

Asn Thr Ser Ser Lys Pro Asp Pro Arg Ile Tyr Ala Ile Leu Ile Glu
                165                 170                 175

Glu Cys Thr Ser Leu Gly Lys Asp Gly Glu Phe Ser Thr Cys Phe Thr
            180                 185                 190

Glu Leu Gln Arg Asn Phe Leu Lys Gln Arg Pro Thr Lys Leu Lys Ser
                195                 200                 205

Leu Ile Arg Leu Val Lys His Trp Tyr Gln Leu Cys Lys Glu Lys Leu
    210                 215                 220

Gly Lys Pro Leu Pro Pro Gln Tyr Ala Leu Glu Leu Leu Thr Val Phe
225                 230                 235                 240

Ala Trp Glu Gln Gly Asn Gly Cys Tyr Glu Phe Asn Thr Ala Gln Gly
                245                 250                 255

Phe Arg Thr Val Leu Glu Leu Val Ile Asn Tyr Gln His Leu Arg Ile
            260                 265                 270

Tyr Trp Thr Lys Tyr Tyr Asp Phe Gln His Gln Glu Val Ser Lys Tyr
                275                 280                 285

Leu His Arg Gln Leu Arg Lys Ala Arg Pro Val Ile Leu Asp Pro Ala
    290                 295                 300

Asp Pro Thr Gly Asn Val Ala Gly Gly Asn Pro Glu Gly Trp Arg Arg
305                 310                 315                 320

Leu Ala Glu Glu Ala Asp Val Trp Leu Trp Tyr Pro Cys Phe Ile Lys
                325                 330                 335

Lys Asp Gly Ser Arg Val Ser Ser Trp Asp Val Pro Thr Val Val Pro
            340                 345                 350

Val Pro Phe Glu Gln Val Glu Glu Asn Trp Thr Cys Ile Leu Leu
                355                 360                 365

<210> SEQ ID NO 13
<211> LENGTH: 1590
<212> TYPE: DNA
<213> ORGANISM: Homo sapiens
<300> PUBLICATION INFORMATION:
<301> AUTHORS: Aissouni, Y. et al.
<302> TITLE: The cleavage/polyadenylation activity triggered by a U-rich
      motif sequence
<303> JOURNAL: J. Biol. Chem.
<304> VOLUME: 277
<305> ISSUE: 39
<306> PAGES: 35808-35814
<307> DATE: 2002
<308> DATABASE ACCESSION NUMBER: NCBI/NM_016816
<309> DATABASE ENTRY DATE: 2003-04-06
<300> PUBLICATION INFORMATION:
<301> AUTHORS: Behera, A.K., et al.
<302> TITLE: 2'-5' Oligoadenylate synthetase plays a critical role in
      interferon-gamma inhibition
<303> JOURNAL: J. Biol. Chem.
<304> VOLUME: 277
<305> ISSUE: 28
<306> PAGES: 25601-25608
<307> DATE: 2002
<308> DATABASE ACCESSION NUMBER: NCBI/NM_016816
<309> DATABASE ENTRY DATE: 2003-04-06
<300> PUBLICATION INFORMATION:
<301> AUTHORS: Sarkar, S.N., et al.
<302> TITLE: Identification of the substrate-binding sites of
      2'-5'-oligoadenylate synthetase
<303> JOURNAL: J. Biol. Chem.
```

-continued

```
<304> VOLUME: 277
<305> ISSUE: 27
<306> PAGES: 24321-24330
<307> DATE: 2002
<308> DATABASE ACCESSION NUMBER: NCBI/NM_016816
<309> DATABASE ENTRY DATE: 2003-04-06
<300> PUBLICATION INFORMATION:
<301> AUTHORS: Hovnanian, A., et al.
<302> TITLE: The human 2',5'-oligoadenylate synthetase locus is composed
       of three distinct genes
<303> JOURNAL: Genomics
<304> VOLUME: 52
<305> ISSUE: 3
<306> PAGES: 267-277
<307> DATE: 1998
<308> DATABASE ACCESSION NUMBER: NCBI/NM_016816
<309> DATABASE ENTRY DATE: 2003-04-06
<300> PUBLICATION INFORMATION:
<301> AUTHORS: Renault, B.
<302> TITLE: A sequence-ready physical map of a region of 12q24.1
<303> JOURNAL: Genomics
<304> VOLUME: 45
<305> ISSUE: 2
<306> PAGES: 271-278
<307> DATE: 1997
<308> DATABASE ACCESSION NUMBER: NCBI/NM_016816
<309> DATABASE ENTRY DATE: 2003-04-06
<300> PUBLICATION INFORMATION:
<301> AUTHORS: Nechiporuk, T., et al.
<302> TITLE: A high-resolution PAC and BAC map of the SCA2 region
<303> JOURNAL: Genomics
<304> VOLUME: 44
<305> ISSUE: 3
<306> PAGES: 321-329
<307> DATE: 1997
<308> DATABASE ACCESSION NUMBER: NCBI/NM_016816
<309> DATABASE ENTRY DATE: 2003-04-06
<300> PUBLICATION INFORMATION:
<301> AUTHORS: Wathelet, M.G., et al.
<302> TITLE: Cloning and chromosomal location of human genes inducible
       by type I interferon
<303> JOURNAL: Somat. Cell Mol. Genet.
<304> VOLUME: 14
<305> ISSUE: 5
<306> PAGES: 415-426
<307> DATE: 1988
<308> DATABASE ACCESSION NUMBER: NCBI/NM_016816
<309> DATABASE ENTRY DATE: 2003-04-06
<300> PUBLICATION INFORMATION:
<301> AUTHORS: Rutherford, M.N., et al.
<302> TITLE: Interferon-induced binding of nuclear factors to promoter
       elements of the 2-5A synthetase gene
<303> JOURNAL: EMBO J.
<304> VOLUME: 7
<305> ISSUE: 3
<306> PAGES: 751-759
<307> DATE: 1988
<308> DATABASE ACCESSION NUMBER: NCBI/NM_016816
<309> DATABASE ENTRY DATE: 2003-04-06
<300> PUBLICATION INFORMATION:
<301> AUTHORS: Wathelet, M.G., et al.
<302> TITLE: New inducers revealed by the promoter sequence analysis of
       two interferon-activated human genes
<303> JOURNAL: Eur. J. Biochem.
<304> VOLUME: 169
<305> ISSUE: 2
<306> PAGES: 313-321
<307> DATE: 1987
<308> DATABASE ACCESSION NUMBER: NCBI/NM_016816
<309> DATABASE ENTRY DATE: 2003-04-06
<300> PUBLICATION INFORMATION:
<301> AUTHORS: Benech, P., et al.
<302> TITLE: Interferon-responsive regulatory elements in the promoter
       of the human 2',5'-oligo(A) synthetase gene
<303> JOURNAL: Mol. Cell. Biol.
<304> VOLUME: 7
<305> ISSUE: 12
<306> PAGES: 4498-4504
<307> DATE: 1987
```

-continued

```
<308> DATABASE ACCESSION NUMBER: NCBI/NM_016816
<309> DATABASE ENTRY DATE: 2003-04-06
<300> PUBLICATION INFORMATION:
<301> AUTHORS: Hovanessian, A.G., et al.
<302> TITLE: Identification of 69-kd and 100-kd forms of 2-5A sythetase
<303> JOURNAL: EMBO J.
<304> VOLUME: 6
<305> ISSUE: 5
<306> PAGES: 1273-1280
<307> DATE: 1987
<308> DATABASE ACCESSION NUMBER: NCBI/NM_016816
<309> DATABASE ENTRY DATE: 2003-04-06
<300> PUBLICATION INFORMATION:
<301> AUTHORS: Williams, B.R., et al.
<302> TITLE: Interferon-regulated human 2-5A synthetase gene maps to
       chromosome
<303> JOURNAL: Somat. Cell Mol. Genet.
<304> VOLUME: 12
<305> ISSUE: 4
<306> PAGES: 403-408
<307> DATE: 1986
<308> DATABASE ACCESSION NUMBER: NCBI/NM_016816
<309> DATABASE ENTRY DATE: 2003-04-06
<300> PUBLICATION INFORMATION:
<301> AUTHORS: Shiojiri, S., et al.
<302> TITLE: Structure and expression of a cloned cDNA
<303> JOURNAL: J. Biochem.
<304> VOLUME: 99
<305> ISSUE: 5
<306> PAGES: 1455-1464
<307> DATE: 1986
<308> DATABASE ACCESSION NUMBER: NCBI/NM_016816
<309> DATABASE ENTRY DATE: 2003-04-06
<300> PUBLICATION INFORMATION:
<301> AUTHORS: Wathelet, M., et al.
<302> TITLE: Full-length sequence and expression of the 42 kDa 2-5A
       synthetase
<303> JOURNAL: FEBS Lett.
<304> VOLUME: 196
<305> ISSUE: 1
<306> PAGES: 113-120
<307> DATE: 1986
<308> DATABASE ACCESSION NUMBER: NCBI/NM_016816
<309> DATABASE ENTRY DATE: 2003-04-06
<300> PUBLICATION INFORMATION:
<301> AUTHORS: Benech, P., et al.
<302> TITLE: Structure of two forms of the interferon-induced (2'-5')
       oligo A synthetase
<303> JOURNAL: EMBO J.
<304> VOLUME: 4
<305> ISSUE: 9
<306> PAGES: 2249-2256
<307> DATE: 1985
<308> DATABASE ACCESSION NUMBER: NCBI/NM_016816
<309> DATABASE ENTRY DATE: 2003-04-06
<300> PUBLICATION INFORMATION:
<301> AUTHORS: Saunders, M.E., et al.
<302> TITLE: Human 2-5A synthetase: characterization of a novel cDNA and
       corresponding gene structure
<303> JOURNAL: EMBO J.
<304> VOLUME: 4
<305> ISSUE: 7
<306> PAGES: 1761-1768
<307> DATE: 1985
<308> DATABASE ACCESSION NUMBER: NCBI/NM_016816
<309> DATABASE ENTRY DATE: 2003-04-06
<300> PUBLICATION INFORMATION:
<301> AUTHORS: Merlin, G., et al.
<302> TITLE: Molecular cloning and sequence of partial cDNA for
       interferon-induced (2'-5') oligo(A) synthetase mRNA from human
       cells
<303> JOURNAL: Proc. Natl. Acad. Sci. U.S.A.
<304> VOLUME: 80
<305> ISSUE: 16
<306> PAGES: 4904-4908
<307> DATE: 1983
<308> DATABASE ACCESSION NUMBER: NCBI/NM_016816
<309> DATABASE ENTRY DATE: 2003-04-06
```

<400> SEQUENCE: 13

```
gaggcagttc tgttgccact ctctctcctg tcaatgatgg atctcagaaa taccccagcc      60
aaatctctgg acaagttcat tgaagactat ctcttgccag acacgtgttt ccgcatgcaa     120
atcgaccatg ccattgacat catctgtggg ttcctgaagg aaaggtgctt ccgaggtagc     180
tcctaccctg tgtgtgtgtc caaggtggta aagggtggct cctcaggcaa gggcaccacc     240
ctcagaggcc gatctgacgc tgacctggtt gtcttcctca gtcctctcac cacttttcag     300
gatcagttaa atcgccgggg agagttcatc caggaaatta ggagacagct ggaagcctgt     360
caaagagaga gagcactttc cgtgaagttt gaggtccagg ctccacgctg ggcaaccccc     420
cgtgcgctca gcttcgtact gagttcgctc cagctcgggg aggggtgga gttcgatgtg      480
ctgcctgcct ttgatgccct gggtcagttg actggcagct ataaacctaa cccccaaatc     540
tatgtcaagc tcatcgagga gtgcaccgac ctgcagaaag agggcgagtt ctccacctgc     600
ttcacagaac tacagagaga cttcctgaag cagcgcccca ccaagctcaa gagcctcatc     660
cgcctagtca agcactggta ccaaaattgt aagaagaagc ttgggaagct gccacctcag     720
tatgccctgg agctcctgac ggtctatgct tgggagcgag ggagcatgaa aacacatttc     780
aacacagccc aaggatttcg gacggtcttg gaattagtca taaactacca gcaactctgc     840
atctactgga caaagtatta tgactttaaa aaccccatta ttgaaaagta cctgagaagg     900
cagctcacga aacccaggcc tgtgatcctg gacccggcgg accctacagg aaacttgggt     960
ggtgagacc caaagggttg gaggcagctg gcacaagagg ctgaggcctg gctgaattac    1020
ccatgcttta agaattggga tgggtcccca gtgagctcct ggattctgct ggctgaaagc    1080
aacagtacag acgatgagac cgacgatccc aggacgtatc agaaatatgg ttacattgga    1140
acacatgagt accctcattt ctctcataga cccagcacgc tccaggcagc atccacccca    1200
caggcagaag aggactggac ctgcaccatc ctctgaatgc cagtgcatct tggggaaag    1260
ggctccagtg ttatctggac cagttccttc attttcaggt gggactcttg atccagaaa    1320
gacaaagctc ctcagtgagc tggtgtataa tccaagacag aacccaagtc tcctgactcc    1380
tggccttcta tgccctctat cctatcatag ataacattct ccacagcctc acttcattcc    1440
acctattctc tgaaaatatt ccctgagaga gaacagagag atttagataa gagaatgaaa    1500
ttccagcctt gactttcttc tgtgcacctg atgggagggt aatgtctaat gtattatcaa    1560
taacaataaa aataaagcaa ataccaaaaa                                       1590
```

<210> SEQ ID NO 14
<211> LENGTH: 3068
<212> TYPE: DNA
<213> ORGANISM: Homo sapiens
<300> PUBLICATION INFORMATION:
<301> AUTHORS: Hovnanian, A., et al.
<302> TITLE: The human 2',5'-oligoadenylate synthetase locus is composed
      of three distinct genes
<303> JOURNAL: Genomics
<304> VOLUME: 52
<305> ISSUE: 3
<306> PAGES: 267-277
<307> DATE: 1998
<308> DATABASE ACCESSION NUMBER: NCBI/NM_002535
<309> DATABASE ENTRY DATE: 2003-04-03
<300> PUBLICATION INFORMATION:
<301> AUTHORS: Marie, I. and Hovanessian, A.G.
<302> TITLE: The 69-kDa 2-5A synthetase is composed of two homologous
      and adjacent functional domains
<303> JOURNAL: J. Biol. Chem.
<304> VOLUME: 267
<305> ISSUE: 14

```
<306> PAGES: 9933-9939
<307> DATE: 1992
<308> DATABASE ACCESSION NUMBER: NCBI/NM_002535
<309> DATABASE ENTRY DATE: 2003-04-03
<300> PUBLICATION INFORMATION:
<301> AUTHORS: Marie, I., et al.
<302> TITLE: Differential expression and distinct structure of 69- and
       100-kDa forms of 2-5A synthetase
<303> JOURNAL: J. Biol. Chem.
<304> VOLUME: 265
<305> ISSUE: 30
<306> PAGES: 18601-18607
<307> DATE: 1990
<308> DATABASE ACCESSION NUMBER: NCBI/NM_002535
<309> DATABASE ENTRY DATE: 2003-04-03
<300> PUBLICATION INFORMATION:
<301> AUTHORS: Marie, I., et al.
<302> TITLE: Preparation and characterization of polyclonal antibodies
<303> JOURNAL: Biochem. Biophys. Res. Commun.
<304> VOLUME: 160
<305> ISSUE: 2
<306> PAGES: 580-587
<307> DATE: 1989
<308> DATABASE ACCESSION NUMBER: NCBI/NM_002535
<309> DATABASE ENTRY DATE: 2003-04-03
<300> PUBLICATION INFORMATION:
<301> AUTHORS: Hovanessian, A.G., et al.
<302> TITLE: Characterization of 69- and 100-kDa forms of
       2-5A-synthetase
<303> JOURNAL: J. Biol. Chem.
<304> VOLUME: 263
<305> ISSUE: 10
<306> PAGES: 4959
<307> DATE: 1988
<308> DATABASE ACCESSION NUMBER: NCBI/NM_002535
<309> DATABASE ENTRY DATE: 2003-04-03
<300> PUBLICATION INFORMATION:
<301> AUTHORS: Hovanessian, A.G., et al.
<302> TITLE: Identification of 69-kd and 100-kd forms of 2-5A synthetase
<303> JOURNAL: EMBO J.
<304> VOLUME: 6
<305> ISSUE: 5
<306> PAGES: 1273-1280
<307> DATE: 1987
<308> DATABASE ACCESSION NUMBER: NCBI/NM_002535
<309> DATABASE ENTRY DATE: 2003-04-03

<400> SEQUENCE: 14
cggcagccag ctgagagcaa tgggaaatgg ggagtcccag ctgtcctcgg tgcctgctca      60
gaagctgggt tggtttatcc aggaatacct gaagccctac gaagaatgtc agacactgat     120
cgacgagatg gtgaacacca tctgtgacgt ctgcaggaac cccgaacagt tcccctggt      180 gcagggagtg gccataggtg gctcctatgg acggaaaaca gtcttaagag gcaactccga     240
tggtaccctt gtccttttct tcagtgactt aaaacaattc caggatcaga agagaagcca     300
acgtgacatc ctcgataaaa ctggggataa gctgaagttc tgtctgttca cgaagtggtt     360
gaaaaacaat ttcgagatcc agaagtccct tgatgggtcc accatccagg tgttcacaaa     420
aaatcagaga atctctttcg aggtgctggc cgccttcaac gctctgagct taatgataa      480 tcccagcccc tggatctatc gagagctcaa aagatccttg gataagacaa atgccagtcc     540
tggtgagttt gcagtctgct tcactgaact ccagcagaag ttttttgaca accgtcctgg     600
aaaactaaag gatttgatcc tcttgataaa gcactggcat caacagtgcc agaaaaaaat     660
caaggattta ccctcgctgt ctccgtatgc cctggagctg cttacggtgt atgcctggga     720 acagggggtgc agaaaagaca actttgacat tgctgaaggc gtcagaacgg ttctggagct     780
gatcaaatgc caggagaagc tgtgtatcta ttggatggtc aactacaact ttgaagatga     840
gaccatcagg aacatcctgc tgcaccagct ccaatcagcg aggccagtaa tcttggatcc     900
```

```
agttgaccca accaataatg tgagtggaga taaaatatgc tggcaatggc tgaaaaaaga      960
agctcaaacc tggttgactt ctcccaacct ggataatgag ttacctgcac catcttggaa     1020
tgtcctgcct gcaccactct tcacgacccc aggccacctt ctggataagt tcatcaagga     1080
gtttctccag cccaacaaat gcttcctaga gcagattgac agtgctgtta acatcatccg     1140
tacattcctt aaagaaaact gcttccgaca atcaacagcc aagatccaga ttgtccgggg     1200
aggatcaacc gccaaaggca cagctctgaa gactggctct gatgccgatc tcgtcgtgtt     1260
ccataactca cttaaaagct acacctccca aaaaaacgag cggcacaaaa tcgtcaagga     1320
aatccatgaa cagctgaaag cctttttggag ggagaaggag gaggagcttg aagtcagctt     1380
tgagcctccc aagtggaagg ctcccagggt gctgagcttc tctctgaaat ccaaagtcct     1440
caacgaaagt gtcagctttg atgtgcttcc tgcctttaat gcactgggtc agctgagttc     1500
tggctccaca cccagccccg aggtttatgc agggctcatt gatctgtata atcctcgga      1560 cctcccggga ggagagtttt ctacctgttt cacagtcctg cagcgaaact tcattcgctc     1620
ccggcccacc aaactaaagg atttaattcg cctggtgaag cactggtaca agagtgtga      1680 aaggaaactg aagccaaagg ggtctttgcc cccaaagtat gccttggagc tgctcaccat     1740
ctatgcctgg gagcagggga gtggagtgcc ggattttgac actgcagaag gtttccggac     1800
agtcctggag ctggtcacac aatatcagca gctcggcatc ttctggaagg tcaattacaa     1860
ctttgaagat gagaccgtga ggaagtttct actgagccag ttgcagaaaa ccaggcctgt     1920
gatcttggac ccaggcgaac ccacaggtga cgtgggtgga ggggaccgtt ggtgttggca     1980
tcttctggac aaagaagcaa aggttaggtt atcctctccc tgcttcaagg atgggactgg     2040
aaacccaata ccaccttgga aagtgccggt aaaagtcatc taaaggaggc gttgtctgga     2100
aatagccctg taacaggctt gaatcaaaga acttctccta ctgtagcaac ctgaaattaa     2160
ctcagacaca aataaaggaa acccagctca caggagctta acagctggt cagccccct      2220 aagcccccac tacaagtgat cctcaggcag gtaaccccag attcatgcac tgtagggctg     2280
ggcgcagcat ccctaggtct ctacccagta gatgccacta gccctcctct cccagtgaca     2340
accaaaagtc ttcacatgtt caaacgttcc cctgggttca cagatctttc tgcctttggc     2400
ttttggctcc accctctttta gctgttaatt tgagtactta tggccctgaa agcggccacg     2460
gtgcctccag atggcaggtt tgcaatccaa gcaggaagaa ggaaaagata cccaaaggtc     2520
aagaacacag tgattttatt agaagtttca tccgcaaatt ttcttccatt tcattgctca     2580
gaatgtcatg tggttacctg taacttgaag gtggctacaa agatgactgt ggaggtggtt     2640
gcacttgcca cccaaggatg tctgccacac ctctccaagc cctcctacct accaagatat     2700
acctgatata tccaccagat atctcctcag atatacttgg ttctctccac caggttcttt     2760
ctttaaagca ggattctcaa ctttgatact tactcacatt gggctagaca gttctttgtt     2820
tggaggctct cttgtgcatg taggatgttg agcagcatgt gtggcctgta cccagtacat     2880
gccacccagt tgtgacaatt aaaagtgtct tgagacttta tcatgtgtct tctgccctag     2940
gtgagaaccc ttgcactaca ggaaccctac acccaacctg gggggaatgt agggaagagg     3000
tgccaagcca accgtggggt tagctctaat tattaagtta tgcattataa ataaatacca     3060
aaaaattg                                                             3068
```

<210> SEQ ID NO 15
<211> LENGTH: 6270
<212> TYPE: DNA
<213> ORGANISM: Homo sapiens

```
<300> PUBLICATION INFORMATION:
<301> AUTHORS: Rebouillat, D., et al.
<302> TITLE: The 100-kDa 2',5'-oligoadenylate synthetase catalyzing
       preferentially the synthesis of dimeric pppA2'p5'A molecules
<303> JOURNAL: J. Biol. Chem.
<304> VOLUME: 274
<305> ISSUE: 3
<306> PAGES: 1557-1565
<307> DATE: 1999
<308> DATABASE ACCESSION NUMBER: NCBI/AF063613
<309> DATABASE ENTRY DATE: 1999-05-04
<300> PUBLICATION INFORMATION:
<301> AUTHORS: Rebouillat, D., and Hovanessian, A.G.
<302> TITLE: Direct Submission
<303> JOURNAL: Submitted (07-May-1998) Dept. of AIDS and Retroviruses,
       Institut Pasteur
<304> VOLUME: 0
<305> ISSUE: 0
<306> PAGES: 0
<307> DATE: 1998
<308> DATABASE ACCESSION NUMBER: NCBI/AF063613
<309> DATABASE ENTRY DATE: 1999-05-04

<400> SEQUENCE: 15
gccctgcttc cccttgcacc tgcgccgggc ggccatggac ttgtacagca ccccggccgc    60
tgcgctggac aggttcgtgg ccagaaggct gcagccgcgg aaggagttcg tagagaaggc   120
gcggcgcgct ctgggcgccc tggccgctgc cctgaggag cgcggggggcc gcctcggtgc   180 tgctgccccg cgggtgctga aaactgtcaa gggaggctcc tcgggccggg gcacagctct   240
caagggtggc tgtgattctg aacttgtcat cttcctcgac tgcttcaaga gctatgtgga   300
ccagagggcc cgccgtgcag agatcctcag tgagatgcgg gcatcgctgg aatcctggtg   360
gcagaaccca gtccctggtc tgagactcac gtttcctgag cagagcgtgc ctggggccct   420
gcagttccgc ctgacatccg tagatcttga ggactggatg gatgttagcc tggtgcctgc   480
cttcaatgtc ctgggtcagg ccggctccgc ggtcaaaccc aagccacaag tctactctac   540
cctcctcaac agtggctgcc aaggggcga gcatgcggcc tgcttcacag agctgcggag   600
gaactttgtg aacattcgcc cagccaagtt gaagaaccta atcttgctgg tgaagcactg   660
gtaccaccag gtgtgcctac aggggttgtg gaaggagacg ctgccccgg tctatgccct   720 ggaattgctg accatcttcg cctgggagca gggctgtaag aaggatgctt tcagcctagg   780
cgaaggcctc cgaactgtcc tgggcctgat ccaacagcat cagcacctgt gtgttttctg   840
gactgtcaac tatggcttcg aggaccctgc agttgggcag ttcttgcagc ggcacgttaa   900
gagacccagg cctgtgatcc tggacccagc tgaccccaca tgggacctgg ggaatggggc   960
agcctggcac tgggatttgc atgcccagga ggcagcatcc tgctatgacc cccatgctt  1020 tctgaggggg atggggggacc cagtgcagtc ttggaagggg ccgggccttc cacgtgctgg  1080
atgctcaggt ttgggccacc ccatccagct agacctaac cagaagaccc ctgaaaacag  1140
caagagcctc aatgctgtgt acccaagagc agggagcaaa cctccctcat gcccagctcc  1200 tggcccact gcggagccag catcgtaccc ctctgtgccg ggaatggcct tggacctgtc  1260
tcagatcccc accaaggagc tggaccgctt catccaggac cacctgaagc cgagccccca  1320
gttccaggag caggtgaaaa aggccatcga catcatcttg cgctgcctcc atgagaactg  1380
tgttcacaag gcctcaagag tcagtaaagg gggctcattt ggccggggca cagacctaag  1440
ggatggctgt gatgttgaac tcatcatctt cctcaactgc ttcacggact acaaggacca  1500 gggggccccgc cgcgcagaga tccttgatga gatgcgagcg cacgtagaat cctggtggca  1560
ggaccaggtg cccagcctga gccttcagtt tcctgagcag aatgtgcctg aggctctgca  1620
```

```
gttccagctg gtgtccacag ccctgaagag ctggacggat gttagcctgc tgcctgcctt   1680
cgatgctgtg gggcagctca gttctggcac caaaccaaat ccccaggtct actcgaggct   1740
cctcaccagt ggctgccagg agggcgagca taaggcctgc ttcgcagagc tgcggaggaa   1800
cttcatgaac attcgccctg tcaagctgaa gaacctgatt ctgctggtga agcactggta   1860
ccgccaggtt gcggctcaga caaaggaaa aggaccagcc cctgcctctc tgccccagc    1920
ctatgccctg gagctcctca ccatctttgc ctgggagcag ggctgcaggc aggattgttt   1980
caacatggcc caaggcttcc ggacggtgct ggggctcgtg caacagcatc agcagctctg   2040
tgtctactgg acggtcaact atagcactga ggacccagcc atgagaatgc accttcttgg   2100
ccagcttcga aaacccagac ccctggtcct ggaccccgct gatcccacct ggaacgtggg   2160
ccacggtagc tgggagctgt tgcccaggaa gcagcagcg ctggggatgc aggcctgctt    2220
tctgagtaga gacgggacat ctgtgcagcc ctgggatgtg atgccagccc tcctttacca   2280
aaccccagct ggggaccttg acaagttcat cagtgaattt ctccagccca accgccagtt   2340
cctggcccag gtgaacaagg ccgttgatac catctgttca tttttgaagg aaaactgctt   2400
ccggaattct cccatcaaag tgatcaaggt ggtcaagggt ggctcttcag ccaaaggcac   2460
agctctgcga ggccgctcag atgccgacct cgtggtgttc ctcagctgct tcagccagtt   2520
cactgagcag ggcaacaagc gggccgagat catctccgag atccgagccc agctggaggc   2580
atgtcaacag gagcggcagt tcgaggtcaa gtttgaagtc tccaaatggg agaatccccg   2640
cgtgctgagc ttctcactga catcccagac gatgctggac cagagtgtgg actttgatgt   2700
gctgccagcc tttgacgccc taggccagct ggtctctggc tccaggccca gctctcaagt   2760
ctacgtcgac ctcatccaca gctacagcaa tgcgggcgag tactccacct gcttcacaga   2820
gctacaacgg gacttcatca tctctcgccc taccaagctg aagagcctga tccggctggt   2880
gaagcactgg taccagcagt gtaccaagat ctccaagggg agaggctccc taccccaca   2940
gcacgggctg gaactcctga ctgtgtatgc ctggagcag ggcgggaagg actcccagtt    3000
caacatggct gagggcttcc gcacggtcct ggagctggtc acccagtacc gccagctctg   3060
tatctactgg accatcaact acaacgccaa ggacaagact gttggagact tcctgaaaca   3120
gcagcttcag aagcccaggc ctatcatcct ggatccggct gacccgacag gcaacctggg   3180
ccacaatgcc cgctgggacc tgctggccaa ggaagctgca gcctgcacat ctgccctgtg   3240
ctgcatggga cggaatggca tccccatcca gccatggcca gtgaaggctg ctgtgtgaag   3300
ttgagaaaat cagcggtcct actggatgaa gagaagatgg acaccagccc tcagcatgag   3360
gaaattcagg gtcccctacc agatgagaga gattgtgtac atgtgtgtgt gagcacatgt   3420
gtgcatgtgt gtgcacacgt gtgcatgtgt gtgttttagt gaatctgctc tcccagctca   3480
cacactcccc tgcctcccat ggcttacaca ctaggatcca gactccatgg tttgacacca   3540
gcctgcgttt gcagcttctc tgtcacttcc atgactctat cctcatacca ccactgctgc   3600
ttcccaccca gctgagaatg cccccctccc tcctgactcc tctctgccca t gcaaattagc 3660
tcacatcttt cctcctgctg caatccatcc cttcctccca ttggcctctc cttgccaaat   3720
ctaaatactt tatataggga tggcagagag ttcccatctc atctgtcagc cacagtcatt   3780
tggtactggc tacctggagc cttatcttct gaagggtttt aaagaatggc caattagctg   3840
agaagaatta tctaatcaat tagtgatgtc tgccatggat gcagtagagg aaagtggtgg   3900
tacaagtgcc atgattgatt agcaatgtct gcactggata tggaaaaaag aaggtgcttg   3960
caggtttaca gtgtatatgt gggctattga agagccctct gagctcggtt gctagcagga   4020
```

```
gagcatgccc atattggctt actttgtctg ccacagacac agacagaggg agttgggaca    4080
tgcatgctat ggggaccctc ttgttggaca cctaattgga tgcctcttca tgagaggcct    4140
ccttttcttc accttttatg ctgcactcct cccctagttt acacatcttg atgctgtggc    4200
tcagtttgcc ttcctgaatt tttattgggt ccctgttttc tctcctaaca tgctgagatt    4260
ctgcatcccc acagcctaaa ctgagccagt ggccaaacaa ccgtgctcag cctgtttctc    4320
tctgccctct agagcaaggc ccaccaggtc catccaggag gctctcctga cctcaagtcc    4380
aacaacagtg tccacactag tcaaggttca gcccagaaaa cagaaagcac tctaggaatc    4440
ttaggcagaa agggatttta tctaaatcac tggaaaggct ggaggagcag aaggcagagg    4500
ccaccactgg actattggtt tcaatattag accactgtag ccgaatcaga ggccagagag    4560
cagccactgc tactgctaat gccaccacta cccctgccat cactgcccca catggacaaa    4620
actggagtcg agacctaggt tagattcctg caaccacaaa catccatcag ggatggccag    4680
ctgccagagc tgcgggaaga cggatcccac ctcccttcct tagcagaatc taaattacag    4740
ccagacctct ggctgcagag gagtctgaga catgtatgat tgaatgggtg ccaagtgcca    4800
gggggcggag tccccagcag atgcatcctg gccatctgtt gcgtggatga gggagtgggt    4860
ctatctcaga ggaaggaaca ggaaacaaag aaaggaagcc actgaacatc ccttctctgc    4920
tccacaggag tgtcttagac agcctgactc tccacaaacc actgttaaaa cttacctgct    4980
aggaatgcta gattgaatgg gatgggaaga gccttccctc attattgtca ttcttggaga    5040
gaggtgagca accaagggaa gctcctctga ttcacctaga acctgttctc tgccgtcttt    5100
ggctcagcct acagagacta gagtaggtga agggacagag gacagggctt ctaatacctg    5160
tgccatattg acagcctcca tccctgtccc ccatcttggt gctgaaccaa cgctaagggc    5220
accttcttag actcacctca tcgatactgc ctggtaatcc aaagctagaa ctctcaggac    5280
cccaaactcc acctcttgga ttggccctgg ctgctgccac acacatatcc aagagctcag    5340
ggccagttct ggtgggcagc agagacctgc tctgccaagt tgtccagcag cagagtggcc    5400
ctggcctggg catcacaagc cagtgatgct cctgggaaga ccaggtggca ggtcgcagtt    5460
gggtaccttc cattcccacc acacagactc tgggcctccc cgcaaaatgg ctccagaatt    5520
agagtaatta tgagatggtg ggaaccagag caactcaggt gcatgataca aggagaggtt    5580
gtcatctggg tagggcagag aggagggctt gctcatctga acaggggtgt atttcattcc    5640
aggccctcag tctttggcaa tggccacccc ggtgttggca tattggcccc actgtaactt    5700
ttgggggctt cccggtctag ccacaccctc ggatggaaag acttgactgc ataaagatgt    5760
cagttctccc tgagttgatt gataggctta atggtcaccc taaaaacacc cacatatgct    5820
tttcgatgga accagataag ttgacgctaa agttcttatg gaaaaataca cacgcaatag    5880
ctaggaaaac acagggaaag aagagttctg agcagggcct agtcttagcc aatattaaaa    5940
catactatga agcctctgat acttaaacag catggcgctg gtacgtaaat agaccaatgc    6000
agttaggtgg ctctttccaa gactctgggg aaaaaagtag taaaaagcta aatgcaatca    6060
atcagcaatt gaaagctaag tgagagagcc agagggcctc cttggtggta aaagagggtt    6120
gcatttcttg cagccagaag gcagagaaag tgaagaccaa gtccagaact gaatcctaag    6180
aaatgcagga ctgcaaagaa attggtgtgt gtgtgtgtgt gtgtgtgtgt gtgtgtttaa    6240
tttttaaaaa gttttttattc ggaatccgcg                                    6270
```

<210> SEQ ID NO 16

<211> LENGTH: 1412
<212> TYPE: DNA
<213> ORGANISM: Mus musculus
<300> PUBLICATION INFORMATION:
<301> AUTHORS: Coccia, E.M., et al.
<302> TITLE: A full-length murine 2-5A synthetase cDNA transfected in
       NIH-3T3 cells
<303> JOURNAL: Virology
<304> VOLUME: 179
<305> ISSUE: 1
<306> PAGES: 228-233
<307> DATE: 1990
<308> DATABASE ACCESSION NUMBER: NCBI/M33863
<309> DATABASE ENTRY DATE: 1993-06-11

<400> SEQUENCE: 16

```
ccaggctggg agacccagga agctccagac ttagcatgga gcacggactc aggagcatcc      60
cagcctggac gctggacaag ttcatagagg attacctcct tcccgacacc acctttggtg     120
ctgatgtcaa atcagccgtc aatgtcgtgt gtgatttcct gaaggagaga tgcttccaag     180
gtgctgccca cccagtgagg gtctccaagg tggtgaaggg tggctcctca ggcaaaggca     240
ccacactcaa gggcaggtca gacgctgacc tggtggtgtt ccttaacaat ctcaccagct     300
ttgaggatca gttaaaccga cggggagagt tcatcaagga aattaagaaa cagctgtacg     360
aggttcagca tgagagacgt tttagagtca agtttgaggt ccagagttca tggtggccca     420
acgcccggtc tctgagcttc aagctgagcg ccccccatct gcatcaggag gtggagtttg     480
atgtgctgcc agcctttgat gtcctgggtc atgttaatac ttccagcaag cctgatccca     540
gaatctatgc catcctcatc gaggaatgta cctccctggg gaaggatggc gagttctcta     600
cctgcttcac ggagctccag cggaacttcc tgaagcagcg cccaaccaag ctgaagagtc     660
tcatccgcct ggtcaagcac tggtaccaac tgtgtaagga aagctgggg aagccattgc      720
ctccacagta cgccctagag ttgctcactg tctttgcctg ggaacaaggg aatggatgtt     780
atgagttcaa cacagcccag ggcttccgga ccgtcttgga actggtcatc aattatcagc     840
atcttcgaat ctactggaca aagtattatg actttcaaca ccaggaggtc tccaaatacc     900
tgcacagaca gctcagaaaa gccaggcctg tgatcctgga cccagctgac caacaggga      960
atgtggccgg tgggaaccca gagggctgga ggcggttggc tgaagaggct gatgtgtggc    1020
tatggtaccc atgttttatt aaaaaggatg gttcccgagt gagctcctgg gatgtgccga    1080
cggtggttcc tgtaccttt gagcaggtag aagagaactg acatgtatc ctgctgtgag     1140
cacagcagca cctgcccagg agactgctgg tcagggcat ttgctgctct gctgcaggcc    1200
catgacccag tgagggaggg ccccacctgg catcagactc cgtgcttctg atgcctgcca    1260
gccatgtttg actcctgtcc aatcacagcc agccttcctc aacagattca gaaggagagg    1320
aaagaacaca cgcttggtgt ccatctgtcc acctgttgga aggttctgtc tgacaaagtc    1380
tgatcaacaa taaaccacag caggtgccgt ca                                  1412
```

<210> SEQ ID NO 17
<211> LENGTH: 20
<212> TYPE: DNA
<213> ORGANISM: Artificial Sequence
<220> FEATURE:
<223> OTHER INFORMATION: Antisense ODN (p40 subunit)

<400> SEQUENCE: 17

```
tttctgagat ccatcattga                                                  20
```

<210> SEQ ID NO 18

```
<211> LENGTH: 17
<212> TYPE: DNA
<213> ORGANISM: Artificial Sequence
<220> FEATURE:
<223> OTHER INFORMATION: Antisense ODN (p69 subunit)

<400> SEQUENCE: 18
tccccatttc ccattgc                                                    17

<210> SEQ ID NO 19
<211> LENGTH: 20
<212> TYPE: DNA
<213> ORGANISM: Artificial Sequence
<220> FEATURE:
<223> OTHER INFORMATION: Control ODN sequence

<400> SEQUENCE: 19
gtctatgaat actttcctag                                                 20

<210> SEQ ID NO 20
<211> LENGTH: 17
<212> TYPE: DNA
<213> ORGANISM: Artificial Sequence
<220> FEATURE:
<223> OTHER INFORMATION: Control ODN sequence

<400> SEQUENCE: 20
cacctctatc tctctcg                                                    17
```